(12) United States Patent
Nordhoff et al.

(10) Patent No.: US 9,206,136 B2
(45) Date of Patent: *Dec. 8, 2015

(54) PYRAZOLYL-BASED CARBOXAMIDES I

(71) Applicant: Grünenthal GmbH, Aachen (DE)

(72) Inventors: Sonja Nordhoff, Aachen (DE); Sebastian Wachten, Hürth (DE); Achim Kless, Aachen (DE); Felix Voss, Aachen (DE); Stefanie Ritter, Köln (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/152,695

(22) Filed: Jan. 10, 2014

(65) Prior Publication Data

US 2014/0194443 A1    Jul. 10, 2014

Related U.S. Application Data

(60) Provisional application No. 61/750,853, filed on Jan. 10, 2013.

(30) Foreign Application Priority Data

Jan. 10, 2013    (EP) .................................... 13000118

(51) Int. Cl.
| | |
|---|---|
| *C07D 231/14* | (2006.01) |
| *C07D 405/14* | (2006.01) |
| *C07D 403/04* | (2006.01) |
| *C07D 405/10* | (2006.01) |
| *C07D 401/12* | (2006.01) |
| *C07D 417/14* | (2006.01) |
| *C07D 417/10* | (2006.01) |
| *C07D 401/10* | (2006.01) |
| *C07D 413/14* | (2006.01) |
| *C07D 401/14* | (2006.01) |
| *C07D 403/10* | (2006.01) |
| *C07D 413/10* | (2006.01) |

(52) U.S. Cl.
CPC ............ *C07D 231/14* (2013.01); *C07D 401/10* (2013.01); *C07D 401/12* (2013.01); *C07D 401/14* (2013.01); *C07D 403/04* (2013.01); *C07D 403/10* (2013.01); *C07D 405/10* (2013.01); *C07D 405/14* (2013.01); *C07D 413/10* (2013.01); *C07D 413/14* (2013.01); *C07D 417/10* (2013.01); *C07D 417/14* (2013.01)

(58) Field of Classification Search
CPC .. C07D 231/14; C07D 405/14; C07D 403/04; C07D 405/10; C07D 401/12; C07D 417/14; C07D 417/10; C07D 401/10; C07D 413/14; C07D 401/14; C07D 403/10; C07D 413/10
See application file for complete search history.

(56) References Cited

U.S. PATENT DOCUMENTS

| | | | |
|---|---|---|---|
| 6,958,339 B2 | 10/2005 | Kubota et al. | |
| 2006/0100208 A1 | 5/2006 | Makriyannis et al. | |

FOREIGN PATENT DOCUMENTS

| | | | |
|---|---|---|---|
| EP | 1176140 A1 | 1/2002 | |
| WO | 0121160 A2 | 3/2001 | |
| WO | 0121160 A3 | 3/2001 | |
| WO | 03035602 A2 | 5/2003 | |
| WO | 03037274 A2 | 5/2003 | |
| WO | 03037274 A3 | 5/2003 | |
| WO | 2005009539 A2 | 2/2005 | |
| WO | 2005016877 A2 | 2/2005 | |
| WO | 2006067202 A1 | 6/2006 | |
| WO | 2007024744 A2 | 8/2006 | |
| WO | 2007002559 A1 | 1/2007 | |
| WO | 2007043400 A1 | 4/2007 | |
| WO | 2007087427 A2 | 8/2007 | |
| WO | 2007087441 A2 | 8/2007 | |
| WO | 2009011850 A2 | 1/2009 | |
| WO | 2009012283 A1 | 1/2009 | |
| WO | 2009027393 A2 | 3/2009 | |
| WO | 2009052062 A1 | 4/2009 | |
| WO | 2009076454 A2 | 6/2009 | |
| WO | 2009076454 A3 | 6/2009 | |
| WO | 2009089305 A1 | 7/2009 | |
| WO | 2010006725 A1 | 1/2010 | |
| WO | 2010043676 A1 | 4/2010 | |
| WO | 2010122089 A1 | 10/2010 | |
| WO | 2011042797 A1 | 4/2011 | |
| WO | 2012107434 A1 | 8/2012 | |
| WO | 2012139930 A1 | 10/2012 | |
| WO | WO 2012139930 A1 * | 10/2012 | |
| WO | 2012168361 A1 | 12/2012 | |

OTHER PUBLICATIONS

WebMD, Psoriasis—Prevention, http://www.webmd.com/skin-problems-and-treatments/psoriasis/psoriasis-prevention, accessed Dec. 8, 2014.*
Soeken et al. Rheumatology 2003, 42, 652-659.*
Mayo Clinic, Asthma—Prevention, http://www.mayoclinic.org/diseases-conditions/asthma/basics/prevention/con-20026992, accesses Dec. 8, 2014.*
Yassin, FA. J. Microbiol. Antimicrob. 2010, 2, 93-99.*
European Search Report for EP 13000117.5 dated May 23, 2013.
(Continued)

*Primary Examiner* — Matthew Coughlin
(74) *Attorney, Agent, or Firm* — Norris McLaughlin & Marcus, P.A.

(57) ABSTRACT

The invention relates to pyrazolyl-based carboxamide compounds useful as ICRAC inhibitors, to pharmaceutical compositions containing these compounds and to these compounds for the use in the treatment and/or prophylaxis of diseases and/or disorders, in particular inflammatory diseases and/or inflammatory disorders.

17 Claims, No Drawings

(56) References Cited

OTHER PUBLICATIONS

European Search Report for EP 13000118.3 dated May 23, 2013.
Y. Amemiya, et al., "Preparation of 2-Chloro-5-Nitrobenzamides as Lipid Modulators for Treatment of Osteoporosis and Diabetes", Database Caplus [Online] Chemical Abstracts Service, XP-002696312, Columbus, Ohio, US; 2003.
A. Cherkasov, "Targeting the Binding Function 3 (BF3) Site of the Human Androgen Receptor through Virtual Screening", Database Caplus [Online] Chemical Abstracts Service, XP-002696311, Columbus, Ohio, US; 2011.
N. Lack, et al., "Targeting the Binding Function 3 (BF3) Site of the Human Androgen Receptor through Virtual Screening", Journal of Medicinal Chemistry, American Chemical Society, Nov. 2011, vol. 54, No. 24, pp. 8563-8573.
L. A. T. Cleghorn, et al., "Identification of Inhibitors of the Leishmania cdc2-Related Protein Kinase CRK3", ChemMedChem, vol. 6, No. 12, Dec. 2011, pp. 2214-2224, Weinheim.
S. Feske, "Calcium Signalling in Lymphocyte Activation and Disease", Department of Pathology New York University School of Medicine, Nature Publishing Group, vol. 7, pp. 690-706, online, Sep. 2007.
S. Feske, et al., "A Mutation in Orai1 Causes Immune Deficiency by Abrogating CRAC Channel Function", Nature Publishing Group, vol. 44, pp. 179-185, May 2006, online.
Y. Gwak, et al., "Biochemical and Functional Characterization of Orai Proteins", Journal of Biological Chemistry, vol. 282, No. 22, Jun. 1, 2007, pp. 16232-16243, USA.
M. Hoth, et al., "Depletion of Intracellular Calcium Stores Activates a Calcium Current in Mast Cells", Letters to Nature, vol. 355, pp. 353-356, Jan. 23, 1992, online.
J. Ren, et al., "Regioselective Synthesis and Base Catalyzed Transacylation of Substituted 1H-Pyrazole-4-carboxamides", Chinese Journal of Chemistry, 2002, vol. 20, pp. 96-102.
H. H. Kerschbaum, et al., "Single-Channel Recording of a Store-Operated Ca 2+ Channel in Jurkat T Lymphocytes", Science, www.sciencemag.org, vol. 283, pp. 836-839, Feb. 5, 1999.
M. Oh-Hora, et al., "Calcium Signaling in Lymphocytes", Curr Opin Immunol, National Institutes of Health, Jun. 2008, pp. 250-258.
C. Peinelt, et al., "Amplification of CRAC current by STIM1 and CRACM1(Orai1)", Nature Cell Biology, vol. 8, No. 7, pp. 771-773, Jul. 2006, Nature Publishing Group, online.
S. Plescia, et al., "Some Acetyl Substituted Pyrazolo [1,5-a] pyrimidin-5(4H)one Derivatives", Journal of Heterocyclic Chemistry, vol. 11, No. 4, pp. 623-626, Aug. 1974, Italy.
M. Prakriya, et al., "Orai1 is an essential pore subunit of the CRAC channel", Letters to Nature, Nature Publishing Group, vol. 443, pp. 230-233, Sep. 2006, online.
J Soboloff, et al., "Orai1 and STIM Reconstitute Store-operated Calcium Channel Function", Journal of Biological Chemistry, vol. 281, No. 31, pp. 20661-20665, Jul. 2006, online.
M. Vig, et al., "CRACM1 Multimers Form the Ion-Selective Pore of the CRAC Channel", Current Biology 16, pp. 2073-2079, Oct. 24, 2006, online.
M. Hoth, et al., Calcium Release-Activgated Calcium Current in Rat Mast Cells, Journal of Physiology, pp. 359-386, 1993, Great Brittain.
A. Lepple-Wienhues, et al., "Conductance and Permeation of Monovalent Cations through Depletion-Activated CA2+ Channels (ICRAC) in Jurkat T Cells", Biophysical Journal, vol., 71, pp. 787-794, Aug. 1996, USA.
R. Lewis, "Store-Operated Calcium Channels", Advances in Second Messenger and Phosphoprotein Reseach, vol. 33, pp. 279-307, 1999, USA.
Z. Li, et al., "Mapping the Interacting Domains of STIM1 and Orai1 in CA2+ Release-activated CA2+ Channel Activation", Journal of Biological Chemistry, vol. 282, No. 40, pp. 29448-29456, Oct. 5, 2007, online.
R. M. Luik, et al., "The Elementary Unit of Store-operated CA2+ Entry: Local Activation of CRAC Channels by STIM1 at ER-plasma Membrane Junctions", The Journal of Cell Biology, vol. 174, No. 6, pp. 815-825, Sep. 11, 2006, online.
G. N. Lipunova. et al., "Flourine-Containing Heterocycles: XII. Flourine-Containing Quinazolan-4-ones and Azolo [a] quinazolinone Derivatives", Russian Journal of Organic Chemistry, vol. 41, No. 7, 2005, pp. 1071-1080.
J. Liou, et al. "STIM Is a Ca2+ Sensor Essential for Ca2+-Store-Depletion-Triggered Ca2+ Influx", National Institutes of Health, Jul. 2005, pp. 1235-1241.
A. B. Parekh, et al., "Store Depletion and Calcium Influx", Physiological Reviews, The American Physiological Society, vol. 77, No. 4, pp. 901-930, Oct. 1997, USA.
J. W. Putney, Jr, et al., "A Model for Receptor-Regulated Calcium Entry", Cell Calcium 7, pp. 1-12, 1986, USA.
J. Roos, et al., "STIM1, an Essential and Conserved Component of Store-operated Ca2+ Channel Function", The Journal of Cell Biology, vol. 169, No. 3, May 9, 2005, pp. 435-445, online.
M. M. Wu, et al., "Ca2+ store depletion causes STIM1 to accumulate in ER regions closely associated with the plasma membrane", The Journal of Cell Biology, vol. 174, No. 6, Sep. 11, 2006, pp. 803-813, online.
S. L. Zhang, et al., "STIM1 is a CA2+ sensor that activates CRAC channels and migrates from the Ca2+ store to the plasma membrane", Letters to Nature, Nature Publishing Group, vol. 437, Oct. 6, 2005, pp. 902-905, online.
S. L. Zhang, et al., "Genome-wide RNAi screen of Ca2+ influx identifies genes that regulate Ca2+ release-activated Ca2+ channel activity", PNAS, vol. 103, No. 24, pp. 9357-9362, The National Academy of Sciences of the USA, Jun. 13, 2006.
A. B. Parekh, et al., "Store-Operated Calcium Channels", Physiological Reviews, The American Physiological Society, vol. 85; pp. 757-810, 2005, USA.

* cited by examiner

PYRAZOLYL-BASED CARBOXAMIDES I

This application claims priority to the European patent application EP 13000118.3 and U.S. Provisional application 61/750,853 filed Jan. 10, 2013.

FIELD OF THE INVENTION

The invention relates to biologically active compounds, namely substituted pyrazol-3-yl-carboxamides bearing a substituted phenyl or 6-membered heteroaryl moiety, useful for inhibition of the Calcium Release Activated Calcium channel (CRAC) and hence for inhibition of the Calcium Release Activated Calcium current (ICRAC), to pharmaceutical compositions containing these compounds and also to these compounds for use in immuosupression and in the treatment and/or prophylaxis of conditions, diseases and/or disorders, in particular immune disorders, inflammatory conditions and allergic diseases.

BACKGROUND OF THE INVENTION

Calcium-conducting channels in the plasma membrane can appear very diverse (Parekh & Putney 2005) including voltage-gated ion channels (VOC's), receptor-operated ion channels (ROC's), but also store-operated channels (SOC's; Putney, 1986) that are activated in response to a decrease of the intraluminal Calcium concentration within i.e. the endoplasmic reticulum (ER). The latter have been demonstrated to serve as the main Calcium entry mechanisms in non-excitable cells.

Amongst the distinct SOCs, the CRAC current (ICRAC) is certainly characterized best and displays biophysical features such as high selectivity for Calcium ions, low conductance, and inward rectification (Hoth & Penner, 1992; Hoth & Penner, 1993; Parekh & Penner, 1997; Lepple-Wienhues & Cahalan, 1996; Kerschbaum & Cahalan, 1999). There's substantial evidence that the channels conducting CRAC predominantly rely on two proteins, Orai1 and Stim1 (Roos et al., 2005; Feske et al., 2006; Peinelt et al., 2006). Orai1 constitutes the channel pore within the plasma membrane (Prakriya et al., 2006; Vig et al., 2006), whereas Stim1 has been demonstrated to function as the sensor of the luminal Calcium concentration (Liou et al., 2005; Zhang et al., 2006).

In a physiological setting, ICRAC is activated in response to the engagement of cell-surface receptors that positively couple to phospholipase C (PLC). PLC increases the concentration of the soluble messenger inositol-1,4,5-trisphosphate (IP3), which opens ER membrane-resident IP3-receptors. Thus, IP3 triggers the release of Calcium from internal stores resulting in a drop of the luminal Calcium concentration (Lewis, 1999), which is sensed by Stim1. The Stim1 molecule undergoes conformational changes inducing clustering with other Stim1 molecules just underneath the plasma membrane. At these sites, Stim1 can open the Orai1 pore by bridging the ER-PM gap with its C-terminal tail (Zhang et al., 2005; Luik et al., 2006; Soboloff et al. 2006, Wu et al. 2006; Li et al., 2007).

The above described process serves in signaling pathways of immune cells such as lymphocytes and mast cells. I.e. the activation of antigen or Fc receptors stimulates the release of Calcium from intracellular stores, and subsequent activation of ICRAC that impacts on downstream processes such as gene expression and cytokine release (Feske, 2007; Gwack et al., 2007; Oh-hora & Rao 2008).

The major contribution ICRAC provides to these signaling events has been convincingly demonstrated in patients suffering from severe combined immunodeficiency (SCID) due to a defect in T-cell activation. T cells and fibroblasts from these patients exhibited a strong attenuation of store-operated Calcium entry carried by ICRAC (Feske et al., 2006). This suggests CRAC channel modulators to serve as treatment in disease states caused by activated inflammatory cells.

The activation of antigen or Fc receptors stimulates the release of Calcium from intracellular stores and subsequent, sustained activation of ICRAC. Calcium carried by ICRAC activates calcineurin (CaN), which dephosphorylates the transcription factor NFAT. Upon dephosphorylation, NFAT shuttles into the nucleus and regulates gene expression in various ways depending on the nature of the stimulus as well as on the cell/tissue type.

NFAT participates in the transactivation of cytokine genes that regulate T-cell proliferation and other genes that control immune responses. Taking into account that the expression of cytokines such as IL-2, IL-4, IL-5, IL-8, IL-13, tumor necrosis factor alpha (TNFα), granulocyte colony-stimulating factor (G-CSF), and gamma-interferon (INFγ) is prone to be controlled via transcriptional elements for NFAT, the impact of the ICRAC/CaN/NFAT signaling pathway on pro-inflammatory processes becomes apparent. The inhibition of this pathway has been demonstrated to be efficacious in patients by the use of drugs such as CsA and FK506, which act by inhibiting CaN.

A hallmark of ICRAC signaling in immune cells is that downstream processes such as gene expression rely on sustained Calcium entry rather than transient signals. However, Calcium entry is essential for other processes that can be independent of CaN/NFAT. Direct, Calcium-mediated release of substances (degranulation) such as histamine, heparin, and TNFα occur in i.e. mast cells, and are of rather acute nature. On the molecular level, this already points towards a differentiation potential for ICRAC blockers from calcineurin inhibitors.

Recent findings suggest that CRAC channel modulators can serve as treatment in disease states caused by the activation of inflammatory cells without side effects observed under treatments with i.e. steroids. Such diseases may include but are not limited to asthma, chronic obstructive pulmonary disease, rheumatoid arthritis, inflammatory bowel disease, glomerulonephritis, neuroinflammatory diseases such as multiple sclerosis, and disorders of the immune system.

U.S. Pat. No. 6,958,339, WO 2009/076454 A1, WO 2009/089305 A1, and WO 2010/122089 A1 each disclose a series of pyrazole carboxamide derivatives that are said to possess CRAC channel inhibitory activity which are believed to be useful in the treatment of allergic, inflammatory or autoimmune diseases.

Other small molecules possessing structurally different scaffolds as ICRAC inhibitors are known for instance from WO2005/009539, WO 2007/087427 A2 and WO 2007/087441 A2.

Pyrazole carboxamides as biologically active compounds are also known in the art, e.g. from EP 1176140 B1, US 2006/0100208 A1, WO 2005/016877 A2, WO 2006/076202 A1, WO 2007/002559 A1, WO 2007/024744 A2, WO 2009/011850 A2 and WO 2009/027393.

SUMMARY OF THE INVENTION

The present invention describes a new class of small molecule that is useful for the inhibition of the calcium release activated calcium channel current (thereafter ICRAC inhibitors).

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by CRAC channels.

This object is achieved by the subject matter described herein.

It has surprisingly been found that the substituted compounds of general formula (I), as given below, display potent inhibitory activity against to CRAC channels and are therefore particularly suitable for the prophylaxis and/or treatment of disorders or diseases which are at least partially mediated by CRAC channels.

A first aspect of the present invention therefore relates to a compound of general formula (I), (I)

wherein
$R^1$ denotes H;
  $C_{1-4}$-aliphatic residue, unsubstituted or mono- or polysubstituted; or
  $C_{3-6}$-cycloaliphatic residue or a 3 to 7 membered heterocycloaliphatic residue, in each case unsubstituted or mono- or polysubstituted and in each case optionally connected via a $C_{1-4}$-aliphatic group, which in turn may be unsubstituted or mono- or polysubstituted;
  with the proviso that if $R^1$ represents a 3 to 7 membered heterocycloaliphatic residue, said 3 to 7 membered heterocycloaliphatic residue is connected to the remaining part of the structure according to general formula (I) via a carbon atom of the 3 to 7 membered heterocycloaliphatic residue;
$R^2$ denotes H; F; Cl; Br; I; $NO_2$; CN; $CF_3$; $CF_2H$; $CFH_2$; $R^{13}$; OH; O—$R^{13}$; $NH_2$; N(H)$R^{13}$; N($R^{13}$)$_2$;
T represents C—$R^3$ or N or $N^+$—$O^-$, U represents C—$R^4$ or N or $N^+$—$O^-$, V represents C—$R^5$ or N or $N^+$—$O^-$, W represents C—$R^6$ or N or $N^+$—$O^-$, and X represents C—$R^7$ or N or $N^+$—$O^-$,
with the proviso that 0, 1, 2 or 3 of variables T, U, V, W and X independently of one another represent(s) either N or $N^+$—$O^-$, whereof 0 or 1 of variables T, U, V, W and X independently of one another represent(s) $N^+$—$O^-$ and
with the proviso that at least one of U, V and W does not represent N,
wherein at least one of $R^4$, $R^5$ and $R^6$ is selected from the group consisting of
  $C_{3-6}$-cycloaliphatic residue, unsubstituted or mono- or polysubstituted;
  3 to 7 membered heterocycloaliphatic residue, unsubstituted or mono- or polysubstituted;
  aryl, unsubstituted or mono- or polysubstituted;
  and heteroaryl, unsubstituted or mono- or polysubstituted,
and the remaining substituents of $R^3$, $R^4$, $R^5$, $R^6$ and $R^7$ are independently of one another selected from the group consisting of H; F; Cl; Br; I; $NO_2$; CN; $CF_3$; $CF_2H$; $CFH_2$; $CF_2Cl$; $CFCl_2$; $R^{13}$; $R^{14}$; C(=O)OH; C(=O)—$R^{13}$; C(=O)$R^{14}$; C(=O)—$OR^{13}$; C(=O)—$OR^{14}$; C(=O)—N(H)(OH); C(=N—OH)—H; C(=N—OH)—$R^{13}$; C(=N—OH)—$R^{14}$; C(=N—O—$R^{13}$)—H; C(=N—O—$R^{13}$)—$R^{13}$; C(=N—)—R; C(=N—$O_{13}$)—$R^{14}$; C(=O)$NH_2$; C(=O)—N(H)$R^{13}$; C(=O)—N($R^{13}$)$_2$; C(=O)—N(H)$R^{14}$; C(=O)—N($R^{14}$)$_2$; C(=O)—N($R^{13}$)($R^{14}$); C(=O)—N($R^a$)($R^b$); OH; $OR^{13}$; $OCF_3$; $OCF_2H$; $OCFH_2$; $OCF_2Cl$; $OCFCl_2$; $OR^{14}$; O—C(=O)$R^{13}$; O—C(=O)$R^{14}$; O—C(=O)—N(H)$R^{13}$; O—C(=O)—N(H)$R^{14}$; O—C(=O)—N($R^{13}$)$_2$; O—C(=O)—N($R^{14}$)$_2$; O—C(=O)—N($R^{13}$)($R^{14}$); O—C(=O)—N($R^a$)($R^b$); $NH_2$; N(H)$R^{13}$; N($R^{13}$)$_2$; N(H)$R^{14}$; N($R^{14}$)$_2$; N($R^{13}$)($R^{14}$); N($R^a$)($R^b$); NH—C(=O)—$R^{14}$; NH—C(=O)—$R^{13}$; N($R^{13}$)—C(=O)—$R^{13}$; N($R^{13}$)—C(=O)—$R^{14}$; NH—S(=O)$_2$—$R^{13}$; N($R^{13}$)—S(=O)$_2$—$R^{13}$; NH—S(=O)$_2$—$R^{14}$; N($R^{13}$)—S(=O)$_2$—$R^{14}$; N(H)—C(=O)—$OR^{13}$; N(H)—C(=O)—$OR^{14}$; N($R^{13}$)—C(=O)—$OR^{13}$; N($R^{13}$)—C(=O)—$OR^{14}$; N(H)—C(=O)—$NH_2$; N(H)—C(=O)—N(H)$R^{13}$; N(H)—C(=O)—N(H)$R^{14}$; N(H)—C(=O)—N($R^{13}$)$_2$; N(H)—C(=O)—N($R^{14}$)$_2$; N(H)—C(=O)—N($R^{13}$)($R^{14}$); N(H)—C(=O)—N($R^a$)($R^b$); N($R^{13}$)—C(=O)—$NH_2$; N($R^{13}$)—C(=O)—N(H)$R^{13}$; N($R^{13}$)—C(=O)—N(H)$R^{14}$; N($R^{13}$)—C(=O)—N($R^{13}$)$_2$; N($R^{13}$)—C(=O)—N($R^{14}$)$_2$; N($R^{13}$)—C(=O)—N($R^{13}$)($R^{14}$); N($R^{13}$)—C(=O)—N($R^a$)($R^b$); SH; S—$R^{13}$; $SCF_3$; S—$R^{14}$; S(=O)$_2$OH; S(=O)$_2$—$R^{13}$; S(=O)$_2$—$R^{14}$; S(=O)—$R^{13}$; S(=O)—$R^{14}$; S(=O)$_2$—$OR^{13}$; S(=O)$_2$—$OR^{14}$; S(=O)$_2$—N(H)($R^{13}$); S(=O)$_2$—N($R^{13}$)$_2$; S(=O)$_2$—N(H)($R^{14}$); S(=O)$_2$—N($R^{13}$)($R^{14}$); S(=O)$_2$—N($R^a$)($R^b$);
n represents 0 or 1,
wherein, if n represents 1, then
  J represents C—$R^8$ or N or $N^+$—$O^-$,
  K represents C—$R^9$ or N or $N^+$—$O^-$,
  M represents C—$R^{10}$ or N or $N^+$—$O^-$,
  Q represents C—$R^{11}$ or N or $N^+$—$O^-$, and
  R represents C—$R^{12}$ or N or $N^+$—$O^-$,
  with the proviso that 0, 1, 2 or 3 of variables J, K, M, Q and R independently of one another represent(s) either N or $N^+$—$O^-$, whereof 0 or 1 of variables J, K, M, Q and R independently represents $N^+$—$O^-$,
wherein, if n represents 0, then
  J represents C—$R^8$ or N or N—$O^-$ or O or S or NH or N($C_{1-4}$-aliphatic residue),
  K represents C—$R^9$ or N or $N^+$—$O^-$ or O or S or NH or N($C_{1-4}$-aliphatic residue),
  M represents C—$R^{10}$ or N or $N^+$—$O^-$ or O or S or NH or N($C_{1-4}$-aliphatic residue) and
  Q represents C—$R^{11}$ or N or N—O— or O or S or NH or N($C_{1-4}$-aliphatic residue),
  with the proviso that
  one of J, K, M and Q represents O or S or NH or N($C_{1-4}$-aliphatic residue) and the remaining of J, K, M and Q independently represent C—$R^8$, respectively C—$R^9$, respectively C—$R^{10}$, respectively C—$R^{11}$ or N or N—$O^-$ and
  with the proviso that 0, 1, 2 or 3 of J, K, M and Q independently of one another represent either N or $N^+$—$O^-$, whereof 0 or 1 of variables J, K, M and Q represents $N^+$—$O^-$,
wherein $R^8$, $R^9$, $R^{10}$, $R^{11}$ and $R^{12}$ are independently of one another selected from the group consisting of H; F; Cl; Br; I; $NO_2$; CN; $CF_3$; $CF_2H$; $CFH_2$; $CF_2Cl$; $CFCl_2$; $R^{13}$; $R^{14}$; C(=O)OH; C(=O)—$R^{13}$; C(=O)$R^{14}$; C(=O)—$OR^{13}$; C(=O)—$OR^{14}$; C(=O)—N(H)(OH); C(=N—OH)—H; C(=N—OH)—$R^{13}$; C(=N—OH)—$R^{14}$;

C(=N—O—R$^{13}$)—H; C(=N—O—R$^{13}$)—R$^{13}$; C(=N—O—R$^{13}$)—R$^{14}$; C(=O)NH$_2$; C(=O)—N(H)R$^{13}$; C(=O)—N(R$^{13}$)$_2$; C(=O)—N(H)R$^{14}$; C(=O)—N(R$^{14}$)$_2$; C(=O)—N(R$^{13}$)(R$^{14}$); C(=O)—N(R$^a$)(R$^b$); OH; OR$^{13}$; OCF$_3$; OCF$_2$H; OCFH$_2$; OCF$_2$Cl; OCFCl$_2$; OR$^{14}$; O—C(=O)R$^{13}$; O—C(=O)R$^{14}$; O—C(=O)—N(H)R$^{13}$; O—C(=O)—N(H)R$^{14}$; O—C(=O)—N(R$^1$)$_2$; O—C(=O)—N(R$^{14}$)$_2$; O—C(=O)—N(R$^{13}$)(R$^{14}$); O—C(=O)—N(R$^a$)(R$^b$); NH$_2$; N(H)R$^{13}$; N(R$^{13}$)$_2$; N(H)R$^{14}$; N(R$^{14}$)$_2$; N(R$^{13}$)(R$^{14}$); N(R$^a$)(R$^b$); NH—C(=O)—R$^{14}$; NH—C(=O)—R$^{13}$; N(R$^{13}$)—C(=O)—R$^{13}$; N(R$^{13}$)—C(=O)—R$^{14}$; NH—S(=O)$_2$—R$^{13}$; N(R$^{13}$)—S(=O)$_2$—R$^{13}$; NH—S(=O)$_2$—R$^{14}$; N(R$^{13}$)—S(=O)$_2$—R$^{14}$; N(H)—C(=O)—OR$^{13}$; N(H)—C(=O)—OR$^{14}$; N(R$^{13}$)—C(=O)—OR$^{13}$; N(R$^{13}$)—C(=O)—OR$^{14}$; N(H)—C(=O)—NH$_2$; N(H)—C(=O)—N(H)R$^{13}$; N(H)—C(=O)—N(H)R$^{14}$; N(H)—C(=O)—N(R$^{13}$)$_2$; N(H)—C(=O)—N(R$^{14}$)$_2$; N(H)—C(=O)—N(R$^{13}$)(R$^{14}$); N(H)—C(=O)—N(R$^a$)(R$^b$); N(R$^{13}$)—C(=O)—NH$_2$; N(R$^{13}$)—C(=O)—N(H)R$^{13}$; N(R$^{13}$)—C(=O)—N(H)R$^{14}$; N(R$^{13}$)—C(=O)—N(R$^{13}$)$_2$; N(R$^{13}$)—C(=O)—N(R$^{14}$)$_2$; N(R$^{13}$)—C(=O)—N(R$^{13}$)(R$^{14}$); N(R$^{13}$)—C(=O)—N(R$^a$)(R$^b$); SH; S—R$^{13}$; SCF$_3$; S—R$^{14}$; S(=O)$_2$OH; S(=O)$_2$—R$^{13}$; S(=O)$_2$—R$^{14}$; S(=O)—R$^{13}$; S(=O)—R$^{14}$; S(=O)$_2$—OR$^{13}$; S(=O)$_2$—OR$^{14}$; S(=O)$_2$—N(H)(R$^{13}$); S(=O)$_2$—N(R$^{13}$)$_2$; S(=O)$_2$—N(H)(R$^{14}$); S(=O)$_2$—N(R$^{13}$)(R$^{14}$); S(=O)$_2$—N(R$^a$)(R$^b$);

with the proviso that at least one of R$^8$, R$^9$, R$^{10}$, R$^{11}$ and R$^{12}$ does not denote H;

wherein each R$^{13}$ independently of each other denotes

C$_{1-8}$-aliphatic residue, unsubstituted or mono- or polysubstituted;

or

C$_{3-6}$-cycloaliphatic residue or 3 to 7 membered heterocycloaliphatic residue, in each case unsubstituted or mono- or polysubstituted;

or

C$_{3-6}$-cycloaliphatic residue or 3 to 7 membered heterocycloaliphatic residue, in each case unsubstituted or mono- or polysubstituted, and in each case connected via a C$_{1-4}$-aliphatic residue, unsubstituted or mono- or polysubstituted;

each R$^{14}$ independently of each other denotes aryl and heteroaryl residue, in each case independently of one another unsubstituted or mono- or polysubstituted, or aryl and heteroaryl residue, in each case independently of one another unsubstituted or mono- or polysubstituted and in each case connected via a C$_{1-4}$-aliphatic group, unsubstituted or mono- or polysubstituted;

R$^a$ and R$^b$ together with the N-atom connecting them form a 3 to 7 membered heterocyclic residue, unsubstituted or mono- or polysubstituted;

in which "mono- or polysubstituted" with respect to an "aliphatic group", an "aliphatic residue" a "cycloaliphatic residue" and a "heterocycloaliphatic residue" relates in each case independently of one another, with respect to the corresponding residues or groups, to the substitution of one or more hydrogen atoms each independently of one another by at least one substituent selected from the group consisting of F; Cl; CN; CF$_3$; CF$_2$H; CFH$_2$; CF$_2$Cl; CFCl$_2$; C$_{1-8}$-aliphatic residue; C$_{3-6}$-cycloaliphatic residue; 3 to 7 membered heterocyclic residue; aryl; heteroaryl; aryl, heteroaryl, C$_{3-6}$-cycloaliphatic residue or 3 to 6 membered heterocycloaliphatic, each connected via a C$_{1-4}$-aliphatic group; C(=O)—(C$_{1-8}$-aliphatic residue); C(=O)—C$_{3-6}$-cycloaliphatic residue); C(=O)-(3 to 7 membered heterocyclic residue); C(=O)-(aryl); C(=O)-(heteroaryl); C(=O)OH; C(=O)—O(C$_{1-8}$-aliphatic residue); C(=O)—O(C$_{3-6}$-cycloaliphatic residue); C(=O)—O(3 to 7 membered heterocyclic residue); C(=O)—O(aryl); C(=O)—O(heteroaryl); C(=O)—NH$_2$; C(=O)—N(H)(C$_{1-8}$-aliphatic residue); C(=O)—N(H)(C$_{3-6}$-cycloaliphatic residue); C(=O)—N(H)(3 to 7 membered heterocyclic residue); C(=O)—N(H)(aryl); C(=O)—N(H)(heteroaryl); C(=O)—N(C$_{1-8}$-aliphatic residue)(C$_{1-8}$-aliphatic residue); C(=O)—N(C$_{1-8}$-aliphatic residue)(C$_{3-6}$-cycloaliphatic residue); C(=O)—N(C$_{1-8}$-aliphatic residue)(3 to 7 membered heterocyclic residue); C(=O)—N(C$_{1-8}$-aliphatic residue)(aryl); C(=O)—N(C$_{1-8}$-aliphatic residue) (heteroaryl); OH; =O; O—(C$_{1-8}$-aliphatic residue); O—(C$_{3-6}$-cycloaliphatic residue); O-(3 to 7 membered heterocyclic residue); O-(aryl); O-(heteroaryl); OCF$_3$; OCF$_2$H; OCFH$_2$; OCF$_2$Cl; OCFCl$_2$; O—(C$_{2-4}$-aliphatic group)-OH; O—(C$_{2-4}$-aliphatic group)-O(C$_{1-8}$-aliphatic residue); O—C(=O)—(C$_{1-8}$-aliphatic residue); O—C(=O)—(C$_{3-6}$-cycloaliphatic residue); O—C(=O)-(3 to 7 membered heterocyclic residue); C(=O)-(aryl); C(=O)-(heteroaryl); O—C(=O)—NH$_2$; O—C(=O)—N(H)(C$_{1-8}$-aliphatic residue); O—C(=O)—N(H)(C$_{3-6}$-cycloaliphatic residue); O—C(=O)—N(H)(3 to 7 membered heterocyclic residue); O—C(=O)—N(H)(aryl); O—C(=O)—N(H) (heteroaryl); O—C(=O)—N(C$_{1-8}$-aliphatic residue)(C$_{1-8}$-aliphatic residue); O—C(=O)—N(C$_{1-8}$-aliphatic residue)(C$_{3-6}$-cycloaliphatic residue); O—C(=O)—N(C$_{1-8}$-aliphatic residue)(3 to 7 membered heterocyclic residue); O—C(=O)—N(C$_1$-aliphatic residue)(aryl); O—C(=O)—N(C$_{1-8}$-aliphatic residue)(heteroaryl); NH$_2$; N(H)(C$_{1-8}$-aliphatic residue); N(H)(C$_{3-6}$-cycloaliphatic residue); N(H)(3 to 7 membered heterocyclic residue); N(H)(aryl); N(H)(heteroaryl); N(C$_{1-8}$-aliphatic residue)(C$_{1-8}$-aliphatic residue); N(C$_{1-8}$-aliphatic residue)(C$_{3-6}$-cycloaliphatic residue); N(C$_{1-8}$-aliphatic residue)(3 to 7 membered heterocyclic residue); N(C$_{1-8}$-aliphatic residue) (aryl); N(C$_{1-8}$-aliphatic residue)(heteroaryl); N(H)—C(=O)—(C$_{1-8}$-aliphatic residue); N(H)—C(=O)—(C$_{3-6}$-cycloaliphatic residue); N(H)—C(=O)-(3 to 7 membered heterocyclic residue); N(H)—C(=O)-(aryl); N(H)—C(=O)-(heteroaryl); N(C$_{1-8}$-aliphatic residue)-C(=O)—(C$_{1-8}$-aliphatic residue); N(C$_{1-8}$-aliphatic residue)-C(=O)—(C$_{3-6}$-cycloaliphatic residue); N(C$_{1-8}$-aliphatic residue)-C(=O)-(3 to 7 membered heterocyclic residue); N(C$_{1-8}$-aliphatic residue)-C(=O)-(aryl); N(C$_{1-8}$-aliphatic residue)-C(=O)-(heteroaryl); N(H)—S(=O)$_2$—(C$_{1-8}$-aliphatic residue); N(H)—S(=O)$_2$—(C$_{3-6}$-cycloaliphatic residue); N(H)—S(=O)$_2$-(3 to 7 membered hetero-cyclic residue); N(H)—S(=O)$_2$-(aryl); N(H)—S(=O)$_2$-(heteroaryl); N(C$_{1-8}$-aliphatic residue)-S(=O)$_2$—(C$_{1-8}$-aliphatic residue); N(C$_{1-8}$-aliphatic residue)-S(=O)$_2$—(C$_{3-6}$-cycloaliphatic residue); N(C$_{1-8}$-aliphatic residue)-S(=O)$_2$-(3 to 7 membered heterocyclic residue); N(C$_{1-8}$-aliphatic residue)-S(=O)$_2$-(aryl); N(C$_{1-8}$-aliphatic residue)-S(=O)$_2$-(heteroaryl); N(H)—C(=O)—O(C$_{1-8}$-aliphatic residue); N(H)—C(=O)—O(C$_{3-6}$-cycloaliphatic residue); N(H)—C(=O)—O(3 to 7 membered heterocyclic residue); N(H)—C(=O)—O(aryl); N(H)—C(=O)—O(heteroaryl); N(C$_{1-8}$-aliphatic residue)-C(=O)—O(C$_{1-8}$-aliphatic residue); N(C$_{1-8}$-aliphatic residue)-C(=O)—O(C$_{3-6}$-cycloaliphatic residue);

N(C$_{1-8}$-aliphatic residue)-C(=O)—O(3 to 7 membered heterocyclic residue); N(C$_{1-8}$-aliphatic residue)-C(=O)—O(aryl); N(C$_{1-8}$-aliphatic residue)-C(=O)—O(heteroaryl); N(H)—C(=O)—NH$_2$; N(H)—C(=O)—N(H)(C$_{1-8}$-aliphatic residue); N(H)—C(=O)—N(H)(C$_{3-6}$-cycloaliphatic residue); N(H)—C(=O)—N(H)(3 to 7 membered heterocyclic residue); N(H)—C(=O)—N(H)(aryl); N(H)—C(=O)—N(H)(heteroaryl); N(C$_{1-8}$-aliphatic residue)-C(=O)—NH$_2$; N(C$_{1-8}$-aliphatic residue)-C(=O)—N(H)(C$_{1-8}$-aliphatic residue); N(C$_{1-8}$-aliphatic residue)-C(=O)—N(H)(C$_{3-6}$-cycloaliphatic residue); N(C$_{1-8}$-aliphatic residue)-C(=O)—N(H)(3 to 7 membered heterocyclic residue); N(C$_{1-8}$-aliphatic residue)-C(=O)—N(H)(aryl); N(C$_{1-8}$-aliphatic residue)-C(=O)—N(H)(heteroaryl); N(H)—C(=O)—N(C$_{1-8}$-aliphatic residue)(C$_{1-8}$-aliphatic residue); N(H)—C(=O)—N(C$_{1-8}$-aliphatic residue)(C$_{3-6}$-cycloaliphatic residue); N(H)—C(=O)—N(C$_{1-8}$-aliphatic residue)(3 to 7 membered heterocyclic residue); N(H)—C(=O)—N(C$_{1-8}$-aliphatic residue)(aryl); N(H)—C(=O)—N(C$_{1-8}$-aliphatic residue)(heteroaryl); N(C$_{1-8}$-aliphatic residue)-C(=O)—N(C$_{1-8}$-aliphatic residue)(C$_{1-8}$-aliphatic residue); N(C$_{1-8}$-aliphatic residue)-C(=O)—N(C$_{1-8}$-aliphatic residue)(C$_{3-6}$-cycloaliphatic residue); N(C$_{1-8}$-aliphatic residue)-C(=O)—N(C$_{1-8}$-aliphatic residue)(3 to 7 membered heterocyclic residue); N(C$_{1-8}$-aliphatic residue)-C(=O)—N(C$_{1-8}$-aliphatic residue)(aryl); N(C$_{1-8}$-aliphatic residue)-C(=O)—N(C$_{1-8}$-aliphatic residue)(heteroaryl); S—(C$_{3-6}$-cycloaliphatic residue); S-(3 to 7 membered heterocyclic residue); S-(aryl); S-(heteroaryl); SCF$_3$; S(=O)$_2$OH; S(=O)—(C$_{1-8}$-aliphatic residue); S(=O)—(C$_{3-6}$-cycloaliphatic residue); S(=O)-(3 to 7 membered heterocyclic residue); S(=O)-(aryl); S(=O)-(heteroaryl); S(=O)$_2$—(C$_{1-8}$-aliphatic residue); S(=O)$_2$—(C$_{3-6}$-cycloaliphatic residue); S(=O)$_2$-(3 to 7 membered heterocyclic residue); S(=O)$_2$-(aryl); S(=O)$_2$-(heteroaryl); S(=O)$_2$—O(C$_{1-8}$-aliphatic residue); S(=O)$_2$—O(C$_{3-6}$-cycloaliphatic residue); S(=O)$_2$—O(3 to 7 membered heterocyclic residue); S(=O)$_2$—O(aryl); S(=O)$_2$—O(heteroaryl); S(=O)$_2$—N(H)(C$_{1-8}$-aliphatic residue); S(=O)$_2$—N(H)(C$_{3-6}$-cycloaliphatic residue); S(=O)$_2$—N(H)(3 to 7 membered heterocyclic residue); S(=O)$_2$—N(H)(aryl); S(=O)$_2$—N(H)(heteroaryl); S(=O)$_2$—N(C$_{1-8}$-aliphatic residue)(C$_{1-8}$-aliphatic residue); S(=O)$_2$—N(C$_{1-8}$-aliphatic residue)(C$_{3-6}$-cycloaliphatic residue); S(=O)$_2$—N(C$_{1-8}$-aliphatic residue)(3 to 7 membered heterocyclic residue); S(=O)$_2$—N(C$_{1-8}$-aliphatic residue)(aryl); S(=O)$_2$—N(C$_{1-8}$-aliphatic residue)(heteroaryl);

in which "mono- or polysubstituted" with respect to "aryl" and "heteroaryl" relates, with respect to the corresponding residues, in each case independently of one another, to the substitution of one or more hydrogen atoms each independently of one another by at least one substituent selected from the group consisting of F; Cl; Br; NO$_2$; CN; CF$_3$; CF$_2$H; CFH$_2$; CF$_2$Cl; CFCl$_2$; C$_{1-8}$-aliphatic residue; C$_{3-6}$-cycloaliphatic residue; 3 to 7 membered heterocyclic residue; aryl; heteroaryl; aryl, heteroaryl, CO$_{3-6}$-cycloaliphatic residue or 3 to 6 membered heterocycloaliphatic, each connected via a C$_{1-4}$-aliphatic group; C(=O)H; C(=O)—(C$_{1-8}$-aliphatic residue); C(=O)—(C$_{3-6}$-cycloaliphatic residue); C(=O)-(3 to 7 membered heterocyclic residue); C(=O)-(aryl); C(=O)-(heteroaryl); C(=O)OH; C(=O)—O(C$_{1-8}$-aliphatic residue); C(=O)—O(C$_{3-6}$-cycloaliphatic residue); C(=O)—O(3 to 7 membered heterocyclic residue); C(=O)—O(aryl); C(=O)—O(heteroaryl); C(=O)—NH$_2$; C(=O)—N(H)(C$_{1-8}$-aliphatic residue); C(=O)—N(H)(C$_{3-6}$-cycloaliphatic residue); C(=O)—N(H)(3 to 7 membered heterocyclic residue); C(=O)—N(H)(aryl); C(=O)—N(H)(heteroaryl); C(=O)—N(C$_{1-8}$-aliphatic residue)(C$_{1-8}$-aliphatic residue); C(=O)—N(C$_{1-8}$-aliphatic residue)(C$_{3-6}$-cycloaliphatic residue); C(=O)—N(C$_{1-8}$-aliphatic residue)(3 to 7 membered heterocyclic residue); C(=O)—N(C$_{1-8}$-aliphatic residue)(aryl); C(=O)—N(C$_{1-8}$-aliphatic residue)(heteroaryl); OH; =O; O—(C$_{1-8}$-aliphatic residue); O—(C$_{3-6}$-cycloaliphatic residue); O-(3 to 7 membered heterocyclic residue); O-(aryl); O-(heteroaryl); OCF$_3$; OCF$_2$H; OCFH$_2$; OCF$_2$Cl; OCFCl$_2$; O—(C$_{2-4}$-aliphatic group)-OH; O—(C$_{2-4}$-aliphatic group)-O(C$_{1-8}$-aliphatic residue); O—C(=O)—(C$_{1-8}$-aliphatic residue); O—C(=O)—(C$_{3-6}$-cycloaliphatic residue); O—C(=O)-(3 to 7 membered heterocyclic residue); O—C(=O)-(aryl); C(=O)-(heteroaryl); O—C(=O)—NH$_2$; O—C(=O)—N(H)(C$_{1-8}$-aliphatic residue); O—C(=O)—N(H)(C$_{3-6}$-cycloaliphatic residue); O—C(=O)—N(H)(3 to 7 membered heterocyclic residue); O—C(=O)—N(H)(aryl); O—C(=O)—N(H)(heteroaryl); O—C(=O)—N(C$_{1-8}$-aliphatic residue)(C$_{1-8}$-aliphatic residue); O—C(=O)—N(C$_{1-8}$-aliphatic residue)(C$_{3-6}$-cycloaliphatic residue); O—C(=O)—N(C$_{1-8}$-aliphatic residue) (3 to 7 membered heterocyclic residue); O—C(=O)—N(C$_{1-8}$-aliphatic residue)(aryl); O—C(=O)—N(C$_{1-8}$-aliphatic residue)(heteroaryl); NH$_2$; N(H)(C$_{1-8}$-aliphatic residue); N(H)(C$_{3-6}$-cycloaliphatic residue); N(H)(3 to 7 membered heterocyclic residue); N(H)(aryl); N(H)(heteroaryl); N(C$_{1-8}$-aliphatic residue)(C$_{1-8}$-aliphatic residue); N(C$_{1-8}$-aliphatic residue)(C$_{3-6}$-cycloaliphatic residue); N(C$_{1-8}$-aliphatic residue)(3 to 7 membered heterocyclic residue); N(C$_{1-8}$-aliphatic residue)(aryl); N(C$_{1-8}$-aliphatic residue)(heteroaryl); N(H)—C(=O)—(C$_{1-8}$-aliphatic residue); N(H)—C(=O)—(C$_{3-6}$-cycloaliphatic residue); N(H)—C(=O)-(3 to 7 membered heterocyclic residue); N(H)—C(=O)-(aryl); N(H)—C(=O)-(heteroaryl); N(C$_{1-8}$-aliphatic residue)-C(=O)—(C$_{1-8}$-aliphatic residue); N(C$_{1-8}$-aliphatic residue)-C(=O)—(C$_{3-6}$-cycloaliphatic residue); N(C$_{1-8}$-aliphatic residue)-C(=O)-(3 to 7 membered heterocyclic residue); N(C$_{1-8}$-aliphatic residue)-C(=O)-(aryl); N(C$_{1-8}$-aliphatic residue)-C(=O)-(heteroaryl); N(H)—S(=O)$_2$—(C$_{1-8}$-aliphatic residue); N(H)—S(=O)$_2$—(C$_{3-6}$-cycloaliphatic residue); N(H)—S(=O)$_2$-(3 to 7 membered heterocyclic residue); N(H)—S(=O)$_2$-(aryl); N(H)—S(=O)$_2$-(heteroaryl); N(C$_{1-8}$-aliphatic residue)-S(=O)$_2$—(C$_{1-8}$-aliphatic residue); N(C$_{1-8}$-aliphatic residue)-S(=O)$_2$—(C$_{3-6}$-cycloaliphatic residue); N(C$_{1-8}$-aliphatic residue)-S(=O)$_2$-(3 to 7 membered heterocyclic residue); N(C$_{1-8}$-aliphatic residue)-S(=O)$_2$-(aryl); N(C$_{1-8}$-aliphatic residue)-S(=O)$_2$-(heteroaryl); N(H)—C(=O)—O(C$_{1-8}$-aliphatic residue); N(H)—C(=O)—O(C$_{3-6}$-cycloaliphatic residue); N(H)—C(=O)—O(3 to 7 membered heterocyclic residue); N(H)—C(=O)—O(aryl); N(H)—C(=O)—O(heteroaryl); N(C$_{1-8}$-aliphatic residue)-C(=O)—O(C$_{1-8}$-aliphatic residue); N(C$_{1-8}$-aliphatic residue)-C(=O)—O(C$_{3-6}$-cycloaliphatic residue); N(C$_{1-8}$-aliphatic residue)-C(=O)—O(3 to 7 membered heterocyclic residue); N(C$_{1-8}$-aliphatic residue)-C(=O)—O(aryl); N(C$_{1-8}$-aliphatic residue)-C(=O)—O(heteroaryl); N(H)—C(=O)—NH$_2$; N(H)—C(=O)—N(H)(C$_{1-8}$-aliphatic residue); N(H)—C(=O)—N(H)(C$_{3-6}$-cycloaliphatic residue); N(H)—C(=O)—N(H)(3 to 7 membered heterocyclic residue); N(H)—C(=O)—N(H)(aryl); N(H)—C(=O)—N(H)(heteroaryl); N(C$_{1-8}$-aliphatic residue)-C(=O)—NH$_2$; N(C$_{1-8}$-aliphatic residue)-

C(=O)—N(H)($C_{1-8}$-aliphatic residue); N($C_{1-8}$-aliphatic residue)-C(=O)—N(H)($C_{3-6}$-cycloaliphatic residue); N($C_{1-8}$-aliphatic residue)-C(=O)—N(H)(3 to 7 membered heterocyclic residue); N($C_{1-8}$-aliphatic residue)-C(=O)—N(H)(aryl); N($C_{1-8}$-aliphatic residue)-C(=O)—N(H)(heteroaryl); N(H)—C(=O)—N($C_{1-8}$-aliphatic residue)($C_{1-8}$-aliphatic residue); N(H)—C(=O)—N($C_{1-8}$-aliphatic residue)($C_{3-6}$-cycloaliphatic residue); N(H)—C(=O)—N($C_{1-8}$-aliphatic residue)(3 to 7 membered heterocyclic residue); N(H)—C(=O)—N($C_{1-8}$-aliphatic residue)(aryl); N(H)—C(=O)—N($C_{1-8}$-aliphatic residue) (heteroaryl); N($C_{1-8}$-aliphatic residue)-C(=O)—N($C_{1-8}$-aliphatic residue) ($C_{1-8}$-aliphatic residue); N($C_{1-8}$-aliphatic residue)-C(=O)—N($C_{1-8}$-aliphatic residue) ($C_{3-6}$-cycloaliphatic residue); N($C_{1-8}$-aliphatic residue)-C(=O)—N($C_{1-8}$-aliphatic residue)(3 to 7 membered heterocyclic residue); N($C_{1-8}$-aliphatic residue)-C(=O)—N ($C_{1-8}$-aliphatic residue)(aryl); N($C_{1-8}$-aliphatic residue)-C(=O)—N($C_{1-8}$-aliphatic residue) heteroaryl); SH; S—($C_{1-8}$-aliphatic residue); S—($C_{3-6}$-cycloaliphatic residue); S-(3 to 7 membered heterocyclic residue); S-(aryl); S-(heteroaryl); $SCF_3$; $S(=O)_2OH$; S(=O)—($C_{1-8}$-aliphatic residue); S(=O)—($C_{3-6}$-cycloaliphatic residue); S(=O)-(3 to 7 membered heterocyclic residue); S(=O)-(aryl); S(=O)-(heteroaryl); $S(=O)_2$—($C_{1-8}$-aliphatic residue); $S(=O)_2$—($C_{3-6}$-cycloaliphatic residue); $S(=O)_2$-(3 to 7 membered heterocyclic residue); $S(=O)_2$-(aryl); $S(=O)_2$-(heteroaryl); $S(=O)_2$—O($C_{1-8}$-aliphatic residue); $S(=O)_2$—O($C_{3-6}$-cycloaliphatic residue); $S(=O)_2$—O(3 to 7 membered heterocyclic residue); $S(=O)_2$—O(aryl); $S(=O)_2$—O(heteroaryl); $S(=O)_2$—N(H)($C_{1-8}$-aliphatic residue); $S(=O)_2$—N(H)($C_{3-6}$-cycloaliphatic residue); $S(=O)_2$—N(H)(3 to 7 membered heterocyclic residue); $S(=O)_2$—N(H)(aryl); $S(=O)_2$—N(H)(heteroaryl); $S(=O)_2$—N($C_{1-8}$-aliphatic residue) ($C_{1-8}$-aliphatic residue); $S(=O)_2$—N($C_{1-8}$-aliphatic residue)($C_{3-6}$-cycloaliphatic residue); $S(=O)_2$—N($C_{1-8}$-aliphatic residue)(3 to 7 membered heterocyclic residue); $S(=O)_2$—N($C_{1-8}$-aliphatic residue)(aryl); $S(=O)_2$—N ($C_{1-8}$-aliphatic residue)(heteroaryl);
optionally in the form of a single stereoisomer or a mixture of stereoisomers, in the form of the free compound and/or a physiologically acceptable salt and/or a physiologically acceptable solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The term "physiologically acceptable salt" preferably comprises in the sense of this invention a salt of at least one compound according to the present invention and at least one physiologically acceptable acid or base.

A physiologically acceptable salt of at least one compound according to the present invention and at least one physiologically acceptable acid preferably refers in the sense of this invention to a salt of at least one compound according to the present invention with at least one inorganic or organic acid which is physiologically acceptable—in particular when used in human beings and/or other mammals.

A physiologically acceptable salt of at least one compound according to the present invention and at least one physiologically acceptable base preferably refers in the sense of this invention to a salt of at least one compound according to the present invention as an anion with at least one preferably inorganic cation, which is physiologically acceptable—in particular when used in human beings and/or other mammals.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

The terms "$C_{1-8}$-aliphatic residue" and "$C_{1-4}$-aliphatic residue" comprise in the sense of this invention acyclic saturated or unsaturated aliphatic hydrocarbon residues, which can be branched or unbranched and also unsubstituted or mono- or polysubstituted, which contain 1 to 8 or 1 to 4 carbon atoms respectively, i.e. $C_{1-8}$-alkanyls ($C_{1-8}$-alkyls), $C_{2-8}$-alkenyls and $C_{2-8}$-alkynyls as well as $C_{1-4}$-alkanyls ($C_{1-4}$-alkyls), $C_{2-4}$-alkenyls and $C_{2-4}$-alkynyls, respectively. Alkenyls comprise at least one C—C-double bond (a C=C-bond) and alkynyls comprise at least one C—C triple bond (a C—C-bond). Preferably, aliphatic residues are selected from the group consisting of alkanyl (alkyl) and alkenyl residues, more preferably are alkanyl (alkyl) residues. Hence, preferred "$C_{1-8}$-aliphatic residue" is "$C_{1-8}$-alkyl" and preferred "$C_{1-4}$-aliphatic residue" is "$C_{1-4}$-alkyl". Preferred $C_{1-8}$-alkyl residues are selected from the group consisting of methyl, ethyl, n-propyl, 2-propyl, n-butyl, isobutyl, sec.-butyl, tert.-butyl, n-pentyl, isopentyl, neopentyl, n-hexyl, n-heptyl and n-octyl. Preferred $C_{1-4}$-alkyl residues are selected from the group consisting of methyl, ethyl, n-propyl, 2-propyl, n-butyl, isobutyl, sec.-butyl and tert.-butyl. Preferred $C_{2-8}$-alkenyl residues are selected from the group consisting of ethenyl (vinyl), propenyl (—$CH_2$CH=$CH_2$, —CH=$CHCH_3$, —C(=$CH_2$)$CH_3$), butenyl, pentenyl, hexenyl heptenyl and octenyl. Preferred $C_{2-4}$ alkenyl residues are selected from the group consisting of ethenyl (vinyl), propenyl (—$CH_2$CH=$CH_2$, —CH=$CHCH_3$, —C(=$CH_2$)$CH_3$) and butenyl. Preferred $C_{2-8}$ alkynyl residues are selected from the group consisting of ethynyl, propynyl (—$CH_2$C≡CH, —C≡$CCH_3$), butynyl, pentynyl, hexynyl, heptynyl and octynyl. Preferred $C_{2-4}$-alkynyl residues are selected from the group consisting of ethynyl, propynyl (—$CH_2$C≡CH, —C≡$CCH_3$) and butynyl.

The term "$C_{3-6}$-cycloaliphatic residue" means for the purposes of this invention cyclic aliphatic hydro-carbons containing 3, 4, 5 or 6 carbon atoms, wherein the hydrocarbons in each case can be saturated or unsaturated (but not aromatic), unsubstituted or mono- or polysubstituted. The cycloaliphatic residues can be bound to the respective superordinate general structure via any desired and possible ring member of the cycloaliphatic residue. The cycloaliphatic residues can also be condensed with further saturated, (partially) unsaturated, (hetero)cyclic, aromatic or heteroaromatic ring systems, i.e. with cycloaliphatic, heterocycloaliphatic, aryl or heteroaryl residues, which in each case can in turn be unsubstituted or mono- or polysubstituted. Preferred $C_{3-6}$-cycloaliphatic residues are selected from the group consisting of cyclopropyl, cyclobutyl, cyclopentyl, cyclohexyl, cyclopentenyl and cyclohexenyl, in particular cyclopropyl.

The terms "3 to 7 membered heterocycloaliphatic residue" or "3-7-membered heterocycloaliphatic residue", mean for the purposes of this invention heterocycloaliphatic saturated or unsaturated (but not aromatic) residues having 3 to 6, i.e. 3, 4, 5 or 6 ring members, in which in each case at least one, if appropriate also two, three or four carbon atoms are replaced by a heteroatom or a heteroatom group each selected independently of one another from the group consisting of O, S, S(=O), $S(=O)_2$, N, NH and N($C_{1-6}$-alkyl) such as N($CH_3$), wherein the ring members can be unsubstituted or mono- or poly-substituted. The 3 to 7 membered heterocycloaliphatic residue residues can also be condensed with further saturated, (partially) unsaturated, (hetero)cyclic, aromatic or heteroaromatic ring systems, i.e. with cycloaliphatic, heterocycloaliphatic, aryl or heteroaryl residues, which in each case can in turn be unsubstituted or mono- or polysubstituted. The heterocycloaliphatic residue can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted, wherein the aryl substituents can be the same or different and in any desired and possible position of the aryl. The aryl can be bound to the superordinate general structure via any desired and possible ring member of the aryl residue. The aryl residues can also be condensed with further saturated, (partially) unsaturated, (hetero)cycloaliphatic, aromatic or heteroaromatic ring systems, i.e. with a cycloaliphatic, heterocycloaliphatic, aryl or heteroaryl residue, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5 or 6-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 14 ring members, wherein the ring system can be formed with further saturated, (partially) unsaturated, (hetero)cycloaliphatic or aromatic or heteroaromatic rings, i.e. with a cycloaliphatic, heterocycloaliphatic, aryl or heteroaryl residue, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

The term "connected via a $C_{1-4}$-aliphatic group" with respect to residues as aryl, heteroaryl, heterocycloaliphatic residue and-cycloaliphatic residue mean for the purpose of the invention that these residues have the above-defined meanings and that each of these residues is bound to the respective superordinate general structure via a $C_{1-4}$-aliphatic group. The $C_{1-4}$-aliphatic group can in all cases be branched or unbranched, unsubstituted or mono- or polysubstituted. The $C_{1-4}$-aliphatic group can in all cases be furthermore saturated or unsaturated, i.e. can be a $C_{1-4}$-alkylene group, a $C_{2-4}$-alkenylene group or a $C_{2-4}$-alkynylene group. Preferably, the $C_{1-4}$-aliphatic group is a $C_{1-4}$-alkylene group or a $C_{2-4}$-alkenylene group, more preferably a $C_{1-4}$-alkylene group. Preferred $C_{1-4}$-alkylene groups are selected from the group consisting of —$CH_2$—, —$CH_2CH_2$—, —$CH(CH_3)$—, —$CH_2CH_2CH_2$—, —$CH(CH_3)CH_2$—, —$CH(CH_2CH_3)$—, —$CH_2(CH_2)_2CH_2$—, —$CH(CH_3)CH_2CH_2$—, —$CH_2CH(CH_3)CH_2$—, —$CH(CH_3)CH(CH_3)$—, —$CH(CH_2CH_3)CH_2$—, —$C(CH_3)_2$—$CH_2$—, —$CH(CH_2CH_2CH_3)$— and —$C(CH_3)(CH_2CH_3)$—. Preferred $C_{2-4}$-alkenylene groups are selected from the group consisting of —CH=CH—, —CH=CHCH$_2$—, —C(CH$_3$)=CH$_2$—, —CH=CHCH$_2$CH$_2$—, —CH$_2$CH=CHCH$_2$—, —CH=CHCH=CH—, —C(CH$_3$)=CHCH$_2$—, —CH=C(CH$_3$)CH$_2$—, —C(CH$_3$)=C(CH$_3$)— and —C(CH$_2$CH$_3$)=CH—.

Preferred $C_{2-4}$-alkynylene groups are selected from the group consisting of —C≡C—, —C≡C—CH$_2$—, —C≡C—CH$_2$—CH$_2$—, —C≡CCH(CH$_3$)—, —CH$_2$—C≡C—H$_2$— and —C≡C—C≡C—.

The term "$C_{2-4}$-aliphatic group" with respect to substituents such as "NH—($C_{2-4}$-aliphatic group)-OH" and the like means for the purpose of the invention that the $C_{2-4}$-aliphatic group reflects a spacer between two structural elements of the substituent and that each of the structural elements are bound to each other via a $C_{2-4}$-aliphatic group. The $C_{2-4}$-aliphatic group can in all cases, if structurally possible, be branched or unbranched, unsubstituted or mono- or polysubstituted. The $C_{2-4}$-aliphatic group can in all cases be furthermore saturated or unsaturated, i.e. can be a $C_{2-4}$-alkylene group, a $C_{2-4}$-alkenylene group or a $C_{2-4}$-alkynylene group. Preferably, the $C_{2-4}$-aliphatic group is a $C_{2-4}$-alkylene group or a $C_{2-4}$-alkenylene group, more preferably a $C_{2-4}$-alkylene group. Preferred $C_{2-4}$-alkylene groups are selected from the group consisting of —CH$_2$—CH$_2$—, —CH$_2$—CH$_2$—CH$_2$—, —CH(CH$_3$)—CH$_2$—, —CH$_2$—CH(CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —CH$_2$—CH(CH$_2$CH$_3$)—, —C(CH$_3$)$_2$—CH$_2$— and —CH$_2$—C(CH$_3$)$_2$—. Preferred $C_{2-4}$-alkenylene groups are selected from the group consisting of —CH=CH—, —CH=CHCH$_2$—, —C(CH$_3$)=CH$_2$—, —CH=CHCH$_2$CH$_2$—, —CH$_2$—CH=CHCH$_2$, —CH=CHCH=CH—, —C(CH$_3$)=CHCH$_2$—, —CH=C(CH$_3$)CH$_2$—, —C(CH$_3$)=C(CH$_3$)— and —C(CH$_2$CH$_3$)=CH—. Preferred $C_{2-4}$-alkynylene groups are selected from the group consisting of —C≡C—, —C≡C—CH$_2$—, —C≡C—CH$_2$—CH$_2$—, —C≡CCH(CH$_3$)—, —CH$_2$—C≡C—CH$_2$— and —C≡C—C≡C—.

In relation to the terms "aliphatic residue" and "aliphatic group", in particular "alkyl" and "alkylene", as well as "aliphatic group", "cycloaliphatic residue" and "heterocycloaliphatic residue", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; CN; CF$_3$; CF$_2$H; CFH$_2$; CF$_2$Cl; CFCl$_2$; $C_{1-8}$-aliphatic residue; $C_{3-6}$-cycloaliphatic residue; 3 to 7 membered heterocyclic residue; aryl; heteroaryl; aryl, heteroaryl, $C_{3-6}$-cycloaliphatic residue or 3 to 6 membered heterocycloaliphatic, each connected via a $C_{1-4}$-aliphatic group; C(=O)—($C_{1-8}$-aliphatic residue); C(=O)—($C_{3-6}$-cycloaliphatic residue); C(=O)-(3 to 7 membered heterocyclic residue); C(=O)-(aryl); C(=O)-(heteroaryl); C(=O)OH; C(=O)—O($C_{1-8}$-aliphatic residue); C(=O)—O($C_{3-6}$-cycloaliphatic residue); C(=O)—O(3 to 7 membered heterocyclic residue); C(=O)—O(aryl); C(=O)—O(heteroaryl); C(=O)—$NH_2$; C(=O)—N(H)($C_{1-8}$-aliphatic residue); C(=O)—N(H)($C_{3-6}$-cycloaliphatic residue);

C(=O)—N(H)(3 to 7 membered heterocyclic residue); C(=O)—N(H)(aryl); C(=O)—N(H)(heteroaryl); C(=O)—N($C_{1-8}$-aliphatic residue)($C_{1-8}$-aliphatic residue); C(=O)—N($C_{1-8}$-aliphatic residue)($C_{3-6}$-cycloaliphatic residue); C(=O)—N($C_{1-8}$-aliphatic residue)(3 to 7 membered heterocyclic residue); C(=O)—N($C_{1-8}$-aliphatic residue)(aryl); C(=O)—N($C_{1-8}$-aliphatic residue) (heteroaryl); OH; =O; O—($C_{1-8}$-aliphatic residue); O—($C_{3-6}$-cycloaliphatic residue); O-(3 to 7 membered heterocyclic residue); O-(aryl); O-(heteroaryl); $OCF_3$; $OCF_2H$; $OCFH_2$; $OCF_2Cl$; $OCFCl_2$; O—($C_{2-4}$-aliphatic group)-OH; O—($C_{2-4}$-aliphatic group)-O($C_{1-8}$-aliphatic residue); O—C(=O)—($C_{1-8}$-aliphatic residue); O—C(=O)—($C_{3-6}$-cycloaliphatic residue); O—C(=O)-(3 to 7 membered heterocyclic residue); O—C(=O)-(aryl); O—C(=O)-(heteroaryl); O—C(=O)—$NH_2$; O—C(=O)—N(H)($C_{1-8}$-aliphatic residue); O—C(=O)—N(H)($C_{3-6}$-cycloaliphatic residue); O—C(=O)—N(H)(3 to 7 membered heterocyclic residue); O—C(=O)—N(H)(aryl); O—C(=O)—N(H)(heteroaryl); O—C(=O)—N($C_{1-8}$-aliphatic residue)($C_{1-8}$-aliphatic residue); O—C(=O)—N($C_{1-8}$-aliphatic residue)($C_{3-6}$-cycloaliphatic residue); O—C(=O)—N($C_{1-8}$-aliphatic residue)(3 to 7 membered heterocyclic residue); O—C(=O)—N($C_{1-8}$-aliphatic residue)(aryl); O—C(=O)—N($C_{1-8}$-aliphatic residue)(heteroaryl); $NH_2$; N(H)($C_{1-8}$-aliphatic residue); N(H)($C_{3-6}$-cycloaliphatic residue); N(H)(3 to 7 membered heterocyclic residue); N(H)(aryl); N(H)(heteroaryl); N($C_{1-8}$-aliphatic residue)($C_{1-8}$-aliphatic residue); N($C_{1-8}$-aliphatic residue)($C_{3-6}$-cycloaliphatic residue); N($C_{1-8}$-aliphatic residue)(3 to 7 membered heterocyclic residue); N($C_{1-8}$-aliphatic residue)(aryl); N($C_{1-8}$-aliphatic residue)(heteroaryl); N(H)—C(=O)—($C_{1-8}$-aliphatic residue); N(H)—C(=O)—($C_{3-6}$-cycloaliphatic residue); N(H)—C(=O)-(3 to 7 membered heterocyclic residue); N(H)—C(=O)-(aryl); N(H)—C(=O)-(heteroaryl); N($C_{1-8}$-aliphatic residue)-C(=O)—($C_{1-8}$-aliphatic residue); N($C_{1-8}$-aliphatic residue)-C(=O)—($C_{3-6}$-cycloaliphatic residue); N($C_{1-8}$-aliphatic residue)-C(=O)-(3 to 7 membered heterocyclic residue); N($C_{1-8}$-aliphatic residue)-C(=O)-(aryl); N($C_{1-8}$-aliphatic residue)-C(=O)-(heteroaryl); N(H)—S(=O)$_2$—($C_{1-8}$-aliphatic residue); N(H)—S(=O)$_2$—($C_{3-6}$-cycloaliphatic residue); N(H)—S(=O)$_2$-(3 to 7 membered heterocyclic residue); N(H)—S(=O)$_2$-(aryl); N(H)—S(=O)$_2$-(heteroaryl); N($C_{1-8}$-aliphatic residue)-S(=O)$_2$—($C_{1-8}$-aliphatic residue); N($C_{1-8}$-aliphatic residue)-S(=O)$_2$—($C_{3-6}$-cycloaliphatic residue); N($C_{1-8}$-aliphatic residue)-S(=O)$_2$-(3 to 7 membered heterocyclic residue); N($C_{1-8}$-aliphatic residue)-S(=O)$_2$-(aryl); N($C_{1-8}$-aliphatic residue)-S(=O)$_2$-(heteroaryl); N(H)—C(=O)—O($C_{1-8}$-aliphatic residue); N(H)—C(=O)—O($C_{3-6}$-cycloaliphatic residue); N(H)—C(=O)—O(3 to 7 membered heterocyclic residue); N(H)—C(=O)—O(aryl); N(H)—C(=O)—O(heteroaryl); N($C_{1-8}$-aliphatic residue)-C(=O)—O($C_{1-8}$-aliphatic residue); N($C_{1-8}$-aliphatic residue)-C(=O)—O($C_{3-6}$-cycloaliphatic residue); N($C_{1-8}$-aliphatic residue)-C(=O)—O(3 to 7 membered heterocyclic residue); N($C_{1-8}$-aliphatic residue)-C(=O)—O(aryl); N($C_{1-8}$-aliphatic residue)-C(=O)—O(heteroaryl); N(H)—C(=O)—$NH_2$; N(H)—C(=O)—N(H)($C_{1-8}$-aliphatic residue); N(H)—C(=O)—N(H)($C_{3-6}$-cycloaliphatic residue); N(H)—C(=O)—N(H)(3 to 7 membered heterocyclic residue); N(H)—C(=O)—N(H)(aryl); N(H)—C(=O)—N(H)(heteroaryl); N($C_{1-8}$-aliphatic residue)-C(=O)—$NH_2$; N($C_{1-8}$-aliphatic residue)-C(=O)—N(H)($C_{1-8}$-aliphatic residue); N($C_{1-8}$-aliphatic residue)-C(=O)—N(H)($C_{3-6}$-cycloaliphatic residue); N($C_{1-8}$-aliphatic residue)-C(=O)—N(H)(3 to 7 membered heterocyclic residue); N($C_{1-8}$-aliphatic residue)-C(=O)—N(H)(aryl); N($C_{1-8}$-aliphatic residue)-C(=O)—N(H)(heteroaryl); N(H)—C(=O)—N($C_{1-8}$-aliphatic residue)($C_{1-8}$-aliphatic residue); N(H)—C(=O)—N($C_{1-8}$-aliphatic residue)($C_{3-6}$-cycloaliphatic residue); N(H)—C(=O)—N($C_{1-8}$-aliphatic residue)(3 to 7 membered heterocyclic residue); N(H)—C(=O)—N($C_{1-8}$-aliphatic residue)(aryl); N(H)—C(=O)—N($C_{1-8}$-aliphatic residue)(heteroaryl); N($C_{1-8}$-aliphatic residue)-C(=O)—N($C_{1-8}$-aliphatic residue)($C_{1-8}$-aliphatic residue); N($C_{1-8}$-aliphatic residue)-C(=O)—N($C_{1-8}$-aliphatic residue)($C_{3-6}$-cycloaliphatic residue); N($C_{1-8}$-aliphatic residue)-C(=O)—N($C_{1-8}$-aliphatic residue)(3 to 7 membered heterocyclic residue); N($C_{1-8}$-aliphatic residue)-C(=O)—N($C_{1-8}$-aliphatic residue)(aryl); N($C_{1-8}$-aliphatic residue)-C(=O)—N($C_{1-8}$-aliphatic residue)(heteroaryl); S—($C_{3-6}$-cycloaliphatic residue); S-(3 to 7 membered heterocyclic residue); S-(aryl); S-(heteroaryl); $SCF_3$; S(=O)$_2$OH; S(=O)—($C_{1-8}$-aliphatic residue); S(=O)—($C_{3-6}$-cycloaliphatic residue); S(=O)-(3 to 7 membered heterocyclic residue); S(=O)-(aryl); S(=O)-(heteroaryl); S(=O)$_2$—($C_{1-8}$-aliphatic residue); S(=O)$_2$—($C_{3-6}$-cycloaliphatic residue); S(=O)$_2$-(3 to 7 membered heterocyclic residue); S(=O)$_2$-(aryl); S(=O)$_2$-(heteroaryl); S(=O)$_2$—O($C_{1-8}$-aliphatic residue); S(=O)$_2$—O($C_{3-6}$-cycloaliphatic residue); S(=O)$_2$—O(3 to 7 membered heterocyclic residue); S(=O)$_2$—O(aryl); S(=O)$_2$—O(heteroaryl); S(=O)$_2$—N(H)($C_{1-8}$-aliphatic residue); S(=O)$_2$—N(H)($C_{3-6}$-cycloaliphatic residue); S(=O)$_2$—N(H)(3 to 7 membered heterocyclic residue); S(=O)$_2$—N(H)(aryl); S(=O)$_2$—N(H)(heteroaryl); S(=O)$_2$—N($C_{1-8}$-aliphatic residue)($C_{1-8}$-aliphatic residue); S(=O)$_2$—N($C_{1-8}$-aliphatic residue)($C_{3-6}$-cycloaliphatic residue); S(=O)$_2$—N($C_{1-8}$-aliphatic residue)(3 to 7 membered heterocyclic residue); S(=O)$_2$—N($C_{1-8}$-aliphatic residue)(aryl); S(=O)$_2$—N($C_{1-8}$-aliphatic residue)(heteroaryl).

The term "polysubstituted" with respect to polysubstituted residues and groups includes the polysubstitution of these residues and groups either on different or on the same atoms, for example trisubstituted on the same carbon atom, as in the case of $CF_3$, $CH_2CF_3$ or 1,1-difluorocyclohexyl, or at various points, as in the case of CH(OH)—CH=CH—$CHC_2$ or 1-chloro-3-fluorocyclohexyl. A substituent can if appropriate for its part in turn be mono- or polysubstituted. The multiple substitution can be carried out using the same or using different substituents.

Preferred substituents of "aliphatic residue" and "aliphatic group", in particular "alkyl" and "alkylene", as well as of "aliphatic group", "cycloaliphatic residue" and "heterocycloaliphatic residue" are selected from the group consisting of F; Cl; CN; =O; $CF_3$; $CF_2H$; $CFH_2$; $CF_2Cl$; $CFCl_2$; $C_{1-4}$-alkyl; ($C_{2-4}$-aliphatic group)-OH; C(=O)—H; C(=O)—$C_{1-4}$-alkyl; C(=O)—OH; C(=O)—O—$C_{1-4}$-alkyl; C(=O)—N(H)(OH); C(=O)—$NH_2$; C(=O)—N(H)($C_{1-4}$-alkyl); C(=O)—N($C_{1-4}$-alkyl)$_2$; OH; $OCF_3$; $OCF_2H$; $OCFH_2$; $OCF_2Cl$; $OCFCl_2$; O—$C_{1-4}$-alkyl; O—($C_{2-4}$-aliphatic group)-OH; O—($C_{2-4}$-aliphatic group)-O—$C_{1-4}$- alkyl; O—C(=O)—C$_{1-4}$-alkyl; O—C(=O)—O—C$_{1-4}$-alkyl; O—(C=O)—N(H)(C$_{1-4}$-alkyl); O—C(=O)—N(C$_{1-4}$-alkyl)$_2$; O—S(=O)$_2$—C$_{1-4}$-alkyl; O—S(=O)$_2$—OH; O—S(=O)$_2$—O—C$_{1-4}$-alkyl; O—S(=O)$_2$—NH$_2$; O—S(=O)$_2$—N(H)(C$_{1-4}$-alkyl); O—S(=O)$_2$—N(C$_{1-4}$-alkyl)$_2$; NH$_2$; N(H)(C$_{1-4}$-alkyl); N(C$_{1-4}$-alkyl)$_2$; N(H)—C(=O)—C$_{1-4}$-alkyl; N(H)—C(=O)—O—C$_{1-4}$-alkyl; N(H)—C(=O)—NH$_2$; N(H)—C(=O)—N(H)(C$_{1-4}$-alkyl); N(H)—C(=O)—N(C$_{1-4}$-alkyl)$_2$; N(C$_{1-4}$-alkyl)-C(=O)—C$_{1-4}$-alkyl; N(C$_{1-4}$-alkyl)-C(=O)—O—C$_{1-4}$-alkyl; N(C$_{1-4}$-alkyl)-C(=O)—NH$_2$; N(C$_{1-4}$-alkyl)-C(=O)—N(H)(C$_{1-4}$-alkyl); N(C$_{1-4}$-alkyl)-C(=O)—N(C$_{1-4}$-alkyl)$_2$; N(H)—S(=O)$_2$—OH; N(H)—S(=O)$_2$—C$_{1-4}$-alkyl; N(H)—S(=O)$_2$—O—C$_{1-4}$-alkyl; N(H)—S(=O)$_2$—NH$_2$; N(H)—S(=O)$_2$—N(H)(C$_{1-4}$-alkyl); N(H)—S(=O)$_2$—N(C$_{1-4}$-alkyl)$_2$; N(C$_{1-4}$-alkyl)-S(=O)$_2$—OH; N(C$_{1-4}$-alkyl)-S(=O)$_2$—C$_{1-4}$-alkyl; N(C$_{1-4}$-alkyl)-S(=O)$_2$—O—C$_{1-4}$-alkyl; N(C$_{1-4}$-alkyl)-S(=O)$_2$—NH$_2$; N(C$_{1-4}$-alkyl)-S(=O)$_2$—N(H)(C$_{1-4}$-alkyl); N(C$_{1-4}$-alkyl)-S(=O)$_2$—N(C$_{1-4}$-alkyl)$_2$; SH; SCF$_3$; SCF$_2$H; SCFH$_2$; SCF$_2$Cl; SCFCl$_2$; S—C$_{1-4}$-alkyl; S(=O)—C$_{1-4}$-alkyl; S(=O)$_2$—C$_{1-4}$-alkyl; S(=O)$_2$—OH; S(=O)$_2$—O—C$_{1-4}$-alkyl; S(=O)$_2$—NH$_2$; S(=O)$_2$—N(H)(C$_{1-4}$-alkyl); and S(=O)$_2$—N(C$_{1-4}$-alkyl)$_2$.

Particularly preferred substituents of "aliphatic residue" and "aliphatic group", in particular "alkyl" and "alkylene", as well as of "aliphatic group", "cycloaliphatic residue" and "heterocycloaliphatic residue" are selected from the group consisting of F; Cl; CF$_3$; CN; =O; C$_{1-4}$-alkyl; (C$_{2-4}$-aliphatic group)-OH; C(=O)—H; C(=O)—C$_{1-4}$-alkyl; C(=O)—OH; C(=O)—O—C$_{1-4}$-alkyl; C(=O)—NH$_2$; C(=O)—N(H)(C$_{1-4}$-alkyl); C(=O)—N(C$_{1-4}$-alkyl)$_2$; OH; O—C$_{1-4}$-alkyl; O—C(=O)—C$_{1-4}$-alkyl; O—(C$_{2-4}$-aliphatic group)-OH; O—(C$_{2-4}$-aliphatic group)-O—C$_{1-4}$alkyl; OCF$_3$; NH$_2$; N(H)(C$_{1-4}$-alkyl); N(C$_{1-4}$-alkyl)$_2$; N(H)—C(=O)—C$_{1-4}$-alkyl; N(H)—S(=O)$_2$—C$_{1-4}$-alkyl; N(C$_{1-4}$-alkyl)-S(=O)$_2$—C$_{1-4}$-alkyl; N(H)—C(=O)—NH$_2$; N(H)—C(=O)—N(H)(C$_{1-4}$-alkyl); N(H)—C(=O)—N(C$_{1-4}$-alkyl)$_2$; N(H)—S(=O)$_2$—NH$_2$; N(H)—S(=O)$_2$—N(H)(C$_{1-4}$-alkyl); N(H)—S(=O)$_2$—N(C$_{1-4}$-alkyl)$_2$; N(C$_{1-4}$-alkyl)-S(=O)$_2$—NH$_2$; N(C$_{1-4}$-alkyl)-S(=O)$_2$—N(H)(C$_{1-4}$-alkyl); N(C$_{1-4}$-alkyl)-S(=O)$_2$—N(C$_{1-4}$-alkyl)$_2$; SH; SCF$_3$; S—C$_{1-4}$-alkyl; S(=O)$_2$—C$_{1-4}$-alkyl; S(=O)$_2$OH; S(=O)$_2$O—C$_{1-4}$-alkyl and S(=O)$_2$—NH$_2$; S(=O)$_2$—N(H)(C$_{1-4}$-alkyl); and S(=O)$_2$—N(C$_{1-4}$-alkyl)$_2$.

More preferred substituents of "aliphatic residue" and "aliphatic group", in particular "alkyl" and "alkylene", as well as of "aliphatic group", "cycloaliphatic residue" and "heterocycloaliphatic residue" are selected from the group consisting of F; Cl; CF$_3$; CN; =O; C$_{1-4}$-alkyl; (C$_{2-4}$-aliphatic group)-OH; C(=O)—C$_{1-4}$-alkyl; C(=O)—OH; C(=O)—O—C$_{1-4}$-alkyl; C(=O)—NH$_2$; C(=O)—N(H)(C$_{1-4}$-alkyl); C(=O)—N(C$_{1-4}$-alkyl)$_2$; OH; O—C$_{1-4}$-alkyl; O—C(=O)—C$_{1-4}$-alkyl; O—(C$_{2-4}$-aliphatic group)-OH; O—(C$_{2-4}$-aliphatic group)-O—C$_{1-4}$-alkyl; OCF$_3$; NH$_2$; N(H)(C$_{1-4}$-alkyl); N(C$_{1-4}$-alkyl)$_2$; N(H)—C(=O)—C$_{1-4}$-alkyl; N(H)—S(=O)$_2$—C$_{1-4}$-alkyl; N(C$_{1-4}$-alkyl)-S(=O)$_2$—C$_{1-4}$-alkyl; N(H)—C(=O)—NH$_2$; N(H)—C(=O)—N(H)(C$_{1-4}$-alkyl); N(H)—C(=O)—N(C$_{1-4}$-alkyl)$_2$; N(C$_{1-4}$-alkyl)-S(=O)$_2$—NH$_2$; N(C$_{1-4}$-alkyl)-S(=O)$_2$—N(H)(C$_{1-4}$-alkyl); N(C$_{1-4}$-alkyl)-S(=O)$_2$—N(C$_{1-4}$-alkyl)$_2$; S(=O)$_2$C$_{1-4}$-alkyl; S(=O)$_2$OH; S(=O)$_2$O—C$_{1-4}$-alkyl; S(=O)$_2$—NH$_2$; S(=O)$_2$—N(H)(C$_{1-4}$-alkyl) and S(=O)$_2$—N(C$_{1-4}$-alkyl)$_2$.

Most preferred substituents of "aliphatic residue" and "aliphatic group", in particular "alkyl" and "alkylene" are selected from the group consisting of F; Cl; CF$_3$; C(=O)—OH; C(=O)—NH$_2$; C(=O)—N(H)(C$_{1-4}$-alkyl); C(=O)—N(C$_{1-4}$-alkyl)$_2$; OH; O—C$_{1-4}$-alkyl; O—(C$_{2-4}$-aliphatic group)-OH; O—(C$_{2-4}$-aliphatic group)-O—C$_{1-4}$-alkyl; NH$_2$; N(H)(C$_{1-4}$-alkyl); N(C$_{1-4}$-alkyl)$_2$; N(H)—C(=O)—C$_{1-4}$-alkyl; N(H)—S(=O)$_2$—C$_{1-4}$-alkyl; N(C$_{1-4}$-alkyl)-S(=O)$_2$—C$_{1-4}$-alkyl; N(H)—S(=O)$_2$—NH$_2$; S(=O)$_2$—C$_{1-4}$-alkyl, S(=O)$_2$—NH$_2$, S(=O)$_2$—N(C$_{1-4}$-alkyl)$_2$ and S(=O)$_2$—N(H)(C$_{1-4}$-alkyl).

Particularly preferred substituents of "cycloaliphatic residue" and "heterocycloaliphatic residue" are selected from the group consisting of F; Cl; CF$_3$; CN; =O; C$_{1-4}$-alkyl; CO$_2$H; C(=O)O—C$_{1-4}$-alkyl; CONH$_2$; C(=O)NH—C$_{1-4}$-alkyl; C(=O)N(C$_{1-4}$-alkyl)$_2$; OH; O—C$_{1-4}$-alkyl; OCF$_3$; O—(C$_{2-4}$-aliphatic group)-OH; O—(C$_{2-4}$-aliphatic group)-O—C$_{1-4}$-alkyl; O—C(=O)—C$_{1-4}$-alkyl; NH$_2$; NH—C$_{1-4}$-alkyl; N(C$_{1-4}$-alkyl)$_2$; NH—C(=O)—C$_{1-4}$-alkyl; N(C$_{1-4}$-alkyl)-C(=O)—C$_{1-4}$-alkyl; S(=O)$_2$—C$_{1-4}$-alkyl; S(=O)$_2$—NH$_2$, S(=O)$_2$—N(C$_{1-4}$-alkyl)$_2$ and S(=O)$_2$—N(H)—C$_{1-4}$-alkyl.

In relation to the terms "aryl" and "heteroaryl", the term "mono- or polysubstituted" refers in the sense of this invention, with respect to the corresponding residues or groups, to the single substitution or multiple substitution, e.g. disubstitution, trisubstitution, tetrasubstitution, or pentasubstitution, of one or more hydrogen atoms each independently of one another by at least one substituent selected from the group consisting of F; Cl; Br; NO$_2$; CN; CF$_3$; CF$_2$H; CFH$_2$; CF$_2$Cl; CFCl$_2$; C$_{1-8}$-aliphatic residue; C$_{3-6}$-cycloaliphatic residue; 3 to 7 membered heterocyclic residue; aryl; heteroaryl; aryl, heteroaryl, C$_{3-6}$-cycloaliphatic residue or 3 to 6 membered heterocycloaliphatic, each connected via a C$_{1-4}$-aliphatic group; C(=O)H; C(=O)—(C$_{1-8}$-aliphatic residue); C(=O)—(C$_{3-6}$-cycloaliphatic residue); C(=O)-(3 to 7 membered heterocyclic residue); C(=O)-(aryl); C(=O)-(heteroaryl); C(=O)OH; C(=O)—O(C$_{1-8}$-aliphatic residue); C(=O)—O(C$_{3-6}$-cycloaliphatic residue); C(=O)—O(3 to 7 membered heterocyclic residue); C(=O)—O(aryl); C(=O)—O(heteroaryl); C(=O)—NH$_2$; C(=O)—N(H)(C$_{1-8}$-aliphatic residue); C(=O)—N(H)(C$_{3-6}$-cycloaliphatic residue); C(=O)—N(H)(3 to 7 membered heterocyclic residue); C(=O)—N(H)(aryl); C(=O)—N(H)(heteroaryl); C(=O)—N(C$_{1-8}$-aliphatic residue)(C$_{1-8}$-aliphatic residue); C(=O)—N(C$_{1-8}$-aliphatic residue)(C$_{3-6}$-cycloaliphatic residue); C(=O)—N(C$_{1-8}$-aliphatic residue)(3 to 7 membered heterocyclic residue); C(=O)—N(C$_{1-8}$-aliphatic residue)(aryl); C(=O)—N(C$_{1-8}$-aliphatic residue)(heteroaryl); OH; =O; O—(C$_{1-8}$-aliphatic residue); O—(C$_{3-6}$-cycloaliphatic residue); O -(3 to 7 membered heterocyclic residue); O-(aryl); O-(heteroaryl); OCF$_3$; OCF$_2$H; OCFH$_2$; OCF$_2$Cl; OCFCl$_2$; O—(C$_{2-4}$-aliphatic group)-OH; O—(C$_{2-4}$-aliphatic group)-O(C$_{1-8}$-aliphatic residue); O—C(=O)—(C$_{1-8}$-aliphatic residue); O—C(=O)—(C$_{3-6}$-cycloaliphatic residue); O—C(=O)-(3 to 7 membered heterocyclic residue); O—C(=O)-(aryl); C(=O)-(heteroaryl); O—C(=O)—NH$_2$; O—C(=O)—N(H)(C$_{1-8}$-aliphatic residue); O—C(=O)—N(H)(C$_{3-6}$-cycloaliphatic residue); O—C(=O)—N(H)(3 to 7 membered heterocyclic residue); O—C(=O)—N(H)(aryl); O—C(=O)—N(H)(heteroaryl); O—C(=O)—N(C$_{1-8}$-aliphatic residue)(C$_{1-8}$-aliphatic residue); O—C(=O)—N(C$_{1-8}$-aliphatic residue)(C$_{3-6}$-cycloaliphatic residue); O—C(=O)—N(C$_{1-8}$-aliphatic residue)(3 to 7 membered heterocyclic residue); O—C(=O)—N(C$_{1-8}$-aliphatic residue)(aryl); O—C(=O)—N(C$_{1-8}$-aliphatic residue)(heteroaryl); NH$_2$; N(H)(C$_{1-8}$-aliphatic residue); N(H)(C$_{3-6}$-cycloaliphatic residue); N(H)(3 to 7 membered heterocyclic residue); N(H)(aryl); N(H)(heteroaryl); N($C_{1-8}$-aliphatic residue)($C_{1-8}$-aliphatic residue); N($C_{1-8}$-aliphatic residue)($C_{3-6}$-cycloaliphatic residue); N($C_{1-8}$-aliphatic residue)(3 to 7 membered heterocyclic residue); N($C_{1-8}$-aliphatic residue)(aryl); N($C_{1-8}$-aliphatic residue)(heteroaryl); N(H)—C(=O)—($C_{1-8}$-aliphatic residue); N(H)—C(=O)—($C_{3-6}$-cycloaliphatic residue); N(H)—C(=O)-(3 to 7 membered heterocyclic residue); N(H)—C(=O)-(aryl); N(H)—C(=O)-(heteroaryl); N($C_{1-8}$-aliphatic residue)-C(=O)—($C_{1-8}$-aliphatic residue); N($C_{1-8}$-aliphatic residue)-C(=O)—($C_{3-6}$-cycloaliphatic residue); N($C_{1-8}$-aliphatic residue)-C(=O)-(3 to 7 membered heterocyclic residue); N($C_{1-8}$-aliphatic residue)-C(=O)-(aryl); N($C_{1-8}$-aliphatic residue)-C(=O)-(heteroaryl); N(H)—S(=O)$_2$—($C_{1-8}$-aliphatic residue); N(H)—S(=O)$_2$—($C_{3-6}$-cycloaliphatic residue); N(H)—S(=O)$_2$-(3 to 7 membered heterocyclic residue); N(H)—S(=O)$_2$-(aryl); N(H)—S(=O)$_2$-(heteroaryl); N($C_{1-8}$-aliphatic residue)-S(=O)$_2$—($C_{1-8}$-aliphatic residue); N($C_{1-8}$-aliphatic residue)-S(=O)$_2$—($C_{3-6}$-cycloaliphatic residue); N($C_{1-8}$-aliphatic residue)-S(=O)$_2$-(3 to 7 membered heterocyclic residue); N($C_{1-8}$-aliphatic residue)-S(=O)$_2$-(aryl); N($C_{1-8}$-aliphatic residue)-S(=O)$_2$-(heteroaryl); N(H)—C(=O)—O($C_{1-8}$-aliphatic residue); N(H)—C(=O)—O($C_{3-6}$-cycloaliphatic residue); N(H)—C(=O)—O(3 to 7 membered heterocyclic residue); N(H)—C(=O)—O(aryl); N(H)—C(=O)—O(heteroaryl); N($C_{1-8}$-aliphatic residue)-C(=O)—O($C_{1-8}$-aliphatic residue); N($C_{1-8}$-aliphatic residue)-C(=O)—O($C_{3-6}$-cycloaliphatic residue); N($C_{1-8}$-aliphatic residue)-C(=O)—O(3 to 7 membered heterocyclic residue); N($C_{1-8}$-aliphatic residue)-C(=O)—O(aryl); N($C_{1-8}$-aliphatic residue)-C(=O)—O(heteroaryl); N(H)—C(=O)—NH$_2$; N(H)—C(=O)—N(H)($C_{1-8}$-aliphatic residue); N(H)—C(=O)—N(H)($C_{3-6}$-cycloaliphatic residue); N(H)—C(=O)—N(H)(3 to 7 membered heterocyclic residue); N(H)—C(=O)—N(H)(aryl); N(H)—C(=O)—N(H)(heteroaryl); N($C_{1-8}$-aliphatic residue)-C(=O)—NH$_2$; N($C_{1-8}$-aliphatic residue)-C(=O)—N(H)($C_{1-8}$-aliphatic residue); N($C_{1-8}$-aliphatic residue)-C(=O)—N(H)($C_{3-6}$-cycloaliphatic residue); N($C_{1-8}$-aliphatic residue)-C(=O)—N(H)(3 to 7 membered heterocyclic residue); N($C_{1-8}$-aliphatic residue)-C(=O)—N(H)(aryl); N($C_{1-8}$-aliphatic residue)-C(=O)—N(H)(heteroaryl); N(H)—C(=O)—N($C_{1-8}$-aliphatic residue)($C_{1-8}$-aliphatic residue); N(H)—C(=O)—N($C_{1-8}$-aliphatic residue)($C_{3-6}$-cycloaliphatic residue); N(H)—C(=O)—N($C_{1-8}$-aliphatic residue)(3 to 7 membered heterocyclic residue); N(H)—C(=O)—N($C_{1-8}$-aliphatic residue)(aryl); N(H)—C(=O)—N($C_{1-8}$-aliphatic residue)-(heteroaryl); N($C_{1-8}$-aliphatic residue)-C(=O)—N($C_{1-8}$-aliphatic residue)($C_{1-8}$-aliphatic residue); N($C_{1-8}$-aliphatic residue)-C(=O)—N($C_{1-8}$-aliphatic residue)($C_{3-6}$-cycloaliphatic residue); N($C_{1-8}$-aliphatic residue)-C(=O)—N($C_{1-8}$-aliphatic residue)(3 to 7 membered heterocyclic residue); N($C_{1-8}$-aliphatic residue)-C(=O)—N($C_{1-8}$-aliphatic residue)(aryl); N($C_{1-8}$-aliphatic residue)-C(=O)—N($C_{1-8}$-aliphatic residue) heteroaryl); SH; S—($C_{1-8}$-aliphatic residue); S—($C_{3-6}$-cycloaliphatic residue); S-(3 to 7 membered heterocyclic residue); S-(aryl); S-(heteroaryl); SCF$_3$; S(=O)$_2$OH; S(=O)—($C_{1-8}$-aliphatic residue); S(=O)—($C_{3-6}$-cycloaliphatic residue); S(=O)-(3 to 7 membered heterocyclic residue); S(=O)-(aryl); S(=O)-(heteroaryl); S(=O)$_2$—($C_{1-8}$-aliphatic residue); S(=O)$_2$—($C_{3-6}$-cycloaliphatic residue); S(=O)$_2$-(3 to 7 membered heterocyclic residue); S(=O)$_2$-(aryl); S(=O)$_2$-(heteroaryl); S(=O)$_2$—O($C_{1-8}$-aliphatic residue); S(=O)$_2$—O($C_{3-6}$-cycloaliphatic residue); S(=O)$_2$—O(3 to 7 membered heterocyclic residue); S(=O)$_2$—O(aryl); S(=O)$_2$—O(heteroaryl); S(=O)$_2$—N(H)($C_{1-8}$-aliphatic residue); S(=O)$_2$—N(H)($C_{3-6}$-cycloaliphatic residue); S(=O)$_2$—N(H)(3 to 7 membered heterocyclic residue); S(=O)$_2$—N(H)(aryl); S(=O)$_2$—N(H)(heteroaryl); S(=O)$_2$—N($C_{1-8}$-aliphatic residue)($C_{1-8}$-aliphatic residue); S(=O)$_2$—N($C_{1-8}$-aliphatic residue)($C_{3-6}$-cycloaliphatic residue); S(=O)$_2$—N($C_{1-8}$-aliphatic residue)(3 to 7 membered heterocyclic residue); S(=O)$_2$—N($C_{1-8}$-aliphatic residue)(aryl); S(=O)$_2$—N($C_{1-8}$-aliphatic residue)(heteroaryl).

Preferred substituents of "aryl" and "heteroaryl" are selected from the group consisting of F; Cl; Br; NO$_2$; CN; CF$_3$; CF$_2$H; CFH$_2$; CF$_2$Cl; CFCl$_2$; $C_{1-4}$-alkyl; aryl; heteroaryl; $C_{3-6}$-cycloaliphatic residue; 3 to 6 membered heterocycloaliphatic residue; aryl, heteroaryl, $C_{3-6}$-cycloaliphatic residue or 3 to 6 membered heterocycloaliphatic, each connected via a $C_{1-4}$-aliphatic group; C(=O)—H; C(=O)—$C_{1-4}$-alkyl; C(=O)aryl; C(=O)heteroaryl; C(=O)—OH; C(=O)—O—$C_{1-4}$-alkyl; C(=O)O-aryl; C(=O)O-heteroaryl; CO—NH$_2$; C(=O)—N(H)$C_{1-4}$-alkyl; C(=O)—N($C_{1-4}$-alkyl)$_2$; C(=O)NH-aryl; C(=O)N(aryl)$_2$; C(=O)NH-heteroaryl; C(=O)—N(heteroaryl)$_2$; C(=O)N($C_{1-4}$-alkyl)(aryl); C(=O)N($C_{1-4}$-alkyl)(heteroaryl); C(=O)N(heteroaryl)(aryl); OH; OCF$_3$; OCF$_2$H; OCFH$_2$; OCF$_2$Cl; OCFCl$_2$; O—$C_{1-4}$-alkyl; O—($C_{2-4}$-aliphatic group)-OH; O—($C_{2-4}$-aliphatic group)O—$C_{1-4}$-alkyl; O-benzyl; O-aryl; O-heteroaryl; O—C(=O)—$C_{1-4}$-alkyl; O—C(=O)aryl; O—C(=O)heteroaryl; O—C(=O)—O—$C_{1-4}$-alkyl; O—C(=O)—N(H)$C_{1-4}$-alkyl; O—C(=O)—N($C_{1-4}$-alkyl)$_2$; O—S(=O)$_2$—$C_{1-4}$-alkyl; O—S(=O)$_2$—OH; O—S(=O)$_2$—O—$C_{1-4}$-alkyl; O—S(=O)$_2$—NH$_2$; O—S(=O)$_2$—N(H)$C_{1-4}$-alkyl; O—S(=O)$_2$—N($C_{1-4}$-alkyl)$_2$; NH$_2$; N(H)$C_{1-4}$-alkyl; N($C_{1-4}$-alkyl)$_2$; N(H)—C(=O)—$C_{1-4}$-alkyl; N(H)—C(=O)-aryl; N(H)—C(=O)-heteroaryl; N(H)—C(=O)—O—$C_{1-4}$-alkyl; N(H)—C(=O)—NH$_2$; N(H)—C(=O)—N(H)$C_{1-4}$-alkyl; N(H)—C(=O)—N($C_{1-4}$-alkyl)$_2$; N($C_{1-4}$-alkyl)-C(=O)$C_{1-4}$-alkyl; N($C_{1-4}$-alkyl)-C(=O)—O—$C_{1-4}$-alkyl; N($C_{1-4}$-alkyl)-C(=O)—NH$_2$; N($C_{1-4}$-alkyl)-C(=O)—N(H)$C_{1-4}$-alkyl; N($C_{1-4}$-alkyl)-C(=O)—N($C_{1-4}$-alkyl)$_2$; N(H)—S(=O)$_2$—OH; N(H)—S(=O)$_2$—$C_{1-4}$-alkyl; N(H)—S(=O)$_2$—O—$C_{1-4}$-alkyl; N(H)—S(=O)$_2$—NH$_2$; N(H)—S(=O)$_2$—N(H)$C_{1-4}$-alkyl; N(H)—S(=O)$_2$—N($C_{1-4}$-alkyl)$_2$; N($C_{1-4}$-alkyl)-S(=O)$_2$—OH; N($C_{1-4}$-alkyl)-S(=O)$_2$($C_{1-4}$-alkyl); N($C_{1-4}$-alkyl)-S(=O)$_2$—O($C_{1-4}$-alkyl); N($C_{1-4}$-alkyl)-S(=O)$_2$—NH$_2$; N($C_{1-4}$-alkyl)-S(=O)$_2$—N(H)$C_{1-4}$-alkyl; N($C_{1-4}$-alkyl)-S(=O)$_2$—N($C_{1-4}$-alkyl)$_2$; SH; SCF$_3$; SCF$_2$H; SCFH$_2$; SCF$_2$Cl; SCFCl$_2$; S—$C_{1-4}$-alkyl; S-benzyl; S-aryl; S-heteroaryl; S(=O)—$C_{1-4}$-alkyl; S(=O)$_2$—$C_{1-4}$-alkyl; S(=O)$_2$-aryl; S(=O)$_2$-heteroaryl; S(=O)$_2$—OH; S(=O)$_2$—O$C_{1-4}$-alkyl; S(=O)$_2$O-aryl; S(=O)$_2$O-heteroaryl; S(=O)$_2$—NH$_2$; S(=O)$_2$—N(H)$C_{1-4}$-alkyl, S(=O)$_2$—N(H)-aryl; S(=O)$_2$—N(H)-heteroaryl and S(=O)$_2$—N($C_{1-4}$-alkyl)$_2$.

More preferred substituents of "aryl" and "heteroaryl" are selected from the group consisting of F; Cl; CF$_3$; CN; $C_{1-4}$-alkyl; C(=O)—OH; C(=O)—O—$C_{1-4}$-alkyl; CO—NH$_2$; C(=O)—N(H)$C_{1-4}$-alkyl; C(=O)—N($C_{1-4}$-alkyl)$_2$; OH; O—$C_{1-4}$-alkyl; O—C(=O)—$C_{1-4}$-alkyl; O—($C_{2-4}$-aliphatic group)-OH; O—($C_{2-4}$-aliphatic group)O—$C_{1-4}$-alkyl; OCF$_3$; OCHF$_2$; OCH$_2$F; NH$_2$; N(H)$C_{1-4}$-alkyl; N($C_{1-4}$-alkyl)$_2$; N(H)—C(=O)—$C_{1-4}$-alkyl; N($C_{1-4}$-alkyl)-C(=O)$C_{1-4}$-alkyl; N(H)—S(=O)$_2$—$C_{1-4}$-alkyl; N($C_{1-4}$-alkyl)-S(=O)$_2$($C_{1-4}$-alkyl); N(H)—C(=O)—NH$_2$; N(H)—C(=O)—N(H)$C_{1-4}$-alkyl; N(H)—C(=O)—N($C_{1-4}$-alkyl)$_2$; N($C_{1-4}$-alkyl)-C(=O)—NH$_2$; N($C_{1-4}$-alkyl)-C(=O)—N(H)

$C_{1-4}$-alkyl; $N(C_{1-4}$-alkyl)-C(=O)—N($C_{1-4}$-alkyl)$_2$; S(=O)$_2C_{1-4}$-alkyl; S(=O)$_2$—NH$_2$; S(=O)$_2$—N(H)$C_{1-4}$-alkyl and S(=O)$_2$—N($C_{1-4}$-alkyl)$_2$.

The compounds according to the invention are defined by substituents, for example by $R^A$, $R^B$ and $R^C$ (1$^{st}$ generation substituents) which are for their part if appropriate themselves substituted (2$^{nd}$ generation substituents). Depending on the definition, these substituents of the substituents can for their part be resubstituted (3$^{rd}$ generation substituents). If, for example, $R^A$=a $C_{1-4}$-alkyl (1$^{st}$ generation substituent), then the $C_{1-4}$-alkyl can for its part be substituted, for example with a N(H)$C_{1-4}$-alkyl (2$^{nd}$ generation substituent). This produces the functional group $R^A$=($C_{1-4}$-alkyl-N(H)—$C_{1-4}$-alkyl). The N(H)—$C_{1-4}$-alkyl can then for its part be resubstituted, for example with Cl (3$^{rd}$ generation substituent). Overall, this produces the functional group $R^A$=$C_{1-4}$-alkyl-N(H)—$C_{1-4}$-alkyl-Cl, wherein the $C_{1-4}$-alkyl of the N(H)$C_{1-4}$-alkyl is substituted by Cl.

However, in a preferred embodiment, the 3$^{rd}$ generation substituents may not be resubstituted, i.e. there are then no 4$^{th}$ generation substituents.

In another preferred embodiment, the 2$^{nd}$ generation substituents may not be resubstituted, i.e. there are then not even any 3$^{rd}$ generation substituents. In other words, in this embodiment, in the case of general formula (I), for example, the functional groups for $R^1$ to $R^3$ can each if appropriate be substituted; however, the respective substituents may then for their part not be resubstituted.

In some cases, the compounds according to the invention are defined by substituents which are or carry a-cycloaliphatic residue or a heterocycloaliphatic residue, respectively, in each case unsubstituted or mono- or polysubstituted, or which form together with the carbon atom(s) or heteroatom(s) connecting them, as the ring member or as the ring members, a ring, for example a cycloaliphatic or a heterocycloaliphatic ring system. Both these cycloaliphatic or heterocycloaliphatic ring systems and the (hetero)cycloaliphatic ring systems formed in this manner can if appropriate be condensed with a-cycloaliphatic residue, preferably a $C_{3-6}$-cycloaliphatic residue, or with a heterocycloaliphatic residue, preferably a 3 to 6 membered heterocycloaliphatic residue, e.g. with a-cycloaliphatic residue such as cyclohexyl, or a heterocycloaliphatic residue such as morpholinyl, wherein the cycloaliphatic or heterocycloaliphatic residues condensed in this way can for their part be respectively unsubstituted or mono- or polysubstituted.

Within the scope of the present invention, the symbol

used in the formulae denotes a link of a corresponding residue to the respective superordinate general structure.

If a residue occurs multiply within a molecule, then this residue can have respectively different meanings for various substituents: if, for example, both $R^1$ and $R^2$ denote a 3 to 6 membered heterocycloaliphatic residue, then the 3 to 6 membered heterocycloaliphatic residue can e.g. represent morpholinyl for $R^1$ and can represent piperazinyl for $R^2$.

In one embodiment of the compound according to the present invention, $R^2$ is selected from the group consisting of H; F; Cl; Br; I; NO$_2$; CN; CF$_3$; CF$_2$H; CFH$_2$; $R^{13}$; OH; O—$R^{13}$; NH$_2$; N(H)$R^{13}$; N($R^{13}$)$_2$, wherein $R^{13}$ independently of each other denotes $C_{1-8}$-aliphatic residue, unsubstituted or mono- or polysubstituted; or $C_{3-6}$-cycloaliphatic residue or 3 to 7 membered heterocycloaliphatic residue, in each case unsubstituted or mono- or polysubstituted; or $C_{3-6}$-cycloaliphatic residue or 3 to 7 membered heterocycloaliphatic residue, in each case unsubstituted or mono- or polysubstituted, and in each case connected via a $C_{1-4}$-aliphatic residue, unsubstituted or mono- or polysubstituted.

Preferably, $R^2$ is selected from the group consisting of H; F; Cl; Br; CN; CF$_3$; CF$_2$H; CFH$_2$; $R^{13}$; OH; O—$R^{13}$; NH$_2$; NH—$R^{13}$; N($R^{13}$)$_2$, wherein $R^{13}$ independently of each other denotes $C_{1-8}$-aliphatic residue, unsubstituted or mono- or polysubstituted; or $C_{3-6}$-cycloaliphatic residue or 3 to 7 membered heterocycloaliphatic residue, in each case unsubstituted or mono- or polysubstituted; or $C_{3-6}$-cycloaliphatic residue or 3 to 7 membered heterocycloaliphatic residue, in each case unsubstituted or mono- or polysubstituted, and in each case connected via a $C_{1-4}$-aliphatic residue, unsubstituted or mono- or polysubstituted.

More preferably, $R^2$ is selected from the group consisting of H; F; Cl; Br; CN; CF$_3$; CF$_2$H; CFH$_2$; $R^{13}$; OH; O—$R^{13}$; NH$_2$; NH—$R^{13}$; N($R^{13}$)$_2$, wherein $R^{13}$ independently of each other denotes $C_{1-4}$-aliphatic residue, unsubstituted or mono- or polysubstituted.

Still more preferably, $R^2$ is selected from the group consisting of H; F; Cl, OH, OCH$_3$, NH$_2$, N(H)CH$_3$, N(CH$_3$)$_2$, CH$_2$NH$_2$, CH$_2$N(H)CH$_3$CH$_2$N(CH$_3$)$_2$, CH$_2$OH; or an unsubstituted $C_{1-4}$-aliphatic residue;

More preferably, $R^2$ is selected from the group consisting of H, F, Cl, CH$_3$; CF$_3$, CF$_2$H, CFH$_2$, CH$_2$CH$_3$, CN, OH, OCH$_3$, NH$_2$ and N(H)CH$_3$.

Even more preferably, $R^2$ is selected from the group consisting of H, F, Cl, OH, NH$_2$, CH$_3$ and CH$_2$CH$_3$.

Still more preferably, $R^2$ is selected from the group consisting of H, OH and NH$_2$. Most preferably, $R^2$ denotes H.

In another embodiment of the compound according to the present invention, $R^1$ denotes H; a $C_{1-4}$-aliphatic residue, unsubstituted or mono- or polysubstituted; a $C_{3-6}$-cycloaliphatic residue or a 3 to 7 membered heterocycloaliphatic residue, in each case unsubstituted or mono- or polysubstituted and in each case optionally bridged via a $C_{1-4}$-aliphatic group, which in turn may be unsubstituted or mono- or polysubstituted; with the proviso that if $R^1$ represents a 3 to 7 membered heterocycloaliphatic residue, said 3 to 7 membered heterocycloaliphatic residue is connected to the remaining part of the structure according to general formula (I) via a carbon atom of the 3 to 7 membered heterocycloaliphatic residue;

Preferably, $R^1$ is selected from the group consisting of unsubstituted $C_{1-4}$-aliphatic residue or unsubstituted cyclopropyl.

More preferably, is selected from the group consisting of unsubstituted $C_{1-4}$-aliphatic residue.

Even more preferably, $R^1$ is selected from CH$_3$ and CH$_2$CH$_3$. Most preferably, $R^1$ denotes CH$_3$.

According to invention, the compound according to general formula (I) is characterized that n represents 0 or 1, wherein if n represents 1, then J represents C—R$^8$ or N or N$^+$—O$^-$, K represents C—R$^9$ or N or N$^+$—O$^-$, M represents C—R$^{10}$ or N or N$^+$—O$^-$, Q represents C—R$^{11}$ or N or N$^+$—O$^-$, and R represents C—R$^{12}$ or N or N$^+$—O$^-$, with the proviso that 0, 1, 2 or 3 of variables J, K, M, Q and R independently of one another represent(s) either N or N$^+$—O$^-$, whereof 0 or 1 of variables J, K, M, Q and R independently of one another represent(s) N$^+$—O$^-$, wherein if n represents 0, then J represents C—R$^8$ or N or N$^+$—O$^-$ or O or S or NH or N(C$_{1-4}$-aliphatic residue), K represents C—R$^9$ or N or N$^+$—O$^-$ or O or S or NH or N(C$_{1-4}$-aliphatic residue), M represents C—R$^{10}$ or N or N$^+$—O$^-$ or O or S or NH or N(C$_{1-4}$-aliphatic residue) and Q represents C—R$^{11}$ or N or N$^+$—O$^-$ or O or S or NH or N(C$_{1-4}$-aliphatic residue), with the proviso that one of J, K, M and Q represents O or S or NH or N(C$_{1-4}$-aliphatic residue) and the remaining of J, K, M and Q independently represent C—R$^8$, respectively C—R$^9$, respectively C—R$^{10}$, respectively C—R$^1$ or N or N$^+$—O$^-$ and with the proviso that 0, 1, 2 or 3 of J, K, M and Q independently of one another represent either N or N$^+$—O$^-$, whereof 0 or 1 of variables J, K, M and Q represents N$^+$—O$^-$.

In another preferred embodiment of the invention, the compound according of general formula (I) is selected from the group, consisting of formulae -continued (Ik-1)

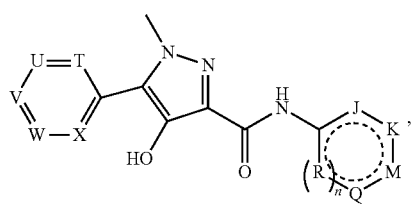

(Im-1)

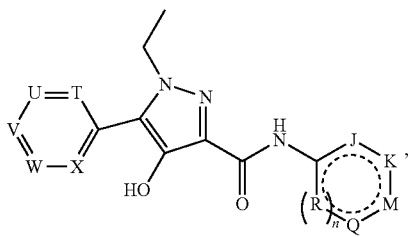

(In-1)

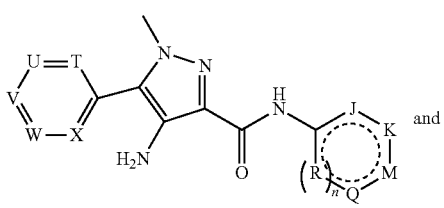

(Io-1)

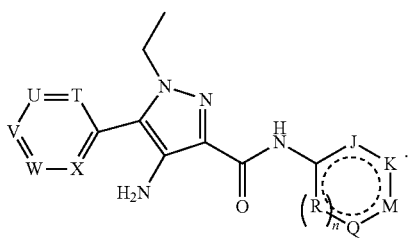

In particularly preferred embodiment of the invention, the compound according of general formula (I) is selected from the group, consisting of formulae (Ia-1), (Ib-1), (Ic-1), (Id-1), (Ie-1), (If-1), (Ig-1), (Ih-1), (Ii-1), (Ij-1), (Ik-1), (Im-1), (In-1) and (Io-1), wherein each n represents 1.

Preferably, the compound according of general formula (I) is selected from the group, consisting of formulae (Ia-1), (Ic-1), (Ie-1), (Ig-1), (Ii-1), (Ik-1) and (In-1), wherein each n represents 1.

More preferably, the compound according of general formula (I) is selected from the group, consisting of formulae (Ia-1), (Ic-1) and (Ig-1), wherein each n represents 1.

Most preferably, the compound according of general formula (I) is selected from formula (Ia-1), wherein n represents 1.

Within the scope of the present invention, the partial structure

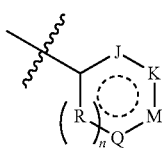

in general formula (I) represents an aryl or a heteroaryl residue. The residue is aromatic as depicted by the dashed circle line.

If n represents 1, then the partial structure in general formula (I) represents a 6 membered aryl or heteroaryl residue:

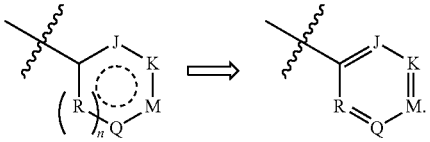

If n represents 0, then the partial structure in general formula (I) represents a 5 membered heteroaryl residue:

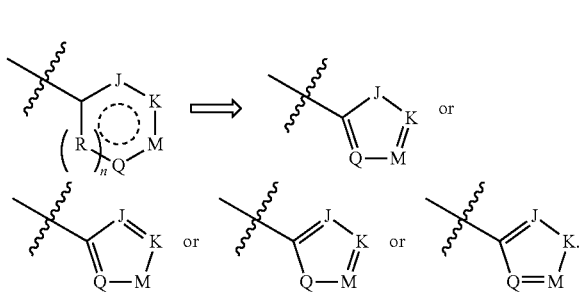

Examples for 5 membered heteroaryl residues are thienyl, thiazolyl, isothiazolyl, thiadiazolyl, furanyl, oxazolyl, isoxazolyl, oxadiazolyl, furazanyl, pyrrolyl, pyrazolyl, imidazolyl and triazolyl, in each case unsubstituted or mono- or polysubstituted.

In a preferred embodiment of the present invention, the compound according to general formula (I) is characterized in that n represents 1, and J represents $C-R^8$ or N or $N^+-O^-$, K represents $C-R^9$ or N or $N^+-O^-$, M represents $C-R^{10}$ or N or $N^+-O^-$, Q represents $C-R^{11}$ or N or $N^+-O^-$, and R represents $C-R^{12}$ or N or $N^+-O^-$, with the proviso that 0, 1, 2 or 3 of variables J, K, M, Q and R independently of one another represent(s) either N or $N^+-O^-$, whereof 0 or 1 of variables J, K, M, Q and R independently represents $N^+-O^-$.

In another preferred embodiment of the present invention, the compound according to general formula (I) is characterized in that n represents 1, and J represents $C-R^8$, K represents $C-R^9$, M represents $C-R^{10}$ or N, Q represents $C-R^{11}$ and R represents $C-R^{12}$.

In another preferred embodiment of the present invention, the compound according to general formula (I) is characterized in that n represents 1, and J represents $C-R^8$, K represents $C-R^9$, M represents $C-R^{10}$, Q represents $C-R^{11}$ and R represents $C-R^{12}$.

In another preferred embodiment of the present invention, the compound according to general formula (I) is characterized in that n represents 1, and J represents $C-R^8$, K represents $C-R^9$, M represents N, Q represents $C-R^1$ and R represents $C-R^{12}$.

In yet another preferred embodiment of the present invention, the compound according to general formula (I) is characterized in that n represents 1, and J represents C—$R^8$, K represents C—$R^9$, M represents C—$R^{10}$, Q represents C—$R^{11}$ and R represents C—$R^{12}$.

In yet another preferred embodiment of the present invention, the compound according to general formula (I) is characterized in that n represents 1, and J represents C—$R^8$, K represents C—$R^9$, M represents N, Q represents C—$R^1$ and R represents C—$R^{12}$.

Within this embodiment of the present invention, a particular substitution pattern on the cyclic substituent, incorporating J, K, M, Q and R, proved to be particular beneficial for the activity of the compounds according to the present invention.

In one preferred embodiment of the invention, the compound according of general formula (I) is characterized in that n represents 1, and J represents C—$R^8$ and/or R represents C—$R^{12}$,
wherein $R^8$ and $R^{12}$ are independently of one another selected from the group consisting of H; $CH_3$; $CF_3$; $CF_2H$; $CFH_2$; $CF_2Cl$; $CFCl_2$; $CH_2CH_3$; $CH_2CF_3$; CN; OH; $OCH_3$; $OCHF_2$; $OCH_2F$; $OCHF_2$; $OCF_3$; $NH_2$; $NHCH_3$; $N(CH_3)_2$; $NH(C=O)CH_3$; F; Cl and Br,
with the proviso that at least one of $R^8$ and $R^{12}$ does not denote H.

Preferably, J represents C—$R^8$, wherein $R^8$ is selected from the group consisting of H; $CH_3$; $CF_3$; $CF_2H$; $CFH_2$; $CF_2Cl$; $CFCl_2$; $CH_2CH_3$; $CH_2CF_3$; CN; OH; $OCH_3$; $OCHF_2$; $OCH_2F$; $OCHF_2$; $OCF_3$; $NH_2$; $NHCH_3$; $N(CH_3)_2$; $NH(C=O)CH_3$; F; Cl and Br, more preferably from the group consisting of H; $CH_3$; $CF_3$; CN; OH; $OCH_3$; F; Cl and Br, even more preferably from the group consisting of H; $CH_3$; CN; F and Cl, and most preferably $R^8$ denotes F.

Preferably, n represents 1, and

R represents C—$R^{12}$, wherein $R^{12}$ is selected from the group consisting of H; $CH_3$; $CF_3$; $CF_2H$; $CFH_2$; $CF_2Cl$; $CFCl_2$; $CH_2CH_3$; $CH_2CF_3$; CN; OH; $OCH_3$; $OCHF_2$; $OCH_2F$; $OCHF_2$; $OCF_3$; $NH_2$; $NHCH_3$; $N(CH_3)_2$; $NH(C=O)CH_3$; F; Cl and Br, more preferably from the group consisting of H; $CH_3$; $CF_3$; CN; OH; $OCH_3$; F; Cl and Br, and even more preferably from the group consisting of H; $CH_3$; CN; F and Cl.

In a preferred embodiment of the compound according to the present invention, n represents 1, and J represents C—$R^8$, wherein $R^8$ denotes H, and R represents C—$R^{12}$, wherein $R^{12}$ is selected from the group consisting of $CH_3$; $CF_3$; $CF_2H$; $CFH_2$; $CF_2Cl$; $CFCl_2$; $CH_2CH_3$; $CH_2CF_3$; CN; OH; $OCH_3$; $OCHF_2$; $OCH_2F$; $OCHF_2$; $OCF_3$; $NH_2$; $NHCH_3$; $N(CH_3)_2$; $NH(C=O)CH_3$; F; Cl and Br, more preferably from the group consisting of $CH_3$; $CF_3$; CN; OH; $OCH_3$; F and Cl, and even more preferably from the group consisting of $CH_3$; CN; F and Cl.

In a preferred embodiment of the compound according to the present invention, n represents 1, and J represents C—$R^8$, wherein $R^8$ denotes F, and R represents N.

In another preferred embodiment of the compound according to the present invention, n represents 1, J represents C—$R^8$, wherein $R^8$ denotes F, and R represents C—$R^{12}$, wherein $R^{12}$ is selected from the group consisting of H; $CH_3$; $CF_3$; CN; OH; $OCH_3$; F; Cl and Br.

In yet another preferred embodiment of the compound according to the present invention, n represents 1, J represents C—$R^8$, wherein $R^8$ denotes F, and R represents C—$R^{12}$, wherein $R^{12}$ denotes H.

In yet another preferred embodiment of the compound according to the present invention, n represents 1, J represents C—$R^8$, wherein $R^8$ denotes F, and R represents C—$R^{12}$, wherein $R^{12}$ denotes $CH_3$.

In yet another preferred embodiment of the compound according to the present invention, n represents 1, J represents C—$R^8$, wherein $R^8$ denotes F, and R represents C—$R^{12}$, wherein $R^{12}$ denotes CN.

In yet another preferred embodiment of the compound according to the present invention, n represents 1, J represents C—$R^8$, wherein $R^8$ denotes F, and R represents C—$R^{12}$, wherein $R^{12}$ denotes F.

In yet another preferred embodiment of the compound according to the present invention, n represents 1, J represents C—$R^8$, wherein $R^8$ denotes F, and R represents C—$R^{12}$, wherein $R^{12}$ denotes Cl.

In one preferred embodiment of the invention, the compound according of general formula (I) is characterized in that M represents N or $N^+$—$O^-$ or C—$R^{10}$, wherein $R^{10}$ is selected from the group consisting of H; F; Cl; CN; $CF_3$; $CF_2H$; $CFH_2$; $CF_2Cl$; $CFCl_2$; a $C_{1-8}$-aliphatic residue; $C(=O)OH$; $C(=O)$—$NH_2$; $C(=O)$—$C_{1-8}$-aliphatic residue; $C(=O)O$—$C_{1-8}$-aliphatic residue; $C(=O)NH$—$C_{1-8}$-aliphatic residue; $C(=O)N(C_{1-8}$-aliphatic residue$)_2$; OH; O—$C_{1-8}$-aliphatic residue; $OCF_3$; $OCF_2H$; $OCFH_2$; O—$C(=O)$—$C_{1-8}$-aliphatic residue; $NH_2$; N(H)—$C_{1-8}$-aliphatic residue; $N(C_{1-8}$-aliphatic residue$)_2$; N(H)—$C(=O)$—$C_{1-8}$-aliphatic residue; $N(C_{1-8}$-aliphatic residue)-$S(=O)_2$—$C_{1-8}$-aliphatic residue; $N(H)$—$S(=O)_2$—$NH_2$.

Preferably, M represents N or $N^+$—$O^-$ or C—$R^{10}$, wherein $R^{10}$ is selected from the group consisting of H; F; Cl; CN; $OCH_3$; $CH_3$; $CF_3$; $CF_2H$ and $CFH_2$.

In another preferred embodiment of the invention, the compound according of general formula (I) is characterized in that n represents 1, J represents C—$R^8$ and/or R represents C—$R^{12}$,
wherein $R^8$ and $R^{12}$ are independently of one another selected from the group consisting of H; $CH_3$; $CF_3$; $CF_2H$; $CFH_2$; $CH_2CH_3$; CN; OH, $OCH_3$, $OCHF_2$, $OCH_2F$; $OCHF_2$; $OCF_3$; $NH_2$; $NHCH_3$; $N(CH_3)_2$; $NH(C=O)CH_3$; F and Cl with the proviso that at least one of $R^8$ and $R^{12}$ does not denote H;

K represents C—$R^9$ or N and Q represents C—$R^{11}$ or N,
wherein $R^9$ and $R^{11}$ are independently of one another selected from the group consisting of H; F; Cl; CN; $CF_3$; $CF_2H$; $CFH_2$; $OCF_3$; $OCF_2H$; $OCFH_2$; an unsubstituted $C_{1-4}$-aliphatic residue; OH; and an unsubstituted O—$C_{1-4}$-aliphatic residue;

and

M represents N or $N^+$—$O^-$ or C—$R^{10}$,
wherein $R^{10}$ is selected from the group consisting of H; F; Cl; CN; $OCH_3$; $CH_3$; $CF_3$; $CF_2H$ and $CFH_2$.

In another preferred embodiment of the invention, the compound according of general formula (I) is characterized in that n represents 1, J represents C—$R^8$ and/or R represents C—$R^{12}$,
wherein $R^8$ and $R^{12}$ are independently of one another selected from the group consisting of H; $CH_3$; $CF_3$; $CF_2H$; $CFH_2$; $CH_2CH_3$; CN; OH, $OCH_3$, $OCHF_2$, OCH$_2$F; OCHF$_2$; OCF$_3$; NH$_2$; NHCH$_3$; N(CH$_3$)$_2$; NH(C=O)CH$_3$; F and Cl, with the proviso that at least one of R$^8$ and R$^{12}$ does not denote H;

K represents C—R$^9$ and Q represents C—R$^{11}$, wherein R$^9$ and R$^{11}$ both denote H;

and

M represents N or N$^+$—O$^-$ or C—R$^{10}$, wherein R$^{10}$ is selected from the group consisting of H; F; Cl; OCH$_3$; CN; CH$_3$; CF$_3$; CF$_2$H and CFH$_2$.

In another preferred embodiment of the compound according to the present invention, n represents 1, J represents C—R$^8$, wherein R$^8$ denotes F, R represents C—R$^{12}$, wherein R$^{12}$ denotes H.

K represents C—R$^9$ and Q represents C—R$^{11}$, wherein R$^9$ and R$^{11}$ both denote H, and M represents N.

In another preferred embodiment of the compound according to the present invention, n represents 1,0

J represents C—R$^8$, wherein R$^8$ denotes CH$_3$,

R represents C—R$^{12}$, wherein R$^{12}$ denotes H.

K represents C—R$^9$ and Q represents C—R$^{11}$, wherein R$^9$ and R$^{11}$ both denote H, and M represents N.

In another preferred embodiment of the compound according to the present invention, n represents 1, J represents C—R$^8$, wherein R$^8$ denotes F, R represents C—R$^{12}$, wherein R$^{12}$ denotes H.

K represents C—R$^9$ and Q represents C—R$^{11}$, wherein R$^9$ and R$^{11}$ both denote H, and M represents C—R$^{10}$, wherein R$^{10}$ denotes H.

In another preferred embodiment of the compound according to the present invention, n represents 1, J represents C—R$^8$, wherein R$^8$ denotes H, R represents C—R$^{12}$, wherein R$^{12}$ denotes H.

K represents C—R$^9$ and Q represents C—R$^{11}$, wherein R$^9$ and R$^{11}$ both denote H, and M represents C—R$^{10}$, wherein R$^{10}$ denotes F.

In another preferred embodiment of the compound according to the present invention, n represents 1, J represents C—R$^8$, wherein R$^8$ denotes H, R represents C—R$^{12}$, wherein R$^{12}$ denotes H.

K represents C—R$^9$ and Q represents C—R$^{11}$, wherein R$^9$ and R$^{10}$ both denote H, and M represents C—R$^{10}$, wherein R$^{10}$ denotes OCH$_3$.

In another preferred embodiment of the compound according to the present invention, J represents C—R$^8$, wherein R$^8$ denotes F, R represents C—R$^{12}$, wherein R$^{12}$ denotes F.

K represents C—R$^9$ and Q represents C—R$^{11}$, wherein R$^9$ and R$^{11}$ both denote H, and M represents N.

In another preferred embodiment of the compound according to the present invention, n represents 1, J represents C—R$^8$, wherein R$^8$ denotes F, R represents C—R$^{12}$, wherein R$^{12}$ denotes F.

K represents C—R$^9$ and Q represents C—R$^{11}$, wherein R$^9$ and R$^{11}$ both denote H, and M represents C—R$^{10}$, wherein R$^{10}$ denotes H.

In another preferred embodiment of the compound according to the present invention, n represents 1, J represents C—R$^8$, wherein R$^8$ denotes F, R represents C—R$^{12}$, wherein R$^{12}$ denotes Cl.

K represents C—R$^9$ and Q represents C—R$^{11}$, wherein R$^9$ and R$^{11}$ both denote H, and M represents N.

In another preferred embodiment of the compound according to the present invention, n represents 1, J represents C—R$^8$, wherein R$^8$ denotes F, R represents C—R$^{12}$, wherein R$^{12}$ denotes Cl.

K represents C—R$^9$ and Q represents C—R$^{11}$, wherein R$^9$ and R$^{11}$ both denote H, and M represents C—R$^{10}$, wherein R$^{10}$ denotes H.

In a particular preferred embodiment of the invention, the compound according of general formula (I) is selected from the group consisting of

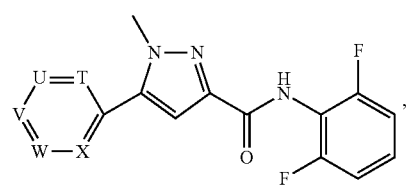
(Ia-1-i)

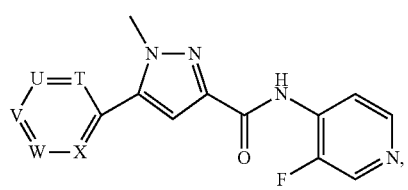
(Ia-1-ii)

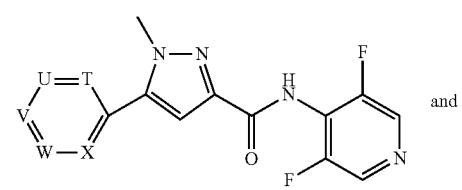
(Ia-1-iii)

and

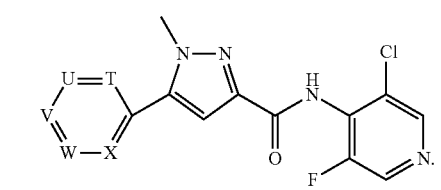
(Ia-1-iv)

In another particular preferred embodiment of the invention, the compound according of general formula (I) is selected from the group consisting of

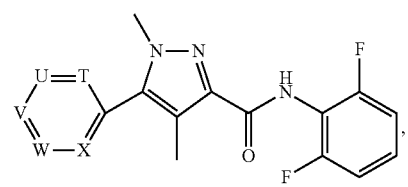
(Ic-1-i)

-continued

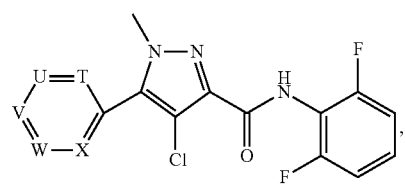 (Ic-1-ii)

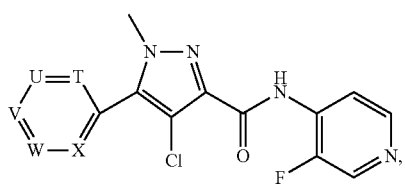 (Ic-1-iii) and

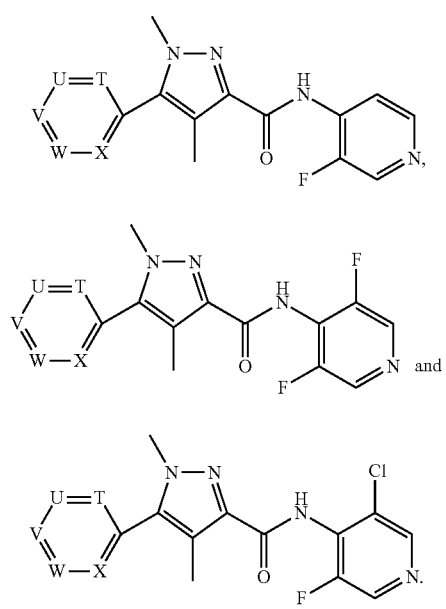 (Ic-1-iv)

In another particular preferred embodiment of the invention, the compound according of general formula (I) is selected from the group consisting of

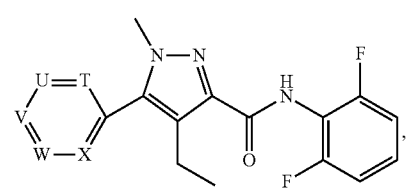 (Ie-1-i),

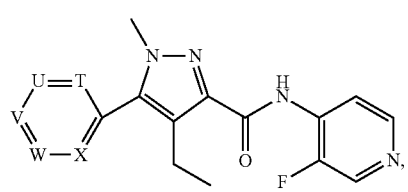 (Ie-1-ii),

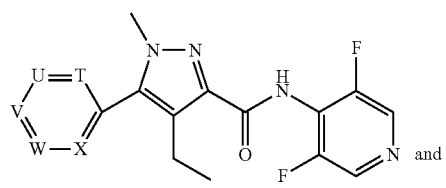 (Ie-1-iii) and

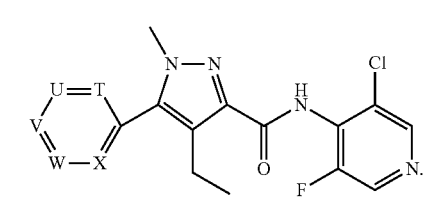 (Ie-1-iv).

In another particular preferred embodiment of the invention, the compound according of general formula (I) is selected from the group consisting of

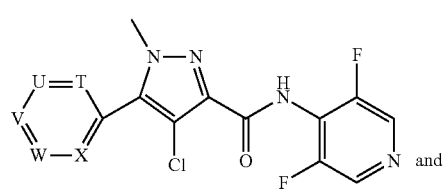 (Ig-1-i),

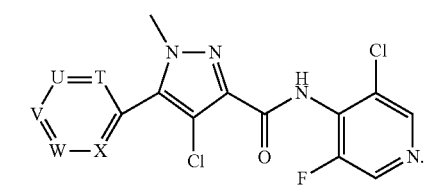 (Ig-1-ii),

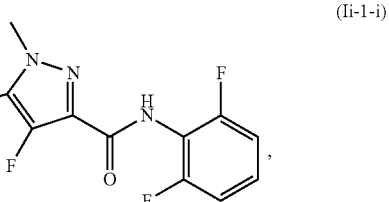 (Ig-1-iii) and

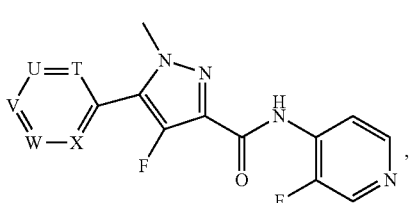 (Ig-1-iv).

In another particular preferred embodiment of the invention, the compound according of general formula (I) is selected from the group consisting of

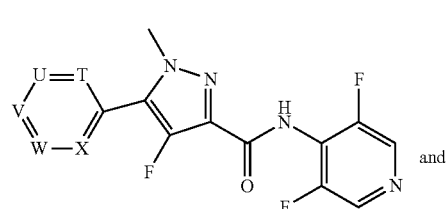 (Ii-1-i), (Ii-1-ii), (Ii-1-iii) and

In another particular preferred embodiment of the invention, the compound according of general formula (I) is selected from the group consisting of (Ik-1-i), (Ik-1-ii), (Ik-1-iii) and (Ik-1-iv).

In another particular preferred embodiment of the invention, the compound according of general formula (I) is selected from the group consisting of (In-1-i), (In-1-ii), (In-1-iii) and (In-1-iv).

In another preferred embodiment of the present invention, the compound according to the present invention is characterized in that T represents C—R$^3$, U represents C—R$^4$, V represents C—R$^5$, W represents C—R$^6$, and X represents C—R$^7$.

In another preferred embodiment of the present invention, the compound according to the present invention is characterized in that T represents N, U represents C—R$^4$, V represents C—R$^5$, W represents C—R$^6$, and X represents C—R$^7$.

In another preferred embodiment of the present invention, the compound according to the present invention is characterized in that T represents N, U represents N, V represents C—R$^5$, W represents C—R$^6$, and X represents C—R$^7$.

In another preferred embodiment of the present invention, the compound according to the present invention is characterized in that T represents N, U represents C—R$^4$, V represents N, W represents C—R$^6$, and X represents C—R$^7$.

In another preferred embodiment of the present invention, the compound according to the present invention is characterized in that T represents N, U represents C—R$^4$, V represents C—R$^5$, W represents N, and X represents C—R$^7$.

In another preferred embodiment of the present invention, the compound according to the present invention is characterized in that T represents N, U represents C—R$^4$, V represents C—R$^5$, W represents C—R$^6$, and X represents N.

In another preferred embodiment of the present invention, the compound according to the present invention is characterized in that T represents C—R$^3$, U represents N, V represents C—R$^5$, W represents C—R$^6$, and X represents C—R$^7$.

In another preferred embodiment of the present invention, the compound according to the present invention is characterized in that T represents C—R$^3$, U represents N, V represents N, W represents C—R$^6$, and X represents C—R$^7$.

In another preferred embodiment of the present invention, the compound according to the present invention is characterized in that T represents C—R$^3$, U represents N, V represents C—R$^5$, W represents N, and X represents C—R$^7$.

In one preferred embodiment of the present invention, the compound according to the present invention is characterized in that T represents C—R$^3$, U represents C—R$^4$, V represents N, W represents C—R$^6$, and X represents C—R$^7$.

In another preferred embodiment of the present invention, the compound according to the present invention is characterized in that T represents N, U represents N, V represents C—$R^5$, W represents C—$R^6$, and X represents N.

In another preferred embodiment of the present invention, the compound according to the present invention is characterized in that T represents C—$R^3$, U represents N, V represents N, W represents C—$R^6$, and X represents N.

In another preferred embodiment of the present invention, the compound according to the present invention is characterized in that T represents N, U represents N, V represents C—$R^5$, W represents N, and X represents C—$R^7$.

In a preferred embodiment of the present invention, the compound according to the present invention is characterized in that n represents 1, J represents C—$R^8$ or N or $N^+$—$O^-$, K represents C—$R^9$ or N or $N^+$—$O^-$, M represents C—$R^{10}$ or N or $N^+$—$O^-$, Q represents C—$R^{11}$ or N or $N^+$—$O^-$, and R represents C—$R^{12}$ or N or $N^+$—$O^-$, with the proviso that 0, 1, 2 or 3 of variables J, K, M, Q and R independently of one another represent(s) either N or $N^+$—$O^-$, whereof 0 or 1 of variables J, K, M, Q and R independently represents $N^+$—$O^-$, T represents C—$R^3$, U represents C—$R^4$, V represents C—$R^5$, W represents C—$R^6$, and X represents C—$R^7$.

In a preferred embodiment of the present invention, the compound according to the present invention is characterized in that n represents 1, J represents C—$R^8$, K represents C—$R^9$, M represents C—$R^{10}$, Q represents C—$R^{11}$ and R represents C—$R^{12}$, T represents C—$R^3$, U represents C—$R^4$, V represents C—$R^5$, W represents C—$R^6$, and X represents C—$R^7$.

In a preferred embodiment of the present invention, the compound according to the present invention is characterized in that n represents 1, J represents C—$R^8$, K represents C—$R^9$, M represents N, Q represents C—$R^{11}$ and R represents C—$R^{12}$, T represents C—$R^3$, U represents C—$R^4$, V represents C—$R^5$, W represents C—$R^6$, and X represents C—$R^7$.

In another embodiment of the present invention, the compound according of general formula (I) is selected from the group, consisting of formulae (Ia-1), (Ic-1), (Ie-1), (Ig-1), (Ii-1), (Ik-1) and (In-1), wherein in each formula T represents C—$R^3$, U represents C—$R^4$, V represents C—$R^5$, W represents C—$R^6$, and X represents C—$R^7$.

In another embodiment of the present invention, the compound according of general formula (I) is selected from the group, consisting of formulae (Ia-1), (Ic-1), (Ie-1), (Ig-1), (Ii-1), (Ik-1) and (In-1), wherein in each formula n represents 1, T represents C—$R^3$, U represents C—$R^4$, V represents C—$R^5$, W represents C—$R^6$, and X represents C—$R^7$.

In another preferred embodiment of the present invention, the compound according of general formula (I) is selected from the group, consisting of formulae (Ia-1), (Ic-1), (Ie-1), (Ig-1), (Ii-1), (Ik-1) and (In-1), wherein in each formula n represents 1, J represents C—$R^8$, K represents C—$R^9$, M represents C—$R^{10}$, Q represents C—$R^1$ and R represents C—$R^{12}$, T represents C—$R^3$, U represents C—$R^4$, V represents C—$R^5$, W represents C—$R^6$, and X represents C—$R^7$.

In another preferred embodiment of the present invention, the compound according of general formula (I) is selected from the group, consisting of formulae (Ia-1), (Ic-1), (Ie-1), (Ig-1), (Ii-1), (Ik-1) and (In-1), wherein in each formula n represents 1, J represents C—$R^8$, K represents C—$R^9$, M represents N, Q represents C—$R^{11}$ and R represents C—$R^{12}$, T represents C—$R^3$, U represents C—$R^4$, V represents C—$R^5$, W represents C—$R^6$ and X represents C—$R^7$.

More preferably, the compound according of general formula (I) is selected from the group, consisting of formulae (Ia-1-i), (Ia-1-ii), (Ia-1-iii), (Ic-1-i), (Ic-1-ii), (Ic-1-iii), (Ie-1-i), (Ie-1-ii), (Ie-1-iii), (Ig-1-i), (Ig-1-ii), (Ig-1-iii), (Ii-1-i), (Ii-1-ii), (Ii-1-iii), (Ik-1-i), (Ik-1-ii), (Ik-1-iii), (In-1-i), (In-1-ii) and (In-1-iii), wherein T represents C—$R^3$, U represents C—$R^4$, V represents C—$R^5$, W represents C—$R^6$, and X represents C—$R^7$.

Still more preferably, the compound according of general formula (I) is selected from the group, consisting of formulae (Ia-1-i), (Ia-1-iii), (Ic-1-i), (Ic-1-iii), (Ig-1-i), (Ig-1-iii), (Ik-1-i), (Ik-1-iii), (In-1-i) and (In-1-iii), wherein T represents C—$R^3$, U represents C—$R^4$, V represents C—$R^5$, W represents C—$R^6$, and X represents C—$R^7$.

In one preferred embodiment of the present invention, the compound according to the present invention is characterized in that one of $R^4$, $R^5$ and $R^6$ is selected from the group consisting of a $C_{3-6}$-cycloaliphatic residue, unsubstituted or mono- or polysubstituted, a 3 to 7 membered heterocycloaliphatic residue, unsubstituted or mono- or polysubstituted, and a heteroaryl, unsubstituted or mono- or polysubstituted.

In a preferred embodiment of the compound according to the present invention, one of $R^4$, $R^5$ and $R^6$ denotes a $C_{3-6}$-cycloaliphatic residue, preferably a cyclopropyl, which even more preferably is unsubstituted.

In another preferred embodiment of the compound according to the present invention, one of $R^4$, $R^5$ and $R^6$ denotes a 3 to 7 membered heterocycloaliphatic residue, preferably selected from the group consisting of pyrrolidinyl, pyrrolinyl, pyrazolinyl, oxazolinyl, isoxazolinyl, oxadiazolinyl, tetrahydropyranyl, dihydropyrazinyl, pyrazinyl and morpholinyl, wherein the 3 to 7 membered heterocycloaliphatic residue is unsubstituted or mono- or di-substituted with at least one substituent, preferably selected from the group consisting of =O, $CH_3$, and $CH_2CH_3$.

In yet another preferred embodiment of the compound according to the present invention, one of $R^4$, $R^5$ and $R^6$ denotes a heteroaryl, preferably selected from the group consisting of thiazolyl, thiadiazolyl, oxazolyl, isoxazolyl, thienyl, pyrrolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of OH, $NH_2$, $CH_3$, and $CH_2CH_3$.

More preferably, one of $R^4$, $R^5$ and $R^6$ is selected from the group consisting of a $C_{3-6}$-cycloaliphatic residue, preferably cyclopropyl, preferably unsubstituted, a 3 to 6 membered heterocycloaliphatic residue, preferably selected from the group consisting of pyrrolidinyl, pyrrolinyl, pyrazolinyl, oxazolinyl, isoxazolinyl, oxadiazolinyl, tetrahydropyranyl, dihydropyrazinyl, pyrazinyl and morpholinyl, wherein the 3 to 6 membered heterocycloaliphatic residue is unsubstituted or mono- or di-substituted with at least one substituent, preferably selected from the group consisting of =O, $CH_3$, and $CH_2CH_3$, and a heteroaryl, preferably selected from the group consisting of thiazolyl, thiadiazolyl, oxazolyl, isoxazolyl, thienyl, pyrrolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of OH, $NH_2$, $CH_3$, and $CH_2CH_3$, and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted O—$C_{1-4}$-aliphatic residue.

Still more preferably, one of $R^4$, $R^5$ and $R^6$ is selected from the group consisting of
- a $C_{3-6}$-cycloaliphatic residue, preferably cyclopropyl, preferably unsubstituted,
- a 3 to 6 membered heterocycloaliphatic residue, preferably selected from the group consisting of pyrrolidinyl, pyrrolinyl, pyrazolinyl, oxazolinyl, isoxazolinyl, oxadiazolinyl, tetrahydropyranyl, dihydropyrazinyl, pyrazinyl and morpholinyl, wherein the 3 to 6 membered heterocycloaliphatic residue is unsubstituted or mono- or di-substituted with at least one substituent, preferably selected from the group consisting of =O, $CH_3$, and $CH_2CH_3$, and
- a heteroaryl, preferably selected from the group consisting of thiazolyl, thiadiazolyl, oxazolyl, isoxazolyl, thienyl, pyrrolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of OH, $NH_2$, $CH_3$, and $CH_2CH_3$, and the remaining substituents of $R^3$, $R^4$, $R^5$, $R^6$ and $R^7$ are independently selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; OH; and an unsubstituted O—$C_{1-4}$-aliphatic residue, preferably selected from the group consisting of F; Cl and H; and more preferably each denote H.

Even more preferably, one of $R^4$, $R^5$ and $R^6$ is selected from the group consisting of
- a $C_{3-6}$-cycloaliphatic residue, preferably cyclopropyl, preferably unsubstituted,
- a 3 to 6 membered heterocycloaliphatic residue, preferably selected from the group consisting of pyrrolidinyl, pyrrolinyl, pyrazolinyl, oxazolinyl, isoxazolinyl, oxadiazolinyl, tetrahydropyranyl, dihydropyrazinyl, pyrazinyl and morpholinyl, wherein the 3 to 6 membered heterocycloaliphatic residue is unsubstituted or mono- or di-substituted with at least one substituent, preferably selected from the group consisting of =O, $CH_3$, and $CH_2CH_3$, and
- a heteroaryl, preferably selected from the group consisting of thiazolyl, thiadiazolyl, oxazolyl, isoxazolyl, thienyl, pyrrolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of OH, $NH_2$, $CH_3$, and $CH_2CH_3$, and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted O—$C_{1-4}$-aliphatic residue, with the proviso that at least one of the remaining substituents of $R^3$, $R^4$, $R^5$, $R^6$ and $R^7$ does not denote H.

If $R^4$ is selected from the group consisting of
- a $C_{3-6}$-cycloaliphatic residue, preferably cyclopropyl, preferably unsubstituted,
- a 3 to 6 membered heterocycloaliphatic residue, preferably selected from the group consisting of pyrrolidinyl, pyrrolinyl, pyrazolinyl, oxazolinyl, isoxazolinyl, oxadiazolinyl, tetrahydro-pyranyl, dihydropyrazinyl, pyrazinyl and morpholinyl, wherein the 3 to 6 membered heterocycloaliphatic residue is unsubstituted or mono- or di-substituted with at least one substituent, preferably selected from the group consisting of =O, $CH_3$, and $CH_2CH_3$, and
- a heteroaryl, preferably selected from the group consisting of thiazolyl, thiadiazolyl, oxazolyl, isoxazolyl, thienyl, pyrrolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of OH, $NH_2$, $CH_3$, and $CH_2CH_3$, it is preferred that at least $R^7$ is selected from the group consisting of F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH and an unsubstituted O—$C_{1-4}$-aliphatic residue.

If $R^6$ is selected from the group consisting of
- a $C_{3-6}$-cycloaliphatic residue, preferably cyclopropyl, preferably unsubstituted,
- a 3 to 6 membered heterocycloaliphatic residue, preferably selected from the group consisting of pyrrolidinyl, pyrrolinyl, pyrazolinyl, oxazolinyl, isoxazolinyl, oxadiazolinyl, tetrahydro-pyranyl, dihydropyrazinyl, pyrazinyl and morpholinyl, wherein the 3 to 6 membered heterocycloaliphatic residue is unsubstituted or mono- or di-substituted with at least one substituent, preferably selected from the group consisting of =O, $CH_3$, and $CH_2CH_3$, and
- a heteroaryl, preferably selected from the group consisting of thiazolyl, thiadiazolyl, oxazolyl, isoxazolyl, thienyl, pyrrolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of OH, $NH_2$, $CH_3$, and $CH_2CH_3$, it is preferred that at least $R^3$ is selected from the group consisting of F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH and an unsubstituted O—$C_{1-4}$-aliphatic residue.

If $R^5$ is selected from the group consisting of
- a $C_{3-6}$-cycloaliphatic residue, preferably cyclopropyl, preferably unsubstituted,
- a 3 to 6 membered heterocycloaliphatic residue, preferably selected from the group consisting of pyrrolidinyl, pyrrolinyl, pyrazolinyl, oxazolinyl, isoxazolinyl, oxadiazolinyl, tetrahydro-pyranyl, dihydropyrazinyl, pyrazinyl and morpholinyl, wherein the 3 to 6 membered heterocycloaliphatic residue is unsubstituted or mono- or di-substituted with at least one substituent, preferably selected from the group consisting of =O, $CH_3$, and $CH_2CH_3$, and
- a heteroaryl, preferably selected from the group consisting of thiazolyl, thiadiazolyl, oxazolyl, isoxazolyl, thienyl, pyrrolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of OH, $NH_2$, $CH_3$, and $CH_2CH_3$,
it is preferred that at least one of $R^3$ and $R^7$ is selected from the group consisting of F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH and an unsubstituted $O$—$C_{1-4}$-aliphatic residue.

In a particular preferred embodiment of the present invention, the compound according to the present invention is characterized in that
$R^1$ denotes an unsubstituted $C_{1-4}$-aliphatic residue, preferably denotes $CH_3$ or $CH_2CH_3$; more preferably $CH_3$;
$R^2$ denotes H; F; Cl, OH, $OCH_3$, $NH_2$, $NHCH_3$, $N(CH_3)_2$, $CH_2NH_2$, $CH_2N(H)CH_3CH_2N(CH_3)_2$, $CH_2OH$; or an unsubstituted $C_{1-4}$-aliphatic residue; preferably denotes H, Cl, F, OH, $NH_2$, $CH_3$ or $CH_2CH_3$; more preferably H;
T represents C—$R^3$ or N, U represents C—$R^4$ or N, V represents C—$R^5$ or N, W represents C—$R^6$ or N, and X represents C—$R^7$ or N,
with the proviso that 0, 1, 2 or 3 of variables T, U, V, W and X independently of one another represent(s) N,
and with the proviso that at least one of U, V and W does not represent N,
   wherein one of $R^4$, $R^5$ and $R^6$ is selected from the group consisting of
      a $C_{3-6}$-cycloaliphatic residue, preferably cyclopropyl, preferably unsubstituted,
      a 3 to 7 membered heterocycloaliphatic residue, preferably isoxazolinyl, oxadiazolinyl, oxazolinyl, tetrahydropyranyl, dihydropyrazinyl, pyrazinyl or morpholinyl, wherein the 3 to 7 membered heterocycloaliphatic residue is unsubstituted or mono- or di-substituted with at least one substituent, preferably selected from the group consisting of =O, $CH_3$, and $CH_2CH_3$, and
      a heteroaryl, preferably selected from the group consisting of thiazolyl, oxazolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of $NH_2$, $CH_3$, and $CH_2CH_3$,
   and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted $O$—$C_{1-4}$-aliphatic residue,
   with the proviso that at least one of the remaining substituents of $R^3$, $R^4$, $R^5$, $R^6$ and $R^7$ does not denote H;
n represents 1,
J represents C—$R^8$ and/or R represents C—$R^{12}$,
   wherein $R^8$ and $R^{12}$ are independently of one another selected from the group consisting of H; $CH_3$; $CF_3$; $CF_2H$; $CFH_2$; $CF_2Cl$; $CFCl_2$; $CH_2CH_3$; CN; OH, $OCH_3$, $OCHF_2$, $OCH_2F$; $OCHF_2$; $OCF_3$; $NH_2$; $NHCH_3$; $N(CH_3)_2$; $NH(C=O)CH_3$; F; Cl and Br, with the proviso that at least one of $R^8$ and $R^{12}$ does not denote H;
K represents C—$R^9$ and Q represents C—$R^{11}$,
   wherein $R^9$ and $R^{11}$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; OH; and an unsubstituted $O$—$C_{1-4}$-aliphatic residue;
and
M represents N or $N^+$—$O^-$ or C—$R^{10}$,
   wherein $R^{10}$ is selected from the group consisting of H; F; Cl; $OCH_3$; CN; $CH_3$; $CF_3$; $CF_2H$ and $CFH_2$, optionally in the form of a single stereoisomer or a mixture of stereoisomers, in the form of the free compound and/or a physiologically acceptable salt and/or a physiologically acceptable solvate thereof.

In a particular preferred embodiment of the present invention, the compound according to the present invention is characterized in that
$R^1$ denotes an unsubstituted $C_{1-4}$-aliphatic residue, preferably denotes $CH_3$ or $CH_2CH_3$; more preferably $CH_3$;
$R^2$ denotes H; F; Cl, OH, $OCH_3$, $NH_2$, $NHCH_3$, $N(CH_3)_2$, $CH_2NH_2$, $CH_2N(H)CH_3CH_2N(CH_3)_2$, $CH_2OH$; or an unsubstituted $C_{1-4}$-aliphatic residue; preferably denotes H, Cl, F, OH, $NH_2$, $CH_3$ or $CH_2CH_3$; more preferably H;
T represents C—$R^3$ or N, U represents C—$R^4$ or N, V represents C—$R^5$ or N, W represents C—$R^6$ or N, and X represents C—$R^7$ or N,
with the proviso that 0, 1, 2 or 3 of variables T, U, V, W and X independently of one another represent(s) N,
and with the proviso that at least one of U, V and W does not represent N,
   wherein one of $R^4$, $R^5$ and $R^6$ is selected from the group consisting of
      a $C_{3-6}$-cycloaliphatic residue, preferably cyclopropyl, preferably unsubstituted,
      a 3 to 7 membered heterocycloaliphatic residue, preferably isoxazolinyl, oxadiazolinyl, oxazolinyl, tetrahydropyranyl, dihydropyrazinyl, pyrazinyl or morpholinyl, wherein the 3 to 7 membered heterocycloaliphatic residue is unsubstituted or mono- or di-substituted with at least one substituent, preferably selected from the group consisting of =O, $CH_3$, and $CH_2CH_3$, and
      a heteroaryl, preferably selected from the group consisting of thiazolyl, oxazolyl, pyrazolyl, oxadiazolyl, tetrazolyl, triazolyl, pyridyl and pyrimidinyl, wherein the heteroaryl is unsubstituted or mono- or di-substituted with at least one substituent, preferably selected from the group consisting of $NH_2$, $CH_3$, and $CH_2CH_3$,
   and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted $O$—$C_{1-4}$-aliphatic residue, preferably selected from the group consisting of F; Cl and H; and more preferably each denote H,
n represents 1,
J represents C—$R^8$ and/or R represents C—$R^{12}$,
   wherein $R^8$ and $R^{12}$ are independently of one another selected from the group consisting of H; $CH_3$; $CF_3$; $CF_2H$; $CFH_2$; $CF_2Cl$; $CFCl_2$; $CH_2CH_3$; CN; OH, $OCH_3$, $OCHF_2$, $OCH_2F$; $OCHF_2$; $OCF_3$; $NH_2$; $NHCH_3$; $N(CH_3)_2$; $NH(C=O)CH_3$; F; Cl and Br, with the proviso that at least one of $R^8$ and $R^{12}$, does not denote H;
K represents C—$R^9$ and Q represents C—$R^{11}$,
   wherein $R^9$ and $R^{11}$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; OH; and an unsubstituted $O$—$C_{1-4}$-aliphatic residue;
and
M represents N or $N^+$—$O^-$ or C—$R^{10}$,
   wherein $R^{10}$ is selected from the group consisting of H; F; Cl; $OCH_3$; CN; $CH_3$; $CF_3$; $CF_2H$ and $CFH_2$, optionally in the form of a single stereoisomer or a mixture of stereoisomers, in the form of the free compound and/or a physiologically acceptable salt and/or a physiologically acceptable solvate thereof.

In another preferred embodiment of the present invention, the compound according of general formula (I) is selected from the group, consisting of formulae (Ia-1), (Ic-1), (Ie-1), (Ig-1), (Ii-1), (Ik-1) and (In-1), wherein in each formula T represents C—$R^3$, U represents C—$R^4$, V represents C—$R^5$, W represents C—$R^6$, and X represents C—$R^7$, wherein one of $R^4$, $R^5$ and $R^6$ is selected from the group consisting of
- a $C_{3-6}$-cycloaliphatic residue, preferably cyclopropyl, preferably unsubstituted,
- a 3 to 7 membered heterocycloaliphatic residue, preferably isoxazolinyl, oxadiazolinyl, oxazolinyl, tetrahydropyranyl, dihydropyrazinyl, pyrazinyl or morpholinyl, wherein the 3 to 7 membered heterocycloaliphatic residue is unsubstituted or mono- or di-substituted with at least one substituent, preferably selected from the group consisting of =O, $CH_3$, and $CH_2CH_3$, and
- a heteroaryl, preferably selected from the group consisting of thiazolyl, oxazolyl, pyrazolyl, oxadiazolyl, tetrazolyl, triazolyl, pyridyl, and pyrimidinyl, wherein the heteroaryl is unsubstituted or mono- or di-substituted with at least one substituent, preferably selected from the group consisting of $NH_2$, $CH_3$, and $CH_2CH_3$, and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted O—$C_{1-4}$-aliphatic residue, with the proviso that at least one of the remaining substituents of $R^3$, $R^4$, $R^5$, $R^6$ and $R^7$ does not denote H, n represents 1, J represents C—$R^8$, K represents C—$R^9$, M represents C—$R^{10}$ or N or $N^+$—$O^-$, Q represents C—$R^1$ and R represents C—$R^{12}$,
  wherein $R^8$ and $R^{12}$ are independently of one another selected from the group consisting of H; $CH_3$; $CF_3$; CN; OH; $OCH_3$, F and Cl, with the proviso that at least one of $R^8$ and $R^{12}$ does not denote H;

K represents C—$R^9$ and Q represents C—$R^{11}$,
  wherein $R^9$ and $R^{11}$ are selected from H;
and M represents N or $N^+$—$O^-$ or C—$R^{10}$,
  wherein $R^{10}$ is selected from the group consisting of H; F; Cl; $OCH_3$; CN; $CH_3$; $CF_3$; $CF_2H$ and $CFH_2$.

In another preferred embodiment of the present invention, the compound according of general formula (I) is selected from the group, consisting of formulae (Ia-1), (Ic-1), (Ie-1), (Ig-1), (Ii-1), (Ik-1) and (In-1), wherein in each formula T represents C—$R^3$, U represents C—$R^4$, V represents C—$R^5$, W represents C—$R^6$, and X represents C—$R^7$, wherein one of $R^4$, $R^5$ and $R^6$ is selected from the group consisting of
- a $C_{3-6}$-cycloaliphatic residue, preferably cyclopropyl, preferably unsubstituted,
- a 3 to 7 membered heterocycloaliphatic residue, preferably isoxazolinyl, oxadiazolinyl, oxazolinyl, tetrahydropyranyl, dihydropyrazinyl, pyrazinyl or morpholinyl, wherein the 3 to 7 membered heterocycloaliphatic residue is unsubstituted or mono- or di-substituted with at least one substituent, preferably selected from the group consisting of =O, $CH_3$, and $CH_2CH_3$, and
- a heteroaryl, preferably selected from the group consisting of thiazolyl, oxazolyl, pyrazolyl, oxadiazolyl, tetrazolyl, triazolyl, pyridyl, and pyrimidinyl, wherein the heteroaryl is unsubstituted or mono- or di-substituted with at least one substituent, preferably selected from the group consisting of $NH_2$, $CH_3$, and $CH_2CH_3$, and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted O—$C_{1-4}$-aliphatic residue, preferably selected from the group consisting of F; Cl and H; and more preferably each denote H, n represents 1, J represents C—$R^8$, K represents C—$R^9$, M represents C—$R^{10}$ or N or $N^+$—$O^-$, Q represents C—$R^1$ and R represents C—$R^{12}$,
  wherein $R^8$ and $R^{12}$ are independently of one another selected from the group consisting of H; $CH_3$; $CF_3$; CN; OH; $OCH_3$, F and Cl, with the proviso that at least one of $R^8$ and $R^{12}$ does not denote H;

K represents C—$R^9$ and Q represents C—$R^{11}$,
  wherein $R^9$ and $R^{11}$ are selected from H;
and M represents N or $N^+$—$O^-$ or C—$R^{10}$,
  wherein $R^{10}$ is selected from the group consisting of H; F; Cl; $OCH_3$; CN; $CH_3$; $CF_3$; $CF_2H$ and $CFH_2$.

In another particularly preferred embodiment of the present invention, the compound according of general formula (I) is characterized in that $R^1$ denotes $CH_3$;

$R^2$ denotes H or $CH_3$;

T represents C—$R^3$, U represents C—$R^4$, V represents C—$R^5$, W represents C—$R^6$, and X represents C—$R^7$, wherein one of $R^4$, $R^5$ and $R^6$ is selected from the group consisting of
- a $C_{3-6}$-cycloaliphatic residue, preferably cyclopropyl, preferably unsubstituted,
- a 3 to 7 membered heterocycloaliphatic residue, preferably isoxazolinyl, oxadiazolinyl, oxazolinyl, tetrahydropyranyl, dihydropyrazinyl, pyrazinyl or morpholinyl, wherein the 3 to 7 membered heterocycloaliphatic residue is unsubstituted or mono- or di-substituted with at least one substituent, preferably selected from the group consisting of =O, $CH_3$, and $CH_2CH_3$, and
- a heteroaryl, preferably selected from the group consisting of thiazolyl, oxazolyl, pyrazolyl, oxadiazolyl, tetrazolyl, triazolyl, pyridyl, and pyrimidinyl, wherein the heteroaryl is unsubstituted or mono- or di-substituted with at least one substituent, preferably selected from the group consisting of $NH_2$, $CH_3$, and $CH_2CH_3$, and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted O—$C_{1-4}$-aliphatic residue, with the proviso that at least one of the remaining substituents of $R^3$, $R^4$, $R^5$, $R^6$ and $R^7$ does not denote H;

n represents 1;

J represents C—$R^8$, K represents C—$R^9$, M represents C—$R^{10}$ or N or $N^+$—$O^-$, Q represents C—$R^{11}$ and R represents C—$R^{12}$,
  wherein $R^8$ and $R^{12}$ are independently of one another selected from the group consisting of H; $CH_3$; $CF_3$; CN; OH; $OCH_3$, F and Cl, with the proviso that at least one of $R^8$ and $R^{12}$ does not denote H;

K represents C—R⁹ and Q represents C—R¹¹,
  wherein R⁹ and R¹¹ are selected from H;
  and
M represents N or N⁺—O⁻ or C—R¹⁰,
  wherein R¹⁰ is selected from the group consisting of H; F; Cl; OCH₃; CN; CH₃; CF₃; CF₂H and CFH₂.

In another particularly preferred embodiment of the present invention, the compound according of general formula (I) is characterized in that
R¹ denotes CH₃;
R² denotes H or CH₃;
T represents C—R³, U represents C—R⁴, V represents C—R⁵, W represents C—R⁶, and X represents C—R⁷,
  wherein one of R⁴, R⁵ and R⁶ is selected from the group consisting of
    a C₃₋₆-cycloaliphatic residue, preferably cyclopropyl, preferably unsubstituted,
    a 3 to 7 membered heterocycloaliphatic residue, preferably isoxazolinyl, oxadiazolinyl, oxazolinyl, tetrahydropyranyl, dihydropyrazinyl, pyrazinyl or morpholinyl, wherein the 3 to 7 membered heterocycloaliphatic residue is unsubstituted or mono- or di-substituted with at least one substituent, preferably selected from the group consisting of =O, CH₃, and CH₂CH₃, and
    a heteroaryl, preferably selected from the group consisting of thiazolyl, oxazolyl, pyrazolyl, oxadiazolyl, tetrazolyl, triazolyl, pyridyl, and pyrimidinyl, wherein the heteroaryl is unsubstituted or mono- or di-substituted with at least one substituent, preferably selected from the group consisting of NH₂, CH₃, and CH₂CH₃,
and the remaining substituents of R³, R⁴, R⁵, R⁶ and R⁷ are independently of one another selected from the group consisting of H; F; Cl; Br; I; CN; CF₃; CF₂H; CFH₂; OCF₃; OCF₂H; OCFH₂; an unsubstituted C₁₋₄-aliphatic residue; OH; cyclopropyl; and an unsubstituted O—C₁₋₄-aliphatic residue, preferably selected from the group consisting of F; Cl and H; and more preferably each denote H;
n represents 1;
J represents C—R⁸, K represents C—R⁹, M represents C—R¹⁰ or N or N⁺—O⁻, Q represents C—R¹ and R represents C—R¹²,
  wherein R⁸ and R¹² are independently of one another selected from the group consisting of H; CH₃; CF₃; CN; OH; OCH₃, F and Cl, with the proviso that at least one of R⁸ and R¹² does not denote H;
K represents C—R⁹ and Q represents C—R¹¹,
  wherein R⁹ and R¹¹ are selected from H;
  and
M represents N or N⁺—O⁻ or C—R¹⁰,
  wherein R¹⁰ is selected from the group consisting of H; F; Cl; OCH₃; CN; CH₃; CF₃; CF₂H and CFH₂.

Particularly preferred compounds according to the invention are selected from the group consisting of 1 N-(3-Fluoro-pyridin-4-yl)-1-methyl-5-(2-methyl-5-thiazol-2-yl-phenyl)-1H-pyrazole-3-carboxylic acid amide
2 N-(3-Fluoro-pyridin-4-yl)-1-methyl-5-(2-methyl-5-oxazol-2-yl-phenyl)-1H-pyrazole-3-carboxylic acid amide
3 N-(2,6-Difluoro-phenyl)-1-methyl-5-(2-methyl-5-thiazol-2-yl-phenyl)-1H-pyrazole-3-carboxylic acid amide
4 N-(4-Methoxyphenyl)-1-methyl-5-(2-methyl-5-thiazol-2-yl-phenyl)-1H-pyrazole-3-carboxylic acid amide
N-(4-Fluorophenyl)-1-methyl-5-(2-methyl-5-thiazol-2-yl-phenyl)-1H-pyrazole-3-carboxylic acid amide
6 1-Methyl-N-(3-methyl-pyridin-4-yl)-5-(2-methyl-5-thiazol-2-yl-phenyl)-1H-pyrazole-3-carboxylic acid amide
7 N-(3-Fluoro-pyridin-4-yl)-5-(2-methoxy-5-thiazol-2-yl-phenyl)-1-methyl-1H-pyrazole-3-carboxylic acid amide
8 N-(2,6-Difluoro-phenyl)-5-(2-methoxy-5-thiazol-2-yl-phenyl)-1-methyl-1H-pyrazole-3-carboxylic acid amide
9 5-(2-Chloro-5-thiazol-2-yl-phenyl)-N-(3-fluoro-pyridin-4-yl)-1-methyl-1H-pyrazole-3-carboxylic acid amide
5-(2-Chloro-5-thiazol-2-yl-phenyl)-N-(2,6-difluoro-phenyl)-1-methyl-1H-pyrazole-3-carboxylic acid amide
11 N-(3-Fluoro-pyridin-4-yl)-1-methyl-5-(2-methyl-5-pyridin-4-yl-phenyl)-1H-pyrazole-3-carboxylic acid amide
12 N-(2,6-Difluoro-phenyl)-1-methyl-5-(2-methyl-5-pyridin-4-yl-phenyl)-1H-pyrazole-3-carboxylic acid amide
13 N-(2,6-Difluoro-phenyl)-1-methyl-5-(2-methyl-5-pyrimidin-5-yl-phenyl)-1H-pyrazole-3-carboxylic acid amide
14 N-(2,6-Difluoro-phenyl)-1-methyl-5-(3-thiazol-2-yl-phenyl)-1H-pyrazole-3-carboxylic acid amide
15 5-(5-Cyclopropyl-2-methoxy-phenyl)-N-(3-fluoro-pyridin-4-yl)-1-methyl-1H-pyrazole-3-carboxylic acid amide
16 5-(5-Cyclopropyl-2-methoxy-phenyl)-N-(2,6-difluoro-phenyl)-1-methyl-1H-pyrazole-3-carboxylic acid amide
17 5-(2-Cyclopropyl-5-methyl-pyrimidin-4-yl)-N-(2,6-difluoro-phenyl)-1-methyl-1H-pyrazole-3-carboxylic acid amide
18 N-(2,6-Difluoro-phenyl)-1-methyl-5-(2-methyl-5-oxazol-2-yl-phenyl)-1H-pyrazole-3-carboxylic acid amide
19 N-(2,6-Difluoro-phenyl)-1-methyl-5-[2-methyl-5-(3-methyl-[1,2,4]oxadiazol-5-yl)-phenyl]-1H-pyrazole-3-carboxylic acid amide
20 5-[5-(2-Amino-pyridin-4-yl)-2-methyl-phenyl]-N-(2,6-difluoro-phenyl)-1-methyl-1H-pyrazole-3-carboxylic acid amide
21 N-(3-Fluoro-pyridin-4-yl)-1-methyl-5-(2-methyl-5-tetrahydro-pyran-4-yl-phenyl)-1H-pyrazole-3-carboxylic acid amide
22 N-(2,6-Difluoro-phenyl)-1-methyl-5-(2-methyl-5-tetrahydro-pyran-4-yl-phenyl)-1H-pyrazole-3-carboxylic acid amide
23 N-(2,6-Difluoro-phenyl)-1-methyl-5-[2-methyl-5-(1-methyl-1H-[1,2,4]triazol-3-yl)-phenyl]-1H-pyrazole-3-carboxylic acid amide
24 N-(2,6-Difluoro-phenyl)-1-methyl-5-(2-methyl-4-thiazol-2-yl-phenyl)-1H-pyrazole-3-carboxylic acid amide
25 N-(2,6-Difluoro-phenyl)-1,4-dimethyl-5-(2-methyl-5-thiazol-2-yl-phenyl)-1H-pyrazole-3-carboxylic acid amide
26 N-(3-Fluoro-pyridin-4-yl)-1,4-dimethyl-5-(2-methyl-5-thiazol-2-yl-phenyl)-1H-pyrazole-3-carboxylic acid amide
27 N-(2,6-Difluoro-phenyl)-1,4-dimethyl-5-(3-thiazol-2-yl-phenyl)-1H-pyrazole-3-carboxylic acid amide
28 N-(2,6-Difluoro-phenyl)-1-methyl-5-[2-methyl-5-(5-methyl-4H-[1,2,4]triazol-3-yl)-phenyl]-1H-pyrazole-3-carboxylic acid amide
29 N-(3-Fluoro-pyridin-4-yl)-1,4-dimethyl-5-(3-thiazol-2-yl-phenyl)-1H-pyrazole-3-carboxylic acid amide
30 N-(2,6-Difluoro-phenyl)-1-methyl-5-[5-oxazol-2-yl-2-(trifluoromethyloxy)-phenyl]-1H-pyrazole-3-carboxylic acid amide
31 N-(3-Fluoro-pyridin-4-yl)-1-methyl-5-[5-oxazol-2-yl-2-(trifluoromethyloxy)-phenyl]-1H-pyrazole-3-carboxylic acid amide
32 N-(2,6-Difluoro-phenyl)-1-methyl-5-[2-methyl-5-(4H-[1,2,4]triazol-3-yl)-phenyl]-1H-pyrazole-3-carboxylic acid amide
33 N-(3,5-Difluoro-pyridin-4-yl)-1-methyl-5-[5-oxazol-2-yl-2-(trifluoromethyloxy)-phenyl]-1H-pyrazole-3-carboxylic acid amide 34  5-(5-Cyclopropyl-2-methoxy-phenyl)-N-(2,6-difluoro-phenyl)-1,4-dimethyl-1H-pyrazole-3-carboxylic acid amide 35  5-(5-Cyclopropyl-2-methoxy-phenyl)-N-(3,5-difluoro-pyridin-4-yl)-1,4-dimethyl-1H-pyrazole-3-carboxylic acid amide 36  5-[5-Cyclopropyl-2-(trifluoromethyloxy)-phenyl]-N-(2,6-difluoro-phenyl)-1-methyl-1H-pyrazole-3-carboxylic acid amide 37  5-[5-Cyclopropyl-2-(trifluoromethyloxy)-phenyl]-N-(3,5-difluoro-pyridin-4-yl)-1-methyl-1H-pyrazole-3-carboxylic acid amide 38  5-[5-Cyclopropyl-2-(trifluoromethyloxy)-phenyl]-N-(3-fluoro-pyridin-4-yl)-1-methyl-1H-pyrazole-3-carboxylic acid amide 39  5-[4-Cyclopropyl-2-(trifluoromethyloxy)-phenyl]-N-(2,6-difluoro-phenyl)-1-methyl-1H-pyrazole-3-carboxylic acid amide 40  5-[4-Cyclopropyl-2-(trifluoromethyloxy)-phenyl]-N-(3,5-difluoro-pyridin-4-yl)-1-methyl-1H-pyrazole-3-carboxylic acid amide 41  5-[4-Cyclopropyl-2-(trifluoromethyloxy)-phenyl]-N-(3-fluoro-pyridin-4-yl)-1-methyl-1H-pyrazole-3-carboxylic acid amide 42  2,6-Difluoro-N-[1-methyl-5-(3-thiazol-2-yl-phenyl)-1H-pyrazol-3-yl]-benzamide 43  4-Amino-N-(3,5-difluoro-pyridin-4-yl)-1-methyl-5-(2-methyl-5-oxazol-2-yl-phenyl)-1H-pyrazole-3-carboxylic acid amide 44  4-Amino-N-(2,6-difluoro-phenyl)-5-(2-methoxy-5-thiazol-2-yl-phenyl)-1-methyl-1H-pyrazole-3-carboxylic acid amide 45  4-amino-N-(3,5-difluoropyridin-4-yl)-5-(2-methoxy-5-(oxazol-2-yl)phenyl)-1-methyl-1H-pyrazole-3-carboxamide 46  4-amino-N-(2,6-difluorophenyl)-5-(2-methoxy-5-(oxazol-2-yl)phenyl)-1-methyl-1H-pyrazole-3-carboxamide 47  4-amino-N-(3,5-difluoropyridin-4-yl)-5-(2-methoxy-5-(thiazol-2-yl)phenyl)-1-methyl-1H-pyrazole-3-carboxamide 48  4-amino-N-(2,6-difluorophenyl)-5-(5-(5,5-dimethyl-4-oxo-4,5-dihydroisoxazol-3-yl)-2-methoxyphenyl)-1-methyl-1H-pyrazole-3-carboxamide 49  4-amino-N-(2,6-difluorophenyl)-1-methyl-5-(5-(oxazol-2-yl)-2-(trifluoromethoxy)phenyl)-1H-pyrazole-3-carboxamide 50  4-amino-N-(3,5-difluoropyridin-4-yl)-1-methyl-5-(5-(oxazol-2-yl)-2-(trifluoromethoxy)phenyl)-1H-pyrazole-3-carboxamide optionally in the form of a single stereoisomer or a mixture of stereoisomers, in the form of the free compound and/or a physiologically acceptable salt or solvate thereof.

The compounds according to the present invention are useful for calcium release-activated calcium (CRAC) channel regulation, preferably for use in CRAC channel inhibition.

The substances according to the invention hence act, for example, on the CRAC channel relevant in connection with various diseases, so that they are suitable as a pharmacologically active compound in pharmaceutical compositions.

The compounds according to the first aspect of the present invention and the corresponding stereoisomers and the respective salts and solvates are toxicologically safe and are therefore suitable as pharmacologically active ingredients in pharmaceutical compositions.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention is suitable for administration to adults and children, including toddlers and babies.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders. Likewise the compound according to the invention, if appropriate in the form of one of its pure stereoisomers, or if appropriate in the form of a corresponding salt or respectively in the form of a corresponding solvate, may also incorporated into the pharmaceutical composition in the form of a prodrug, which releases the active pharmacological agent through normal metabolic processes.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art, such as are described for example in "Remington's Pharmaceutical Sciences", A. R. Gennaro (Editor), 17$^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CRAC channels are believed to be involved in a variety of diseases or disorders in mammals such as humans. These include inflammatory disorders, allergic disorders and disorders of the immune system as well as disorders involving platelet or thrombotic activity.

Examples of allergic disorders include: rhinitis (such as allergic rhinitis), sinusitis, rhinosinusitis, chronic or recurrent otitis media, drug reactions, insect sting reactions, latex allergy, conjunctivitis, urticaria, ana-phylaxis and anaphylactoid reactions, atopic dermatitis and food allergies.

Examples of inflammatory disorders include: inflammatory lung disorders (such as asthma, acute respiratory distress syndrome, acute lung injury, chronic obstructive pulmonary disease, bronchiectasis and cystic fibrosis); chronic inflammatory disorders of joints (such as arthritis, rheumatoid arthritis, osteoarthritis and bone diseases associated with increased bone resorption); inflammatory bowel diseases (such as Barrett's oesophagus, ileitis, ulcerative colitis and Crohn's disease); inflammatory disorders of the eye (such as corneal dystrophy, trachoma, uveitis, sympathetic ophthalmitis and endo-phthalmitis); inflammatory diseases of the kidney (such as glomerulonephritis, nephrosis, nephritic syndrome and IgA nephropathy); inflammatory diseases of the liver; inflammatory disorders of the skin (such as psoriasis and eczema); inflammatory diseases of the central nervous system (such as chronic demyelinating diseases of the nervous system, multiple sclerosis, AIDS-related neurodegeneration and Alzheimers disease, infectious meningitis, enceophalomyelitis, Parkinson's disease, Huntington's disease, amyotrophic lateral sclerosis and viral or autoimmune encephalitis); inflammatory diseases of the muscle (such as polymyositis and polymyalgia rheumatica); inflammatory diseases of the heart (such as myocarditis and cardiomyopathy, ischemic heart disease, myocardial infarction and atherosclerosis); other diseases with significant inflammatory components, including tuberculosis; leprosy; allogeneic or xenogeneic transplantation (cells, stem cells, tissues or organs) graft rejection, graft-versus-host disease; pre-eclampsia; endometriosis, chronic liver failure; brain and spinal cord trauma and cancer; and conditions where systemic inflammation of the body may also be present (such as septic shock, hemorrhagic or anaphylactic shock or shock induced by cancer chemotherapy).

Examples of disorders of the immune system include: autoimmune diseases of the central and peripheral nervous system (such as multiple sclerosis, myasthenia gravis, Eaton-Lambert Myasthenic syndrome); autoimmune neurophathies (such as Guillain-Barré); autoimmune diseases of the eye (such as auto-immune uveitis); autoimmune diseases of the blood (such as autoimmune haemolytic anemia, pernicious anemia, and autoimmune thrombocytopenia e.g. Idiopathic Thrombocytopaenic Purpura); autoimmune diseases of the vasculature (such as temporal arteritis, anti-phospholipid syndrome, vasculitides e.g. Wegener's granulomatosis and Behcet's disease); autoimmune diseases of the skin (such as alopecia greata, psoriasis, dermatitis herpetiformis, pemphigus vulgaris, bullous pemphigoid and vitiligo); auto-immune disease of the gastrointestinal tract (such as coeliac disease, Crohn's disease, ulcerative colitis, primary biliary cirrhosis and autoimmune hepatitis); autoimmune disorders of the endocrine glands (such as Type1 diabetes mellitus, autoimmune thyroiditis, Grave's disease, Hashimoto's thyroiditis, autoimmune oophoritis and orchitis); autoimmune disorder of the adrenal gland (such as Addisons disease); auto-immune disorders of the exocrine glands (such as Sjogren's syndrome); and multi system autoimmune diseases including connective tissue and musculoskeletal system diseases (such as rheumatoid arthritis, systemic lupus erythematosus, scleroderma, polymyositis, dermatomyositis), spondyloarthropathies (such as ankylosing spondylitis and psoriatic arthritis).

Examples of conditions where anti-platelet or anti-thrombotic activity is useful for treatment and/or prophylaxis include: ischemic heart disease, myocardial infarction, cerebrovascular accident (stroke) and vascular thrombosis (venous, arterial and intra-cardiac).

Further diseases or conditions which may be treated by the compounds of the invention include conditions where mast cells and basophils contribute to pathology, such as mast cell leukaemia, mastocytosis, endometriosis and basophil leukaemia.

The term "disorders and/or diseases which are mediated, at least in part, by CRAC channels", is intended to include each of or all of the above disease states.

It is believed that the compounds of formula (I), having ICRAC inhibitory activity, may inhibit mast cell degranulation and/or inhibit T cell activation. Compounds having such activity may be particularly suitable for the treatment of a number of diseases and conditions, for example asthma; allergies such as allergic rhinitis; and nasal polyposis.

Due to the key role of calcium in the regulation of cellular proliferation in general, calcium channel inhibitors could act as cytostatic agents which may be useful in the treatment of dieseases of abnormal cellular proliferation, e.g. benign prostatic hyperplasia or familial adenomatosis polyposis. The compounds may be useful for the treatment of a variety of cancers as hematopoietic tumors of lymphoid lineage (such as leukemia, acute lymphocytic leukemia, acute lymphoblastic leukemia, B-cell lymphoma, T-cell lymphoma and Hodgkin's lymphoma); hematopoietic tumors of myeloid lineage (such as acute and chronic myelgenous leukemias); carcinomas, tumors of mesenchymal origin; tumors of the central and peripheral nervous system (such as astrocytoma and neuroblastoma) and other tumors such as melanoma and sarcoma.

Another aspect of the present invention therefore relates to a compound according to the first aspect of the present invention for the treatment and/or prophylaxis of a or more disorder and/or disease, selected from the group consisting of glomerulonephritis, uveitis, hepatic diseases or disorders, especially hepatitis, renal diseases or disorders, chronic obstructive pulmonary disease (COPD), rheumatoid arthritis (RA), multiple sclerosis, inflammatory bowel disease (IBD), especially Barrett's oesophagus, ileitis, ulcerative colitis or Crohn's Disease, vasculitis, dermatitis, dermatomyositis, atopic dermatitis, scleroderma, osteoarthritis, inflammatory muscle disease, allergic rhinitis, vaginitis, interstitial cystitis, osteoporosis, eczema, psoriasis, allogeneic or xenogeneic transplantation (cells, stem cells, tissues or organs) graft rejection, graft-versus-host disease, lupus erythematosus, type I diabetes, pulmonary fibrosis, thyroiditis, myasthenia gravis, autoimmune hemolytic anemia, cystic fibrosis, chronic relapsing hepatitis, hepatitis, primary biliary cirrhosis, allergic conjunctivitis, asthma, nasal polyposis; Sjogren's syndrome, cancer and other proliferative diseases, and autoimmune diseases or disorders.

Another embodiment of this aspect of the present invention relates to a compound according to the first aspect of the present invention for the treatment and/or prophylaxis of autoimmune diseases, in particular rheumatoid arthritis and psoriatic arthritis.

Another embodiment of this aspect of the present invention relates to a compound according to the first aspect of the present invention for the treatment and/or prophylaxis of inflammatory disorders of the skin, in particular psoriasis as and/or eczema, most preferably psoriasis.

Another embodiment of this aspect of the present invention relates to a compound according to the first aspect of the present invention for the treatment and/or prophylaxis of chronic inflammatory disorders of the joints, in particular arthritis, rheumatoid arthritis and/or osteoarthritis arthritis, most preferably rheumatoid arthritis (RA).

Yet another embodiment of this aspect of the present invention relates to a compound according to the first aspect of the present invention for the treatment and/or prophylaxis of inflammatory bowel diseases, in particular Barrett's oesophagus, ileitis, ulcerative colitis and Crohn's disease.

Yet another embodiment of this aspect of the present invention relates to a compound according to the first aspect of the present invention for the treatment and/or prophylaxis of allogeneic or xenogeneic transplantation graft rejection, in particular transplantation grafts of cells, stem cells, tissues and/or organs.

Yet another embodiment of this aspect of the present invention relates to a compound according to the first aspect of the present invention for the treatment and/or prophylaxis of autoimmune diseases of the central and peripheral nervous system, in particular multiple sclerosis, myasthenia gravis and/or Eaton-Lambert Myasthenic syndrome, most preferably multiple sclerosis.

Yet another embodiment of this aspect of the present invention relates to a compound according to the first aspect of the present invention for the treatment and/or prophylaxis of inflammatory lung disorders, in particular asthma, acute respiratory distress syndrome, acute lung injury, chronic obstructive pulmonary disease, bronchiectasis and/or cystic fibrosis, most preferably asthma.

Yet another embodiment of this aspect of the present invention relates to a compound according to the first aspect of the present invention for the treatment and/or prophylaxis of allergies, in particular allergic rhinitis.

Another aspect of the present invention provides the use of at least one compound according to the present invention for the preparation of a pharmaceutical composition for the treatment and/or prophylaxis of one or more of the above mentioned diseases and/or disorders.

One embodiment of the invention provides the use of at least one compound according to the present invention for the preparation of a pharmaceutical composition for the treatment and/or prophylaxis of one or more of the diseases and/or disorders, selected from the group consisting of inflammatory disorders and/or autoimmune diseases and/or allergic disorders, preferably selected from the group consisting of psoriasis and/or psoriatic arthritis; rheumatoid arthritis; inflammatory bowel disease; asthma and allergic rhinitis.

Another aspect of the present invention is a method for the treatment and/or prophylaxis, in particular for of one or more of the above mentioned diseases and/or disorders,
in a mammal, in particular in a human, in need of treatment and/or prophylaxis of the respective disease and/or disorder, which comprises the administration of an effective amount of at least one compound according the present invention or the administration of a pharmaceutical composition according to the invention to the mammal.

One embodiment of the invention is a method for the treatment and/or prophylaxis of disorders and/or diseases, selected from the group consisting of inflammatory disorders and/or autoimmune diseases and/or allergic disorders, preferably selected from the group consisting of psoriasis and/or psoriatic arthritis; rheumatoid arthritis; inflammatory bowel disease; asthma and allergic rhinitis, in a mammal, in particular in a human, in need of treatment and/or prophylaxis of the respective disease and/or disorder, which comprises the administration of an effective amount of at least one compound according the present invention or the administration of a pharmaceutical composition according to the invention to the mammal.

The term "effective amount" according to the present invention means that administered amount of the compound or the pharmaceutical composition that will result in a therapeutically desired biological or medical response of a tissue, system, mammal or human.

A therapeutically desired biological or medical response is understood to be an improved treatment, healing, prevention, or amelioration of a disease, disorder, or side effect, or a decrease in the rate of advancement of a disease or disorder in a mammal, as compared to a corresponding mammal who has not been administered such amount. The term "therapeutically desired biological or medical response" includes also the enhancement of a normal physiological function.

The term "compounds according to the first aspect of the present invention" in foregoing aspects of the invention encompasses all possible stereoisomers and tautomers as well as the respective corresponding acids, bases, salts and solvates.

The embodiments and in particular the preferred embodiments of any aspect of the present invention apply to all other aspects of the inventions respectively.

Preparation Schemes

Compounds of the invention may be made by the methods depicted in the reaction schemes below and described for examples of the invention. The following reaction schemes are illustrative only and various modifications of the methods may be made by those skilled in the art in order to obtain compounds of the invention.

Scheme 1:

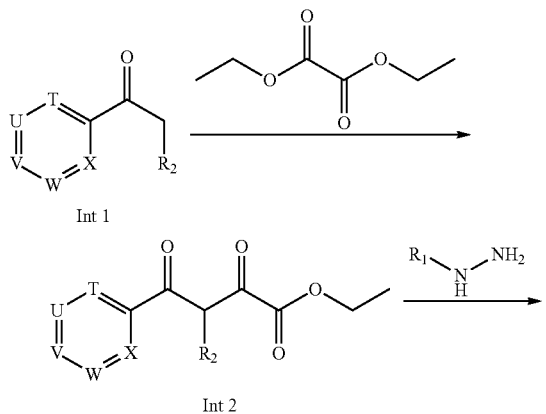

-continued

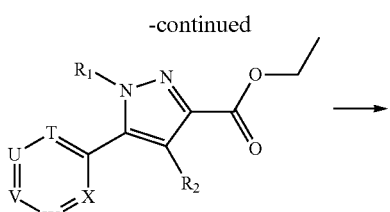

Int 3

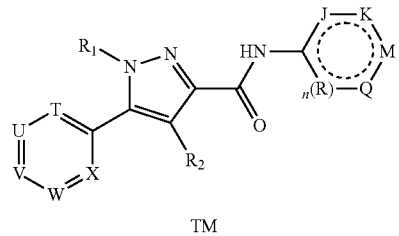

TM

Condensation of an appropriate aryl alkyl ketone with a glyoxalate diester as diethyl glyoxalate yields a β-ketone intermediate that readily cyclises upon treatment with a suitably substituted hydrazine to afford the aryl pyrazole ethyl ester as a mixture of isomers. After separation of the isomers, for instance by flash chromatography, transformation of the ester into compounds of the invention can be performed via saponification and amide coupling by one of the various methods known to those skilled in the art or a conventional one step method (Scheme 1). Alternatively, as shown in Scheme 1a cyclisation of the β-ketone intermediate can be performed with unsubstituted hydrazine. Alkylation with suitable halogenides or equivalents again leads to substituted aryl pyrazole ethyl ester derivatives. Separation of isomers and subsequent steps follow the route depicted in Scheme 1.

Scheme 1a:

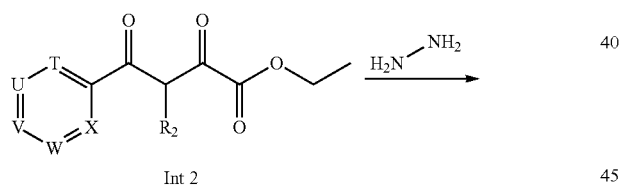

Int 2

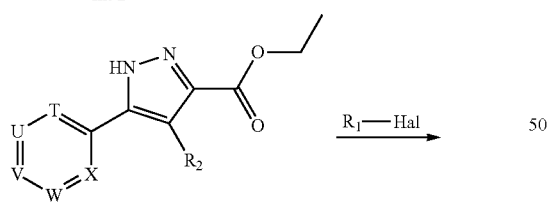

Int 4

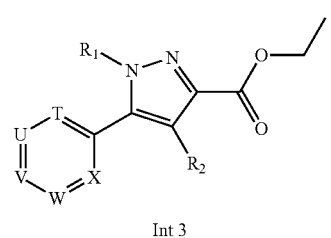

Int 3

Substitutions $R_2 \neq H$ may be introduced on stage of the ketone starting material (as shown in Scheme 1, e.g. $R_2=CH_3$), the 3-ketone intermediate or the aryl pyrazole ester (e.g. $R_2=C_1$, $NO_2$ as shown in Scheme 1b) or at any other suitable stage of the synthesis optionally followed by further modifications (e.g. reduction of $NO_2$ to $NH_2$ with an appropriate reagent on this or later stage). Subsequent steps may then follow the route depicted in Scheme 1. In particular cases a protecting group may be employed.

Scheme 1b:

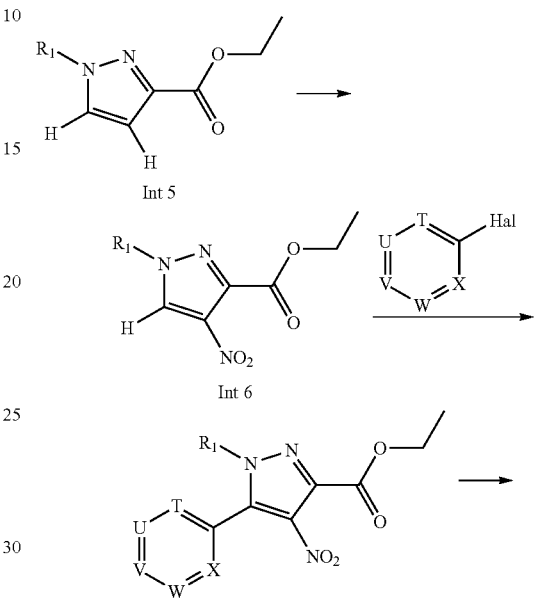

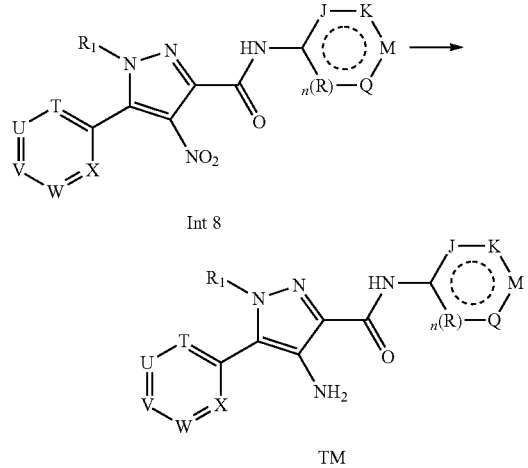

TM

As shown in Scheme 2 and 3 alternatively Pd-catalyzed coupling methods may be used to obtain compounds of the invention. Scheme 3 illustrates the synthesis via a pyrazole bromide or triflate employed in a Suzuki cross coupling with an appropriate boronic acid or ester. The coupling may also be performed on a pyrazole ester intermediate. Scheme 5 provides an example how a 5-unsubstituted pyrazole ester is converted into a boronic ester in the presence of an iridium catalyst and bispinacolato-diborane. Suzuki coupling with an appropriate aryl halogenide or triflate subsequently gives aryl pyrazole esters that can be converted to compounds of the invention as shown in Scheme 1. A direct coupling of the 5-unsubstituted pyrazole with an aryl halogenide may provide an alternative synthesis strategy for aryl pyrazole ester formation.

Scheme 2:

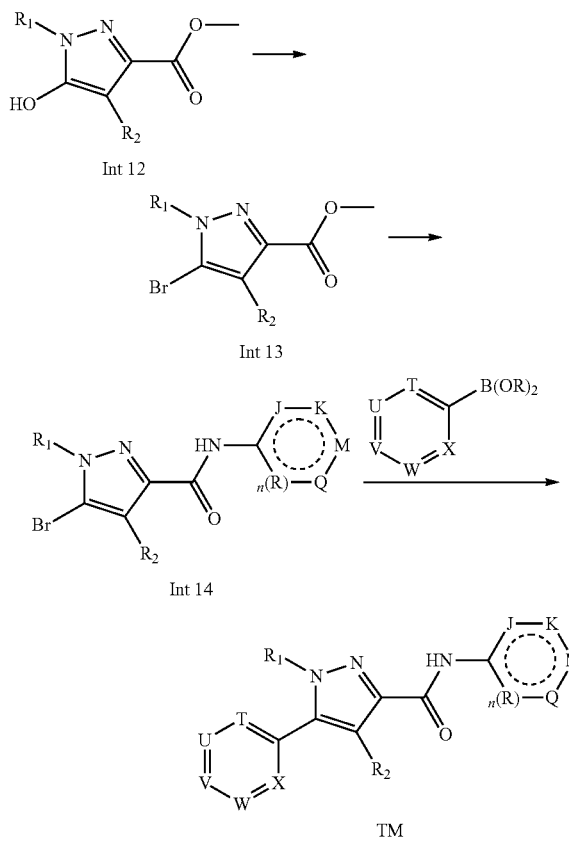

Int 12

Int 13

Int 14

TM

Scheme 3:

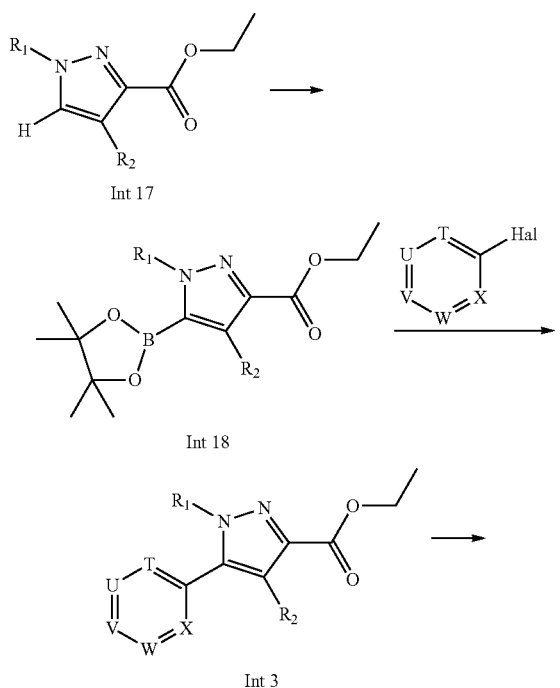

Int 17

Int 18

Int 3

-continued

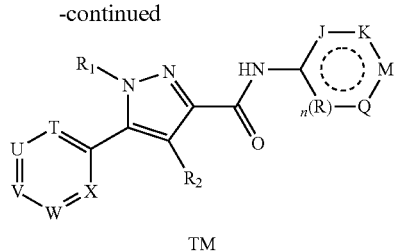

TM

In general, further modifications may be performed on aryl pyrazole amides or esters readily assembled according to the synthesis schemes provided above. For instance a halogen substitution, preferably Br or I, in the position T, U, V, W or X may be transformed by a Pd catalyzed coupling as Suzuki, Stille and Negishi, or alternatively undergo a Buchwald coupling to afford compounds of the invention or their ester intermediates (Scheme 4). Other examples include the use of a carboxylic acid, ester or nitrile for further modifications and other synthesis transformation known to those skilled in the art.

Scheme 4:

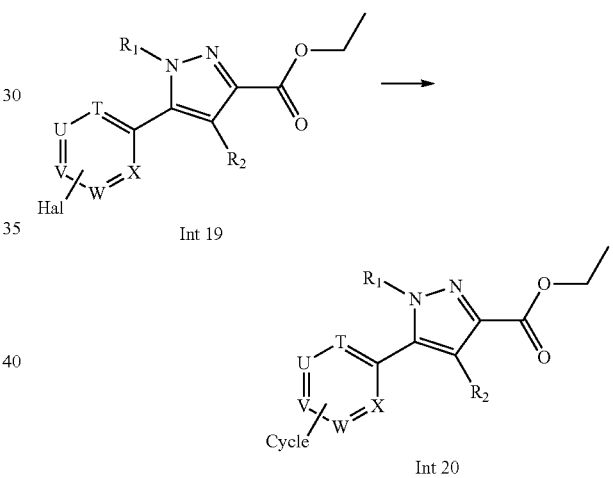

Int 19

Int 20

Exemplified Compounds

The following examples of the invention were prepared according to reaction schemes 1 to 4.

Starting materials and reagents are available from commercial suppliers such as for example Acros, Aldrich, Apollo, Fluka, FluoroChem, Lancaster, Manchester Organics, MatrixScientific, Maybridge, Merck, TCI, Oakwood, etc., or the synthesis has been described as such in the literature or the materials may be prepared by conventional methods known to those skilled in the art.

All the intermediate products and exemplary compounds were analytically characterized by means of $^1$H-NMR spectroscopy. In addition, mass spectrometry tests (MS, m/z for $[M+H]^+$) were carried out for all the exemplary compounds and selected intermediate products.

Abbreviations

The indication "equivalents" ("eq." or "eq" or "equiv.") means molar equivalents, "RT" or "rt" means room temperature ($23\pm7°$ C.), "M" are indications of concentration in mol/l, "aq." means aqueous, "sat." means saturated, "sol." means solution, "conc." means concentrated.

Further Abbreviations

Cy cyclohexane

DCM dichloromethane

DMF N,N-dimethylformamide

EDC.HCl N-(3-dimethylaminopropyl)-N'-ethylcarbodiimide hydrochloride

Et$_2$O diethyl ether

EtOH ethanol

EtOAc ethyl acetate h hour(s)

HATU 1-[bis(dimethylamino)methylene]-1H-1,2,3-triazolo[4,5-b]pyridinium 3-oxid hexafluorophosphate HOBT 1-hydroxybenzotriazole MeOH methanol min minute(s)

PEPPSI™-Ipr [1,3-bis(2,6-Diisopropylphenyl)imidazol-2-ylidene](3-chloropyridyl)palladium(I) dichloride Pd(dppf)Cl$_2$.CH$_2$Cl$_2$ [1,1'-bis(diphenylphosphino)ferrocene]dichloropalladium(II), complex with dichloromethane THF tetrahydrofuran Analytical and Purification Methods:

The mixing ratios of solvents or eluents for chromatography are specified in v/v.

Liquid Chromatography with Mass Spectrometry Detection: LC-MS

Method 1:

Agilent LC-MS 1200 Rapid Resolution with detector MSD6140

Detection: MM-ES+APCl+DAD (254 nm)

Fragmentation: 50 V [pos/neg]

Column: Agilent SB-C18, 2.1×30 mm, 3.5 micron

Column temperature: 30° C.

Flow rate: 0.8 mL/min.

Runtime: 4 min.

Eluent: A: Water; B: methanol with 1 vol-% formic acid

Gradient: t=0 min.: 95/5 (A/B)

t=1.00 min.: 95/5 (A/B)

t=4.00 min.: 0/100 (A/B)

Method 2:

Agilent 1290 Infinity UHPLC-TOF system

Detection: Agilent G4212A DAD (190-400 nm)+Agilent 6224 TOF

Column: Zorbax SB-C18 Rapid Resolution HD, 2.1×50 mm

Column temperature: 80° C.

Flow rate: 2.3 mL/min

Runtime: 1.38 min.

Eluent: A: Water with 0.1 vol-% formic acid; B: acetonitrile with 0.1 vol-% formic acid Gradient: t=0 min.: 98/2 (A/B)

t=1.20 min.: 0/100 (A/B)

t=1.29 min.: 0/100 (A/B)

t=1.31 min.: 98/2 (A/B)

t=1.38 min.: 98/2 (A/B)

Chromatography

Büchi MPLC system; Stationary phase: silica gel, 40-50μ

PuriFlash 43; Stationary phase: Interchim®-cartridges

SYNTHESIS EXAMPLE 1

N-(3-Fluoro-pyridin-4-yl)-1-methyl-5-(2-methyl-5-thiazol-2-yl-phenyl)-1H-pyrazole-3-carboxylic acid amide Intermediate 1a)

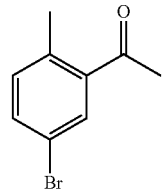

To a suspension of magnesium (1.44 g) in dry Et$_2$O (50 mL) methyl iodide (8.4 g) in dry Et$_2$O (10 mL) was added and the reaction mixture stirred for 2 h at rt. Subsequent addition of 5-bromo-2-methyl-benzonitrile (4 g) was followed by 4 h at reflux before the mixture was quenched with saturated aqueous ammonium chloride solution at 0° C. EtOAc was added. After phase separation the organic layer was dried over sodium sulfate and the solvent removed under reduced pressure. The residual was taken up in ice and concentrated sulfuric acid and stirred for 68 h at rt. The mixture was extracted with EtOAc and the phases separated. The organic layer was washed with water, dried and concentrated under reduced pressure. The crude material was purified by chromatography with Cy/EtOAc 9:1 to furnish the desired product (74% yield).

LC-MS (Method 1): R$_t$=3.52 min.

Intermediate 1b

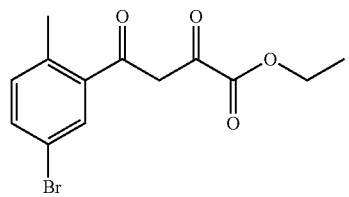 [SMILES: CCOC(=O)C(=O)CC(=O)c1cc(Br)ccc1C]

Sodium (349 mg) was dissolved in dry ethanol (20 mL) and subsequently solutions of diethyl oxalate (2.22 g) in Et$_2$O (10 mL) and intermediate 1a (3.23 g) in Et$_2$O (10 mL) were added. The reaction mixture was stirred at rt for 20 h followed by addition of 2N aqueous HCl (40 mL) and extraction with EtOAc. The combined organic layers were dried and the solvent removed under reduced pressure to yield crude material of the desired product (84% yield).

LC-MS (Method 1): R$_t$=4.0 min.

Intermediate 1c

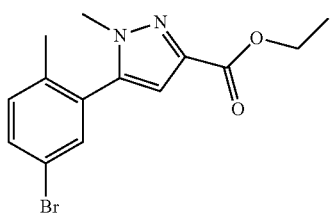 [SMILES: CCOC(=O)c1cc(-c2cc(Br)ccc2C)n(C)n1]

To a solution of intermediate 1b (2.51 g) in EtOH (50 mL) methyl hydrazine (369 mg) was added at 0° C. and the reaction mixture stirred for 1 h at rt. The solvent was removed under reduced pressure and the remaining material dissolved in EtOAc. The resulting solution was washed with water, dried and concentrated under reduced pressure. Purification by chromatography (SiO$_2$, Cy/EtOAc) yielded the desired product. (54% yield).

LC-MS (Method 1): m/z [M+H]$^+$=323.1 (MW calc.=323.19); R$_t$=3.83 min.

Intermediate 1d

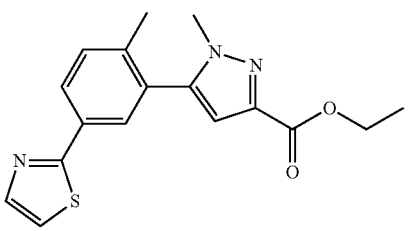 [SMILES: CCOC(=O)c1cc(-c2cc(-c3nccs3)ccc2C)n(C)n1]

A solution of intermediate 1c (1.37 g), 2-(tri-n-butylstannyl)thiazole (1.64 mL) and bis(triphenylphosphine)-palladium (II) chloride (184 mg) in acetonitrile (10 mL) was stirred at 90° C. for 5 h. The solvent was removed under reduced pressure and the remaining material purified by column chromatography (silica gel, potassium carbonate, Cy/EtOAc) to yield the desired product (28% yield).

LC-MS (Method 1): m/z [M+H]$^+$=328.2 (MW calc.=327.40); R$_t$=3.68 min.

Intermediate 1e

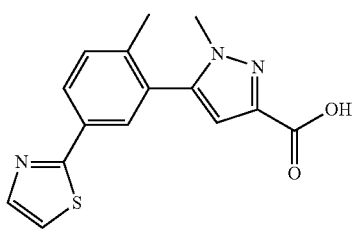 [SMILES: Cc1ccc(-c2nccs2)cc1-c1cc(C(=O)O)nn1C]

A solution of intermediate 1d (340 mg) in ethanol (10 mL) was treated with sodium hydroxide (208 mg) and was stirred at 80° C. for 2 h. The solvent was removed under reduced pressure and the residue was diluted in 2N HCl and was extracted with EtOAc. The combined organic layers were washed with water, dried and the solvents were removed under reduced pressure to yield the desired product (96% yield).

LC-MS (Method 1): m/z [M+H]$^+$=300.2 (MW calc.=299.35); R$_t$=3.40 min.

N-(3-Fluoro-pyridin-4-yl)-1-methyl-5-(2-methyl-5-thiazol-2-yl-phenyl)-1H-pyrazole-3-carboxylic acid amide (Example 1)

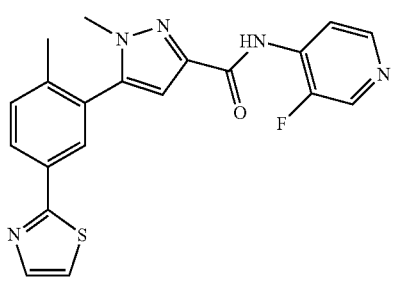

To a solution of intermediate 1e (293 mg) and 3-fluoropyridin-4-amine (101 mg) in dry N,N-dimethyl formamide (20 mL) were consecutively added O-(7-Aza-1H-benzotriazole-1-yl)-N,N,N',N'-tetramethyluronium hexafluorophosphate (342 mg) and triethylamine (250 µL) and the mixture was stirred at rt for 2 h. The solution was concentrated under reduced pressure and was diluted in 1N NaOH and extracted with DCM. The combined organic layers were dried and the solvent was removed under reduced pressure. The residue was purified by column chromatography (Interchim® cartridge 15SiHP/12 g, Cy/EtOAc) to yield the title compound of example 1 (42% yield).

LC-MS (Method 2): m/z [M+H]$^+$=394.11 (MW calc.=393.44); R$_t$=0.66 min.

SYNTHESIS EXAMPLE 2

N-(3-Fluoro-pyridin-4-yl)-1-methyl-5-(2-methyl-5-oxazol-2-yl-phenyl)-1H-pyrazole-3-carboxylic acid amide Intermediate 2a

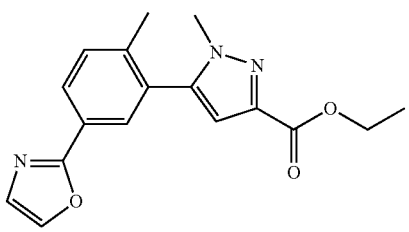 [SMILES: CCOC(=O)c1cc(-c2cc(-c3ncco3)ccc2C)n(C)n1]

A solution of intermediate 1c, 2-(tri-n-butylstannyl)oxazole (251 µL) and bis(triphenylphosphine) (II) dichloride in dry acetonitrile (10 mL) was stirred under an argon atmosphere at 90° for 5 h. The reaction mixture was concentrated under reduced pressure and the residue was purified by column chromatography (silica gel, potassium carbonate, Cy/EtOAc) to yield the desired product (45% yield).

Intermediate 2b

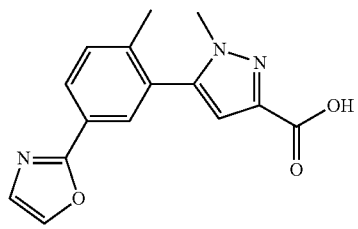 [SMILES: Cc1ccc(-c2ncco2)cc1-c1cc(C(=O)O)nn1C]

A solution of intermediate 2a (320 mg) in ethanol (10 mL) was treated with sodium hydroxide (206 mg) and was stirred at 80° C. for 2 h. The solvent was removed under reduced pressure and the residue was diluted in 2N HCl and was extracted with EtOAc. The combined organic layers were washed with water, dried and the solvents were removed under reduced pressure to yield the desired product (96% yield).

N-(3-Fluoro-pyridin-4-yl)-1-methyl-5-(2-methyl-5-oxazol-2-yl-phenyl)-1H-pyrazole-3-carboxylic acid amide (Example 2)

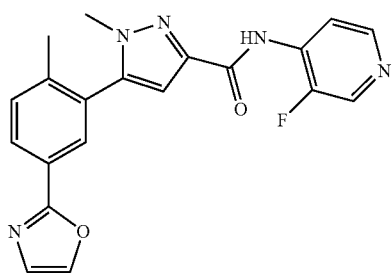

To a solution of intermediate 2b (280 mg) and 3-fluoropyridin-4-amine (121 mg) in dry DMF (20 mL) were consecutively added O-(7-Aza-1H-benzotriazole-1-yl)-N,N,N',N'-tetramethyluronium hexafluorophosphate (376 mg) and triethylamine (138 µL) and the mixture was stirred at rt for 20 h. The solution was concentrated under reduced pressure and was diluted in 1N NaOH and extracted with EtOAc. The combined organic layers were dried and the solvent was removed under reduced pressure. The residue was purified by column chromatography (Interchim® cartridge 15SiHP/12 g, DCM/MeOH) to yield the title compound of example 2 (27% yield).

LC-MS (Method 2): m/z $[M+H]^+$=378.14 (MW calc.=377.37); $R_t$=0.69 min.

SYNTHESIS EXAMPLE 3

N-(2,6-Difluoro-phenyl)-1-methyl-5-(2-methyl-5-thiazol-2-yl-phenyl)-1H-pyrazole-3-carboxylic acid amide

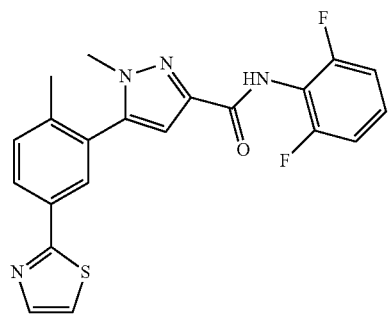

To a solution of intermediate 1e (299 mg) and 2,6-difluoroaniline (129 mg) in dry DMF (10 mL) were consecutively added O-(7-Aza-1H-benzotriazole-1-yl)-N,N,N',N'-tetramethyluronium hexafluorophosphate (380 mg) and triethylamine (250 µL) and the mixture was stirred at rt for 70 h. The solution was concentrated under reduced pressure and was diluted in 1N NaOH and extracted with DCM. The combined organic layers were dried and the solvent was removed under reduced pressure. The residue was purified by column chromatography (silica gel, 12 g, Cy/EtOAc) to yield the title compound of example 3 (14% yield).

LC-MS (Method 2): m/z $[M+H]^+$=411.11 (MW calc.=410.44); $R_t$=0.77 min.

SYNTHESIS EXAMPLE 4

N-(4-Methoxyphenyl)-1-methyl-5-(2-methyl-5-thiazol-2-yl-phenyl)-1H-pyrazole-3-carboxylic acid amide To a solution of intermediate 1e (449 mg) and 4-methoxyaniline (185 mg) in dry DMF (10 mL) were consecutively added O-(7-Aza-1H-benzotriazole-1-yl)-N,N,N',N'-tetramethyluronium hexafluorophosphate (380 mg) and triethylamine (250 µL) and the mixture was stirred at rt for 70 h. The solution was concentrated under reduced pressure and was diluted in 1N NaOH and extracted with DCM. The combined organic layers were dried and the solvent was removed under reduced pressure. The residue was purified by column chromatography (silica gel, Cy/EtOAc) to yield the title compound of example 4 (84% yield).

LC-MS (Method 2): m/z [M+H]+=405.14 (MW calc.=404.48); R$_t$=0.79 min.

SYNTHESIS EXAMPLE 5

N-(4-Fluorophenyl)-1-methyl-5-(2-methyl-5-thiazol-2-yl-phenyl)-1H-pyrazole-3-carboxylic acid amide

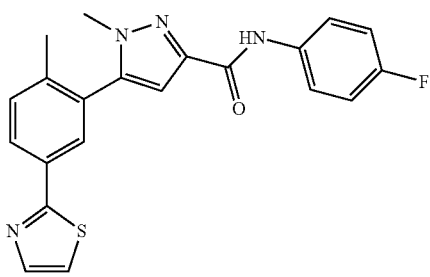 [SMILES: Cc1ccc(-c2nccs2)cc1-c1cc(C(=O)Nc2ccc(F)cc2)nn1C]

To a solution of intermediate 1e (299 mg) and 4-fluoroaniline (111 mg) in dry DMF (10 mL) were consecutively added O-(7-Aza-1H-benzotriazole-1-yl)-N,N,N',N'-tetramethyluronium hexafluorophosphate (380 mg) and triethylamine (279 µL) and the mixture was stirred at ambient temperature for 20 h. The solution was concentrated under reduced pressure and was diluted in 1N NaOH and extracted with DCM. The combined organic layers were dried and the solvent was removed under reduced pressure. The residue was purified by column chromatography (silica gel, Cy/EtOAc) to yield the title compound of example 5 (72% yield).

LC-MS (Method 2): m/z [M+H]+=393.12 (MW calc.=392.45); R$_t$=0.81 min.

SYNTHESIS EXAMPLE 6

1-Methyl-N-(3-methyl-pyridin-4-yl)-5-(2-methyl-5-thiazol-2-yl-phenyl)-1H-pyrazole-3-carboxylic acid amide

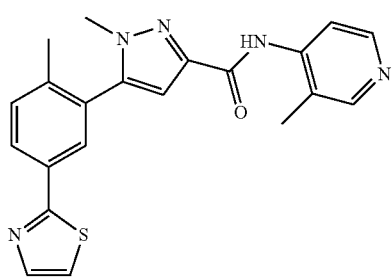 [SMILES: Cc1cnccc1NC(=O)c1cc(-c2cc(-c3nccs3)ccc2C)n(C)n1]

To a solution of intermediate 1e (150 mg) and 3-methylpyridin-4-amine (54 mg) in dry DMF (10 mL) were consecutively added O-(7-Aza-1H-benzotriazole-1-yl)-N,N,N',N'-tetramethyluronium hexafluorophosphate (380 mg) and triethylamine (139 µL) and the mixture was stirred at rt for 20 h. The solution was concentrated under reduced pressure and was diluted in 1N NaOH and extracted with DCM. The combined organic layers were dried and the solvent was removed under reduced pressure. The residue was purified by column chromatography (Interchim® cartridge 15SiHP/25 g, DCM/methanol) followed by crystallization (chloroform/heptane) to yield the title compound of example 6 (29% yield).

LC-MS (Method 2): m/z [M+H]+=390.14 (MW calc.=389.47); R$_t$=0.55 min.

SYNTHESIS EXAMPLE 7

N-(3-Fluoro-pyridin-4-yl)-5-(2-methoxy-5-thiazol-2-yl-phenyl)-1-methyl-1H-pyrazole-3-carboxylic acid amide Intermediate 7a

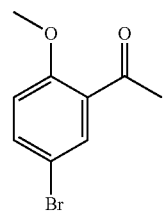

Potassium carbonate (9.6 g) was added to a solution of 1-(5-bromo-2-hydroxyphenyl)ethanone (4.98 g) in acetone (50 mL) and the suspension was stirred at rt for 1 h. Methyl iodide (1.89 mL) was added and the reaction mixture was stirred at rt for 20 h at which time it was filtered and the volatiles were removed under reduced pressure. The residue was diluted in Et$_2$O and was washed with water. The organic layer was dried and the solvent was removed under reduced pressure to yield the desired product (91% yield).

LC-MS (Method 1): m/z [M+H]+=229.1 (MW calc.=229.07); R$_t$=3.30 min.

Intermediate 7b

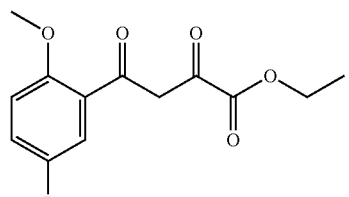

Sodium (533 mg) was dissolved in dry EtOH (20 mL) and subsequently solutions of diethyl oxalate (3.39 g) in dry Et$_2$O (10 mL) and intermediate 7a (4.83 g) in Et$_2$O (10 mL) were added. The reaction mixture was stirred at rt for 20 h followed by addition of 2N aqueous HCl (40 mL) and extraction with EtOAc. The combined organic layers were dried and the solvent removed under reduced pressure to yield crude material of the desired product (98% yield).

LC-MS (Method 1): m/z [M+H]+=329.1 (MW calc.=329.14); R$_t$=3.90 min.

Intermediate 7c

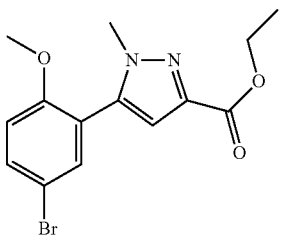 [SMILES: CCOC(=O)c1cc(-c2cc(Br)ccc2OC)n(C)n1]

To a solution of intermediate 7b (6.28 g) in ethanol (250 mL) methyl hydrazine (878 mg) was added at 0° C. and the reaction mixture stirred for 1 h at rt. The solvent was removed under reduced pressure and the remaining material dissolved in EtOAc. The resulting solution was washed with water, dried and concentrated under reduced pressure. Purification and by chromatography (SiO$_2$, Cy/EtOAc) yielded the desired product (17% yield).

LC-MS (Method 1): m/z [M+H]$^+$=339.1 (MW calc.=339.18); R$_t$=3.70 min.

Intermediate 7d

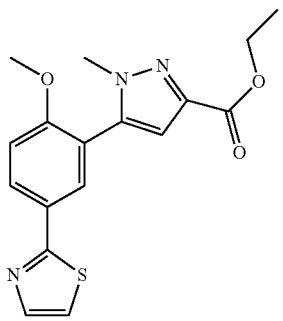 [SMILES: CCOC(=O)c1cc(-c2cc(-c3nccs3)ccc2OC)n(C)n1]

Sodium carbonate (316 mg), bis(triphenylphosphine)palladium (II) chloride (167 mg) and a 2-thiazolylzinc bromide solution (0.5 M in THF, 6 mL) were consecutively added to a solution of intermediate 7c (1.01 g) in dry THF (15 mL) under an argon atmosphere and the reaction mixture was stirred at 120° C. for 1 h. After addition of saturated ammonium chloride solution (10 mL) the mixture was extracted with DCM, dried and the volatiles were removed under reduced pressure. The residue was purified by column chromatography (SiO$_2$, Cy/EtOAc) to yield the desired product (32% yield).

LC-MS (Method 1): m/z [M+H]$^+$=344.2 (MW calc.=343.40); R$_t$=3.60 min.

Intermediate 7e

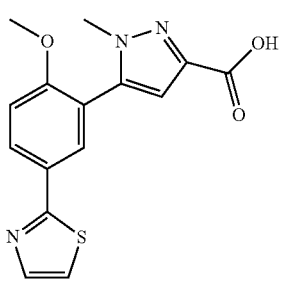 [SMILES: COc1ccc(-c2nccs2)cc1-c1cc(C(=O)O)nn1C]

A solution of intermediate 7d (330 mg) in EtOH (15 mL) was treated with sodium hydroxide (192 mg) and was stirred at 80° C. for 2 h. The solvent was removed under reduced pressure and the residue was diluted in 2N HCl and was extracted with EtOAc. The combined organic layers were washed with water, dried and the solvents were removed under reduced pressure to yield the desired product (96% yield).

LC-MS (Method 1): m/z [M+H]$^+$=316.2 (MW calc.=315.35); R$_t$=3.20 min.

N-(3-Fluoro-pyridin-4-yl)-5-(2-methoxy-5-thiazol-2-yl-phenyl)-1-methyl-1H-pyrazole-3-carboxylic acid amide (Example 7)

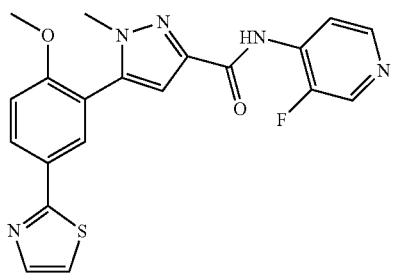 [SMILES: COc1ccc(-c2nccs2)cc1-c1cc(C(=O)Nc2ccncc2F)nn1C]

A solution of intermediate 7e (105 mg) in thionyl chloride (2 mL) was stirred at 50° C. for 30 min. The volatiles were removed under reduced pressure and the residue was dissolved in DCM. 3-fluoropyridin-4-amine (45 mg) and triethylamine (138 µL) were added to this solution and the mixture was stirred for 2 h at rt. Water was added, the layers were separated and the organic layer was dried and the volatiles were removed under reduced pressure. The residue was purified by chromatography (SiO$_2$, EtOAc) to yield the title compound of example 7 (46% yield).

LC-MS (Method 2): m/z [M+H]$^+$=410.10 (MW calc.=409.44); R$_t$=0.72 min.

SYNTHESIS EXAMPLE 8

N-(2,6-Difluoro-phenyl)-5-(2-methoxy-5-thiazol-2-yl-phenyl)-1-methyl-1H-pyrazole-3-carboxylic acid amide

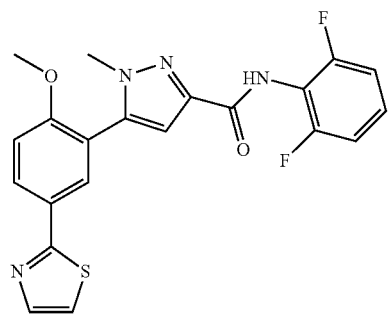 [SMILES: COc1ccc(-c2nccs2)cc1-c1cc(C(=O)Nc2c(F)cccc2F)nn1C]

A solution of intermediate 7e (105 mg) in thionyl chloride (2 mL) was stirred at 50° C. for 30 min. The volatiles were removed under reduced pressure and the residue was dissolved in DCM. 2,6-difluoro-aniline (41 µL) and triethylamine (138 µL) were added to this solution and the mixture was stirred for 2 h at rt. Water was added, the layers were separated and the organic layer was dried and the volatiles were removed under reduced pressure. The residue was purified by chromatography (SiO$_2$, Cy/EtOAc) to yield the title compound of example 8 (44% yield).

LC-MS (Method 2): m/z [M+H]$^+$=427.10 (MW calc.=426.44); R$_t$=0.75 min.

SYNTHESIS EXAMPLE 9

5-(2-Chloro-5-thiazol-2-yl-phenyl)-N-(3-fluoro-pyridin-4-yl)-1-methyl-1H-pyrazole-3-carboxylic acid amide Intermediate 9a

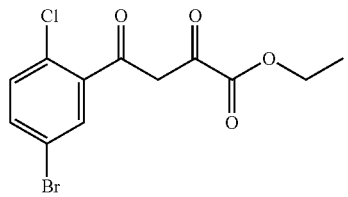 [SMILES: CCOC(=O)C(=O)CC(=O)c1cc(Br)ccc1Cl]

Sodium (561 mg) was dissolved in dry EtOH (20 mL) and subsequently solutions of diethyl oxalate (3.57 g) in dry Et$_2$O (10 mL) and 1-(5-bromo-2-chlorophenyl)ethanone (5.00 g) in Et$_2$O (10 mL) were added. The reaction mixture was stirred at rt for 20 h followed by addition of 2N aqueous HCl (40 mL) and extraction with EtOAc. The combined organic layers were dried and the solvent removed under reduced pressure to yield crude material of the desired product (97% yield).

LC-MS (Method 1): m/z [M+H]$^+$=333.0 (MW calc.=333.56); R$_t$=3.90 min.

Intermediate 9b

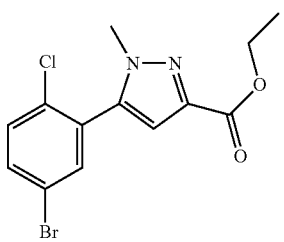 [SMILES: CCOC(=O)c1cc(-c2cc(Br)ccc2Cl)n(C)n1]

To a solution of intermediate 9a (6.89 g) in ethanol (140 mL) methyl hydrazine (951 mg) was added at 0° C. and the reaction mixture stirred for 20 h at rt. The volatiles were removed under reduced pressure and the residue was purified by chromatography (SiO$_2$, Cy/EtOAc) to yield the desired product (55% yield).

LC-MS (Method 1): m/z [M+H]$^+$=343.1 (MW calc.=343.60); R$_t$=3.80 min.

Intermediate 9c

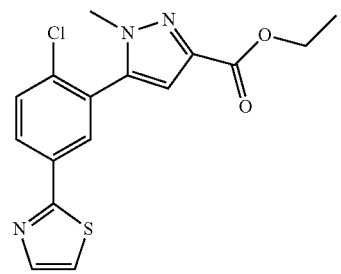 [SMILES: CCOC(=O)c1cc(-c2cc(-c3nccs3)ccc2Cl)n(C)n1]

A solution of intermediate 9b (1.31 g), 2-(tri-n-butylstannyl)thiazole (1.32 mL) and bis(triphenylphosphine)-palladium (II) chloride (134 mg) in dry acetonitrile (15 mL) was stirred at 90° C. for 1 h. The solvent was removed under reduced pressure and the remaining material purified by column chromatography (silica gel, potassium carbonate, Cy/EtOAc) to yield the desired product (63% yield).

LC-MS (Method 1): m/z [M+H]$^+$=348.2 (MW calc.=347.82); R$_t$=3.70 min.

Intermediate 9d

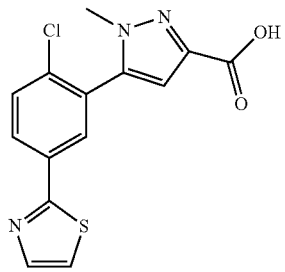 [SMILES: Cn1nc(C(=O)O)cc1-c1cc(-c2nccs2)ccc1Cl]

A solution of intermediate 9c (832 mg) in EtOH (15 mL) was treated with sodium hydroxide (478 mg) and was stirred at 80° C. for 2 h. The solvent was removed under reduced pressure and the residue was diluted in 2N HCl and was extracted with EtOAc. The combined organic layers were washed with water, dried and the solvents were removed under reduced pressure to yield the desired product (99% yield).

LC-MS (Method 1): m/z [M+H]$^+$=320.1 (MW calc.=319.77); R$_t$=3.40 min.

5-(2-Chloro-5-thiazol-2-yl-phenyl)-N-(3-fluoro-pyridin-4-yl)-1-methyl-1H-pyrazole-3-carboxylic acid amide (Example 9)

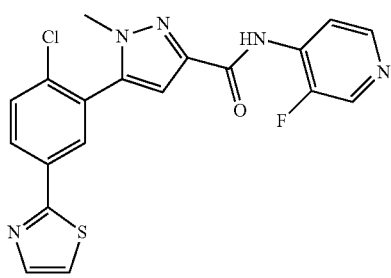 [SMILES: Cn1nc(C(=O)Nc2ccncc2F)cc1-c1cc(-c2nccs2)ccc1Cl]

A solution of intermediate 9d (170 mg) in thionyl chloride (2 mL) was stirred at 50° C. for 30 min. The volatiles were removed under reduced pressure and the residue was dissolved in DCM. 3-fluoropyridin-4-amine (72 mg) and triethylamine (221 μL) were added to this solution and the mixture was stirred for 1 h at rt. Water was added, the layers were separated and the organic layer was dried and the volatiles were removed under reduced pressure. The residue was purified by chromatography (SiO$_2$, DCM/MeOH) to yield the title compound of example 9 (64% yield).

LC-MS (Method 2): m/z [M+H]$^+$=414.05 (MW calc.=413.86); R$_t$=0.78 min.

SYNTHESIS EXAMPLE 10

5-(2-Chloro-5-thiazol-2-yl-phenyl)-N-(2,6-difluorophenyl)-1-methyl-1H-pyrazole-3-carboxylic acid amide

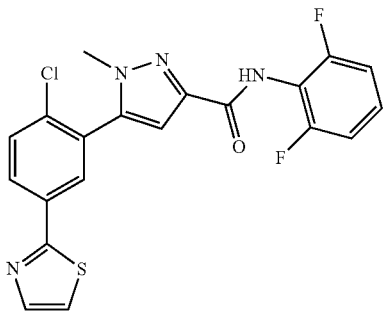 [SMILES: Cn1nc(C(=O)Nc2c(F)cccc2F)cc1-c1cc(-c2nccs2)ccc1Cl]

A solution of intermediate 9d (170 mg) in thionyl chloride (2 mL) was stirred at 50° C. for 30 min. The volatiles were removed under reduced pressure and the residue was dissolved in DCM. 2,6-difluoro-aniline (82 mg) and triethylamine (221 μL) were added to this solution and the mixture was stirred for 20 h at rt. Water was added, the layers were separated and the organic layer was dried and the volatiles were removed under reduced pressure. The residue was purified by chromatography (SiO$_2$, DCM/MeOH) to yield the title compound of example 10 (61% yield).

LC-MS (Method 2): m/z [M+H]$^+$=431.05 (MW calc.=430.86); R$_t$=0.80 min.

SYNTHESIS EXAMPLE 11

N-(3-Fluoro-pyridin-4-yl)-1-methyl-5-(2-methyl-5-pyridin-4-yl-phenyl)-1H-pyrazole-3-carboxylic acid amide Intermediate 11a

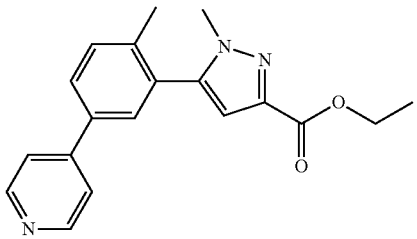 [SMILES: CCOC(=O)c1cc(-c2cc(-c3ccncc3)ccc2C)n(C)n1]

A solution of intermediate 1c (750 mg), 4-(4,4,5,5-tetramethyl-1,3,2-dioxaborolan-2-yl)pyridine (523 mg), cesium fluoride (705 mg) and tetrakis(triphenylphosphine)palladium (267 mg) in 1,2-dimethoxyethane (20 mL) was stirred under an argon atmosphere at 120° C. for 48 h. The volatiles were removed under reduced pressure, water was added and the mixture was extracted with EtOAc. The combined organic layers were dried and the volatiles were removed under reduced pressure. The residue was purified by chromatography (SiO$_2$, EtOAc) to yield the desired product (72% yield).

LC-MS (Method 1): m/z [M+H]$^+$=322.3 (MW calc.=321.37); R$_t$=2.9 min.

Intermediate 11b

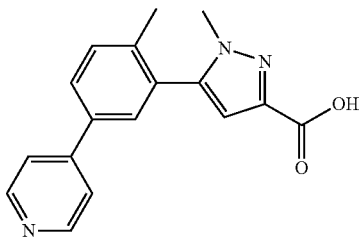 [SMILES: Cc1ccc(-c2ccncc2)cc1-c1cc(C(=O)O)nn1C]

A solution of intermediate 11a (537 mg) in ethanol (15 mL) was treated with sodium hydroxide (336 mg) and was stirred at 80° C. for 1 h. The solvent was removed under reduced pressure and the residue was diluted in 2N HCl and was extracted with EtOAc. The combined organic layers were washed with water, dried and the solvents were removed under reduced pressure to yield the desired product (67% yield).

LC-MS (Method 1): m/z [M+H]$^+$=294.2 (MW calc.=293.32); R$_t$=2.2 min.

N-(3-Fluoro-pyridin-4-yl)-1-methyl-5-(2-methyl-5-pyridin-4-yl-phenyl)-1H-pyrazole-3-carboxylic acid amide (Example 11)

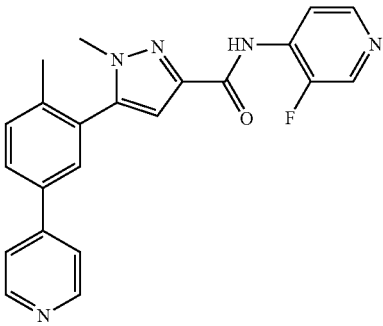 [SMILES: Cc1ccc(-c2ccncc2)cc1-c1cc(C(=O)Nc2ccncc2F)nn1C]

1-Chloro-N,N,2-trimethyl-1-propenylamine (55 mg) was added to a suspension of intermediate 11b (102 mg) in dry DCM (10 mL) and the mixture was stirred at rt for 1 h. 3-fluoropyridin-4-amine (44 mg) and triethyl amine were added and the mixture was stirred for 20 h at rt. Water was added, the layers separated and the organic layer was dried and the volatiles were removed under reduced pressure. The residue was purified by chromatography (Interchim® cartridge 30SiHP/25 g, DCM/MeOH) to yield the title compound of example 11 (39% yield).

LC-MS (Method 2): m/z [M+H]⁺=388.16 (MW calc.=387.41); R_t=0.51 min.

SYNTHESIS EXAMPLE 12

N-(2,6-Difluoro-phenyl)-1-methyl-5-(2-methyl-5-pyridin-4-yl-phenyl)-1H-pyrazole-3-carboxylic acid amide Intermediate 12a

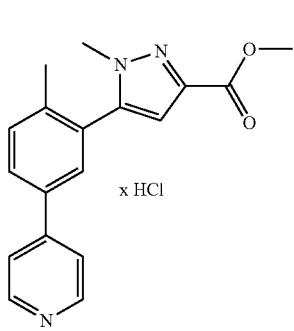 [SMILES: COC(=O)c1cc(-c2cc(-c3ccncc3)ccc2C)n(C)n1]

Thionyl chloride (210 μL) was added to a solution of intermediate 11b (170 mg) in MeOH (15 mL) and the mixture was heated to reflux for 1 h. The volatiles were removed under reduced pressure and the residue was washed with Et₂O to yield the desired product (88% yield).

LC-MS (Method 1): m/z [(M–HCl)+H]⁺=308.2 (MW (—HCl) calc.=307.35); R_t=3.0 min.

N-(2,6-Difluoro-phenyl)-1-methyl-5-(2-methyl-5-pyridin-4-yl-phenyl)-1H-pyrazole-3-carboxylic acid amide (Example 12)

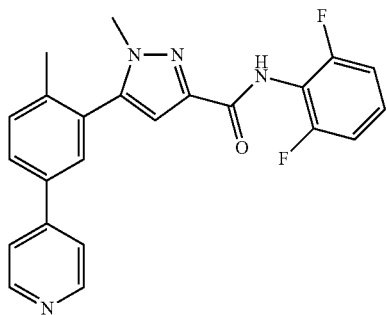 [SMILES: Cc1ccc(-c2ccncc2)cc1-c1cc(C(=O)Nc2c(F)cccc2F)nn1C]

2,6-difluoroaniline (62 μL) and trimethyl aluminum (2 M in heptane, 0.31 mL) were consecutively added to a suspension of intermediate 12a in toluene (5 mL) and the mixture was stirred at 110 C for 4 h. After cooling to rt, 1 M HCl (4 mL) was carefully added and the layers were separated. The aqueous layer was extracted with chloroform and the combined organic layers were dried and the volatiles were removed under reduced pressure. The residue was purified by chromatography (Interchim® cartridge 30SiHP/12 g, DCM/MeOH) to yield the title compound of example 12 (46% yield).

LC-MS (Method 2): m/z [M+H]⁺=405.15 (MW calc.=404.41); R_t=0.53 min.

SYNTHESIS EXAMPLE 13

N-(2,6-Difluoro-phenyl)-1-methyl-5-(2-methyl-5-pyrimidin-5-yl-phenyl)-1H-pyrazole-3-carboxylic acid amide Intermediate 13a

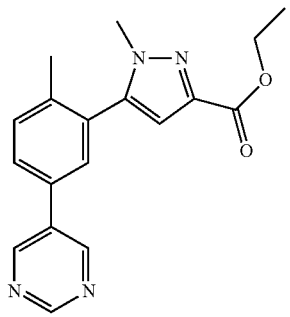 [SMILES: CCOC(=O)c1cc(-c2cc(-c3cncnc3)ccc2C)n(C)n1]

A solution of intermediate 1c (750 mg), 5-pyrimidineboronic acid pinacol ester (524 mg), cesium fluoride (705 mg) and tetrakis(triphenylphosphine)palladium (267 mg) in 1,2-dimethoxyethane (20 mL) was stirred under an argon atmosphere at 120° C. for 48 h. The volatiles were removed under reduced pressure, water was added and the mixture was extracted with EtOAc. The combined organic layers were dried and the volatiles were removed under reduced pressure. The residue was purified by chromatography (SiO₂, EtOAc) to yield the desired product (quantitative yield).

LC-MS (Method 1): m/z [M+H]⁺=323.3 (MW calc.=322.36); R_t=3.4 min.

N-(2,6-Difluoro-phenyl)-1-methyl-5-(2-methyl-5-pyrimidin-5-yl-phenyl)-1H-pyrazole-3-carboxylic acid amide (Example 13)

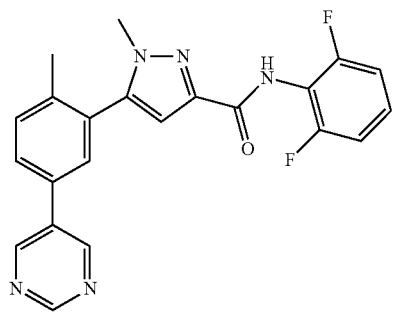 [SMILES: Cc1ccc(-c2cncnc2)cc1-c1cc(C(=O)Nc2c(F)cccc2F)nn1C]

2,6-difluoroaniline (56 μL) and trimethyl aluminum (2 M in heptane, 0.28 mL) were consecutively added to a suspension of intermediate 13a (152 mg) in toluene (5 mL) and the mixture was stirred at 110 C for 1 h. After cooling to rt, 1 M HCl (4 mL) was carefully added and the layers were separated. The aqueous layer was extracted with chloroform and the combined organic layers were dried and the volatiles were removed under reduced pressure. The residue was purified by chromatography (Interchim® cartridge 30SiHP/12 g, Cy/EtOAc) to yield the title compound of example 13 (34% yield).

LC-MS (Method 2): m/z [M+H]$^+$=406.15 (MW calc.=405.40); $R_t$=0.68 min.

SYNTHESIS EXAMPLE 14

N-(2,6-Difluoro-phenyl)-1-methyl-5-(3-thiazol-2-yl-phenyl)-1H-pyrazole-3-carboxylic acid amide Intermediate 14a

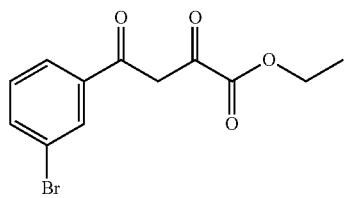 [SMILES: CCOC(=O)C(=O)CC(=O)c1cccc(Br)c1]

Sodium (634 mg) was dissolved in dry EtOH (35 mL) and subsequently solutions of diethyl oxalate (1.2 mL) in dry Et$_2$O (15 mL) and 3-bromo acetophenone (5.00 g) in Et$_2$O (10 mL) were added. The reaction mixture was stirred at rt for 15 min followed by addition of 2N aqueous HCl (40 mL) and extraction with EtOAc. The combined organic layers were dried and the solvent removed under reduced pressure to yield crude material of the desired product (91% yield).

Intermediate 14b

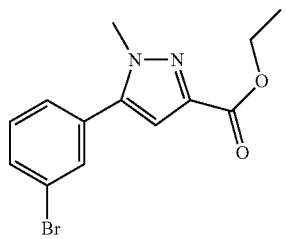 [SMILES: CCOC(=O)c1cc(-c2cccc(Br)c2)n(C)n1]

To a solution of intermediate 14a (300 mg) in EtOH (4 mL) concentrated HCl (150 mg) and methyl hydrazine (60 µL) were added reaction mixture stirred for 30 min at rt. The volatiles were removed under reduced pressure and the residue was purified by chromatography (Interchim® cartridge 50SiHP/25 g, Cy/EtOAc) to yield the desired product (20% yield).

LC-MS (Method 1): m/z [M+H]$^+$=309.1 (MW calc.=309.16); $R_t$=3.8 min.

Intermediate 14c

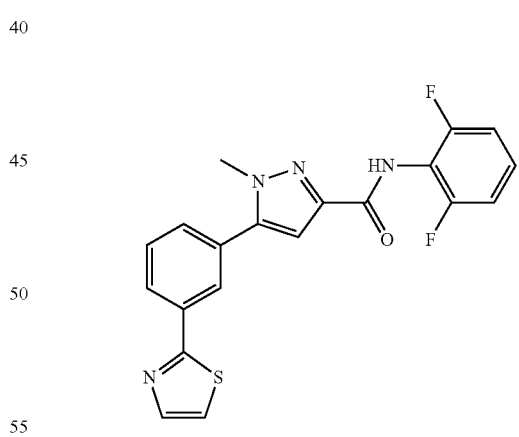

Sodium carbonate (64 mg), Pd(dppf)Cl$_2$.CH$_2$Cl$_2$ (42 mg) and a 2-thiazolylzinc bromide solution (0.5 M in THF, 2.58 mL) were consecutively added to a solution of intermediate 14b (189 mg) in dry THF (1 mL) under an argon atmosphere and the reaction mixture was stirred at 120° C. for 2 h. After addition of saturated ammonium chloride solution (10 mL) the mixture was extracted with EtOAc, dried and the volatiles were removed under reduced pressure. The residue was purified by column chromatography (Interchim® cartridge 15SiHP/25 g, Cy/EtOAc) to yield the desired product (52% yield).

LC-MS (Method 1): m/z [M+H]$^+$=314.2 (MW calc.=313.37); $R_t$=3.6 min.

N-(2,6-Difluoro-phenyl)-1-methyl-5-(3-thiazol-2-yl-phenyl)-1H-pyrazole-3-carboxylic acid amide (Example 14)

2,6-difluoroaniline (55 µL) and trimethylaluminium (2 M in heptane, 0.27 mL) were consecutively added to a solution of intermediate 14c (142 mg) in toluene (3.6 mL) and the mixture was stirred at 110 C for 2 h. After cooling to rt, 1 M HCl (4 mL) was carefully added and the layers were separated. The aqueous layer was extracted with chloroform and the combined organic layers were dried and the volatiles were removed under reduced pressure. The residue was purified through washing with Et$_2$O to yield the title compound of example 14 (60% yield).

LC-MS (Method 2): m/z [M+H]⁺=397.09 (MW calc.=396.41); $R_t$=0.74 min.

SYNTHESIS EXAMPLE 15

5-(5-Cyclopropyl-2-methoxy-phenyl)-N-(3-fluoro-pyridin-4-yl)-1-methyl-1H-pyrazole-3-carboxylic acid amide Intermediate 15a

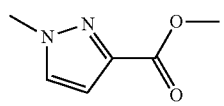

A solution of methyl 1H-pyrazole-3-carboxylate (5 g) in dry acetonitrile was treated with cesium carbonate (32.3 g) and methyl iodide (6.45 g) and the mixture was stirred at rt for 2 h. The suspension was filtered and the volatiles were removed under reduced pressure. The residue was purified by chromatography (SiO₂, Cy/EtOAc) to yield the desired product (66% yield).

LC-MS (Method 1): m/z [M+H]⁺=141.2 (MW calc.=140.14); $R_t$=1.0 min.

Intermediate 15b

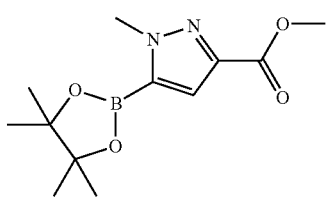

4,4'-Di-tert-butyl-2,2'-dipyridyl (194 mg) was added to a solution of (1,5-Cyclooctadiene)(methoxy)-iridium(I) dimer (241 mg) and pinacolborane (4.13 g) in pentane (21 mL) and the mixture was stirred for 20 min at rt. Then a solution of intermediate 15a (3.02 g) in pentane (14 mL) and THF (7 mL) was added and the solution was stirred at rt for 3 d. The volatiles were removed under reduced pressure and the residue was purified by chromatography (SiO2, DCM/MeOH) to yield the desired product (80% yield).

LC-MS (Method 1): m/z [M (boronic acid)+H]⁺=185.2 (MW (boronic acid) calc.=183.96); $R_t$=1.4 min.

Intermediate 15b*

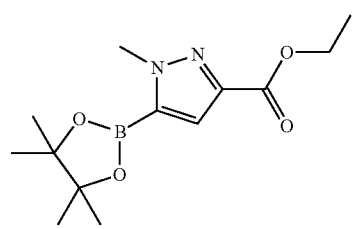 [SMILES: CCOC(=O)c1cc(B2OC(C)(C)C(C)(C)O2)n(C)n1]

Intermediate 15b* was prepared in analogy to the synthesis of intermediate 15b starting from ethyl 1-methyl-1H-pyrazole-3-carboxylate (78% yield).

Intermediate 15c

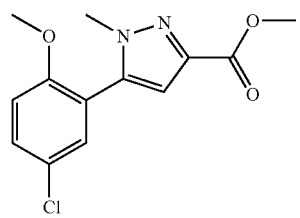 [SMILES: COC(=O)c1cc(-c2cc(Cl)ccc2OC)n(C)n1]

A solution of intermediate 15b (532 mg), 2-bromo-4-chloroanisole (443 mg), potassium carbonate (1.38 g) and bis(tri-tert-butylphosphine)palladium (51 mg) in 1,4 dioxane (20 mL) and water (4 mL) was heated under an argon atmosphere to 80° C. for 1 h. The mixture was chilled, the layers separated and the organic layer was extracted with EtOAc. The combined organic layers were dried and the volatiles were removed under reduced pressure. The residue was purified by chromatography (Interchim® cartridge 30SiHP/25 g, Cy/EtOAc) to yield the desired compound (97% yield).

LC-MS (Method 1): m/z [M+H]⁺=281.3 (MW calc.=280.71); $R_t$=3.5 min.

Intermediate 15d

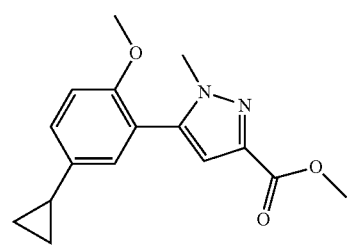 [SMILES: COC(=O)c1cc(-c2cc(C3CC3)ccc2OC)n(C)n1]

A solution of intermediate 15c (140 mg) potassium cyclopropyltrifluoroborate (150 mg), palladium acetate (3 mg), dicyclohexylphosphino-2',4',6'-triisopropylbiphenyl (14 mg) and potassium carbonate (210 mg) in THF (1.8 mL) an water (0.2) was stirred under an argon atmosphere at 110° C. for 16 h. Water (10 mL) was added, the layers were separated and the organic layer was extracted with EtOAc. The combined layers were dried and volatiles were removed under reduced pressure. The residue was purified by chromatography (Interchim® cartridge 30SiHP/25 g, Cy/EtOAc) to yield the desired product (59% yield).

LC-MS (Method 1): m/z [M+H]⁺=287.2 (MW calc.=286.33); $R_t$=3.7 min.

5-(5-Cyclopropyl-2-methoxy-phenyl)-N-(3-fluoro-pyridin-4-yl)-1-methyl-1H-pyrazole-3-carboxylic acid amide (Example 15)

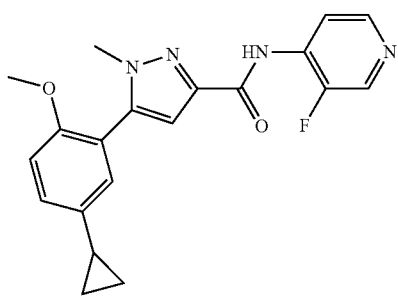 [SMILES: COc1ccc(C2CC2)cc1-c1cc(C(=O)Nc2ccncc2F)nn1C]

To a solution of intermediate 15d (83 mg) and 3-fluoropyridin-4-amine (39 mg) in dry THF (1.5 mL) was added lithium bis(trimethylsilyl)amide (1 M in hexane, 0.44 mL) and the reaction mixture was stirred at 60° C. for 2 h. After cooling to rt water (0.1 mL) was added and the volatiles were removed under reduced pressure. The residue was purified by chromatography (Interchim® cartridge 15SiHP/12 g, DCM/MeOH) to yield the desired product (42% yield).

LC-MS (Method 2): m/z [M+H]$^+$=367.16 (MW calc.=366.39); R$_t$=0.81 min.

SYNTHESIS EXAMPLE 16

5-(5-Cyclopropyl-2-methoxy-phenyl)-N-(2,6-difluoro-phenyl)-1-methyl-1H-pyrazole-3-carboxylic acid amide

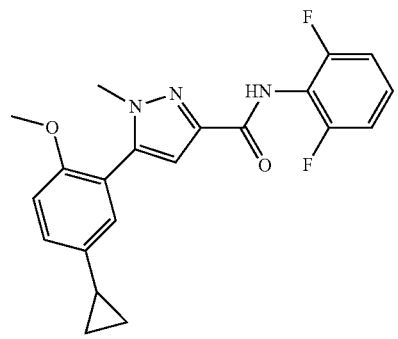 [SMILES: COc1ccc(C2CC2)cc1-c1cc(C(=O)Nc2c(F)cccc2F)nn1C]

The title compound of example 16 was prepared in analogy to the preparation of the title compound of example 15 through the reaction of intermediate 15d (100 mg) with 2,6-difluoroaniline (59 mg) (85% yield).

LC-MS (Method 2): m/z [M+H]$^+$=384.15 (MW calc.=383.39); R$_t$=0.83 min.

SYNTHESIS EXAMPLE 17

5-(2-Cyclopropyl-5-methyl-pyrimidin-4-yl)-N-(2,6-difluoro-phenyl)-1-methyl-1H-pyrazole-3-carboxylic acid amide Intermediate 17a

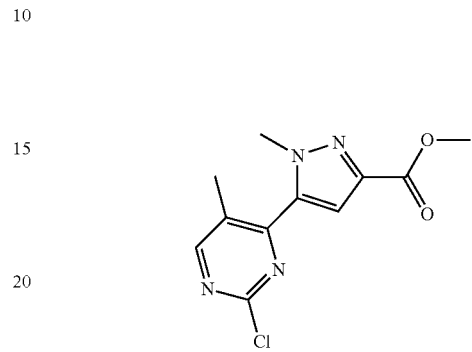

A solution of intermediate 15 b (532 mg), 2,4-dichloro-5-methylpyrimidine (489 mg), potassium carbonate (1.38 g) and bis(tri-tert-butylphosphine)palladium (51 mg) in 1,4-dioxane (20 mL) and water (4 mL) was heated under an argon atmosphere to 80° C. for 1 h. The mixture was chilled, the layers separated and the organic layer was extracted with EtOAc. The combined organic layers were dried and the volatiles were removed under reduced pressure. The residue was purified by chromatography (Interchim® cartridge 30SiHP/25 g, Cy/EtOAc) to yield the desired compound (72% yield).

LC-MS (Method 1): m/z [M+H]$^+$=267.2 (MW calc.=266.68); R$_t$=3.0 min.

Intermediate 17b

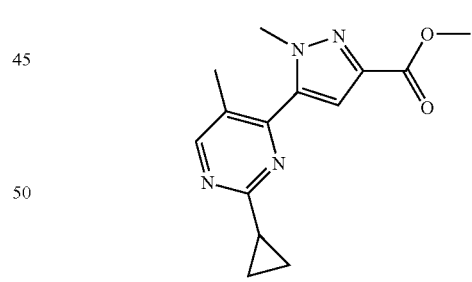

A solution of intermediate 17a (81 mg) potassium cyclopropyltrifluoroborate (302 mg), Pd(dppf)Cl$_2$.CH$_2$Cl$_2$ (44 mg) and potassium hydrogenphosphate (151 mg) in toluene (2.8 mL) an water (0.2) was stirred under an argon atmosphere at 100° C. for 16 h. Water (10 mL) was added, the layers were separated and the organic layer was extracted with DCM. The combined layers were dried and volatiles were removed under reduced pressure. The residue was purified by chromatography (Interchim® cartridge 30SiHP/25 g, DCM/MeOH) to yield the desired product (61% yield).

LC-MS (Method 1): m/z [M+H]$^+$=273.3 (MW calc.=272.30); R$_t$=3.2 min.

5-(2-Cyclopropyl-5-methyl-pyrimidin-4-yl)-N-(2,6-difluoro-phenyl)-1-methyl-1H-pyrazole-3-carboxylic acid amide (Example 17)

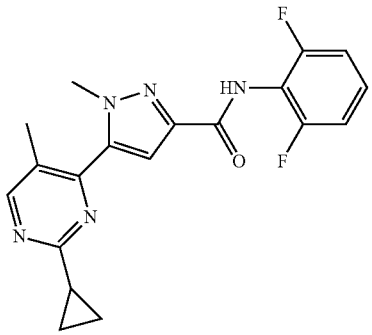 [SMILES: Cc1cnc(C2CC2)nc1-c1cc(C(=O)Nc2c(F)cccc2F)nn1C]

To a solution of intermediate 17b (67 mg) and 2,6-difluoroaniline (41 mg) in dry THF (3 mL) was added lithium bis(trimethylsilyl)amide (1 M in hexane, 0.37 mL) and the reaction mixture was stirred at 60° C. for 2 h. After cooling to rt water (0.1 mL) was added and the volatiles were removed under reduced pressure. The residue was purified by chromatography (Interchim® cartridge 15SiHP/12 g, DCM/MeOH) to yield the desired product (58% yield).

LC-MS (Method 2): m/z [M+H]$^+$=370.15 (MW calc.=369.37); R$_t$=0.71 min.

SYNTHESIS EXAMPLE 18

N-(2,6-Difluoro-phenyl)-1-methyl-5-(2-methyl-5-oxazol-2-yl-phenyl)-1H-pyrazole-3-carboxylic acid amide

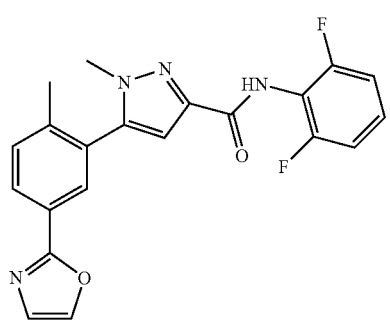 [SMILES: Cc1ccc(-c2ncco2)cc1-c1cc(C(=O)Nc2c(F)cccc2F)nn1C]

The title compound of example 18 was prepared in analogy to the preparation of the title compound of example 17 through the reaction of intermediate 2a (164 mg) with 2,6-difluoroaniline (81 mg) (44% yield).

LC-MS (Method 2): m/z [M+H]$^+$=395.13 (MW calc.=394.37); R$_t$=0.74 min.

SYNTHESIS EXAMPLE 19

N-(2,6-Difluoro-phenyl)-1-methyl-5-[2-methyl-5-(3-methyl-[1,2,4]oxadiazol-5-yl)-phenyl]-1H-pyrazole-3-carboxylic acid amide Intermediate 19a

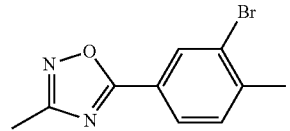

A solution of 3-bromo-4-methylbenzoic acid (323 mg) in thionyl chloride (2.5 mL) was stirred at rt for 17 h. After removal of the volatiles at reduced pressure the residue was dissolved in pyridine (3 mL), N-hydroxyacetimidamide was added and the mixture was stirred at 110° C. for 4 h. At rt 2 M HCl (25 mL) was added and the mixture was extracted with DCM. The combined organic layers were dried and the volatiles were removed under reduced pressure. The residue was purified by chromatography (Interchim® cartridge 15SiHP/25 g, DCM/MeOH) to yield the desired product (30% yield).

Intermediate 19b

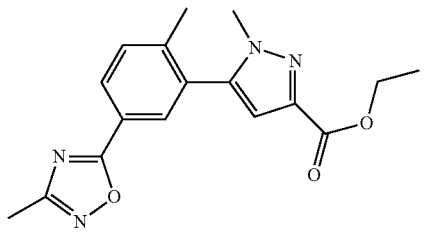 [SMILES: CCOC(=O)c1cc(-c2cc(-c3nc(C)no3)ccc2C)n(C)n1]

A solution of intermediate 15b* (108 mg), intermediate 19a (90 mg), lithium hydroxide (9 mg) and bis(tri-tert-butylphosphine)palladium (10 mg) in DMF (1.5 mL) was heated under an argon atmosphere to 110° C. for 2 h. The volatiles were removed under reduced pressure and the residue was purified by chromatography (Interchim® cartridge 30SiHP/12 g, DCM/MeOH) to yield the desired compound (73% yield).

LC-MS (Method 1): m/z [M+H]$^+$=327.2 (MW calc.=326.35); R$_t$=3.6 min.

N-(2,6-Difluoro-phenyl)-1-methyl-5-[2-methyl-5-(3-methyl-[1,2,4]oxadiazol-5-yl)-phenyl]-1H-pyrazole-3-carboxylic acid amide (Example 19)

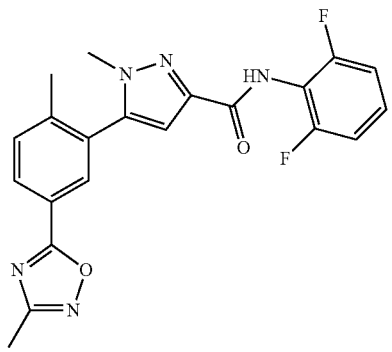 [SMILES: Cc1noc(-c2ccc(C)c(-c3cc(C(=O)Nc4c(F)cccc4F)nn3C)c2)n1]

The title compound of example 19 was prepared in analogy to the preparation of the title compound of example 17 through the reaction of intermediate 19b (83 mg) with 2,6-difluoroaniline (39 mg) (61% yield).

LC-MS (Method 2): m/z [M+H]$^+$=410.14 (MW calc.=409.39); R$_t$=0.76 min.

SYNTHESIS EXAMPLE 20

5-[5-(2-Amino-pyridin-4-yl)-2-methyl-phenyl]-N-(2,6-difluoro-phenyl)-1-methyl-1H-pyrazole-3-carboxylic acid amide Intermediate 20a

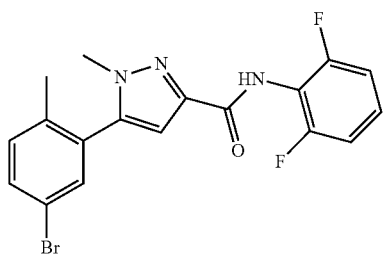 [SMILES: Cc1ccc(Br)cc1-c1cc(C(=O)Nc2c(F)cccc2F)nn1C]

Intermediate 20a was prepared in analogy to the preparation of the title compound of example 14 through the reaction of intermediate 1c (1.29 g) with 2,6-difluoroaniline (1.24 mg) (71% yield).

LC-MS (Method 1): m/z [M+H]$^+$=406.1 (MW calc.=406.22); R$_t$=3.7 min.

Intermediate 20b

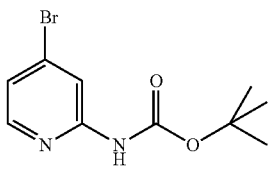

A solution of 4-bromopyridin-2-amine (519 mg) in dry THF (15 mL) was treated with bis(trimethylsilyl)-amide (1 M in hexane, 6 mL) at −5° C. and the solution was stirred at this temperature for 10 minutes. Di-tert-butyl dicarbonate (654 mg) was added and the mixture was stirred at rt for 1 h. Saturated ammonium chloride solution (20 mL) was added and the mixture was extracted with EtOAc. The combined organic layers were washed with water and brine, dried and the volatiles were removed under reduced pressure to yield the desired compound (96% yield).

Intermediate 20c

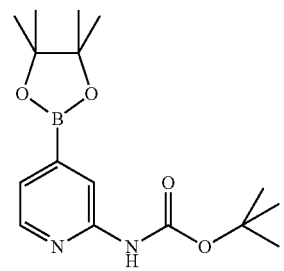 [SMILES: CC(C)(C)OC(=O)Nc1cc(B2OC(C)(C)C(C)(C)O2)ccn1]

A solution of intermediate 20b (352 mg), potassium acetate (380 mg), 4,4,4',4',5,5,5',5'-octamethyl-2,2'-bi(1,3,2-dioxaborolane) (360 mg) and Pd(dppf)Cl$_2$.CH$_2$Cl$_2$ (105 mg) in dry DMF (10 mL) was stirred at 80° C. for 5 h. The volatiles were removed under reduced pressure, the residue dissolved in EtOAc and the organic layer was washed with water, dried and the volatiles were removed under reduced pressure. The crude product was purified through washing with heptane to yield the desired compound (56% yield).

LC-MS (Method 1): m/z [M (boronic acid)+H]$^+$=239.2 (MW (boronic acid) calc.=238.05); R$_t$=2.3 min.

Intermediate 20d

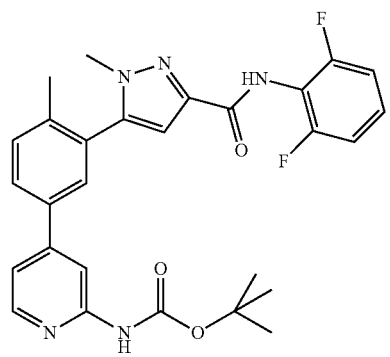 [SMILES: Cc1ccc(-c2ccnc(NC(=O)OC(C)(C)C)c2)cc1-c1cc(C(=O)Nc2c(F)cccc2F)nn1C]

A solution of intermediate 20a (200 mg), intermediate 20c (156 mg), cesium carbonate (312 mg) and tetrakis(triphenylphosphine)palladium (55 mg) in dioxane (12 mL) and water (5 drops) was stirred at 95° C. for 20 h. The volatiles were removed under reduced pressure and the residue was treated with water and extracted with EtOAc. The combined organic layers were dried and the volatiles were removed under reduced pressure. The residue was purified by chromatography (SiO$_2$, 65 g, Cy/EtOAc) to yield the desired compound (61% yield).

LC-MS (Method 1): m/z [M+H]$^+$=520.3 (MW calc.=519.54); R$_t$=3.9 min.

5-[5-(2-Amino-pyridin-4-yl)-2-methyl-phenyl]-N-(2,6-difluoro-phenyl)-1-methyl-1H-pyrazole-3-carboxylic acid amide (Example 20)

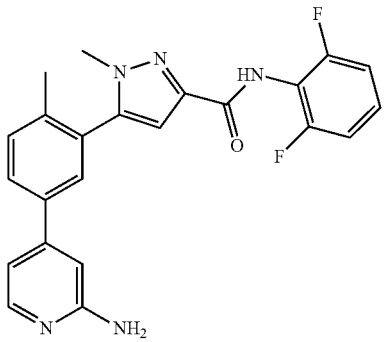 [SMILES: Cc1ccc(-c2ccnc(N)c2)cc1-c1cc(C(=O)Nc2c(F)cccc2F)nn1C]

A solution of intermediate 20d (153 mg) in DCM (5 mL) was treated with trifluoroacetic acid (3 mL) and the mixture was stirred at rt for 1 h. The volatiles were removed under reduced pressure and the residue was treated with 1 M NaOH (20 mL) and was extracted with DCM. The combined organic layers were dried and the volatiles were removed under reduced pressure. The residue was purified trough washing with Et$_2$O to yield the title compound of example 20 (53% yield).

LC-MS (Method 2): m/z [M+H]$^+$=420.16 (MW calc.=419.43); R$_t$=0.52 min.

SYNTHESIS EXAMPLE 21

N-(3-Fluoro-pyridin-4-yl)-1-methyl-5-(2-methyl-5-tetrahydro-pyran-4-yl-phenyl)-1H-pyrazole-3-carboxylic acid amide Intermediate 21a

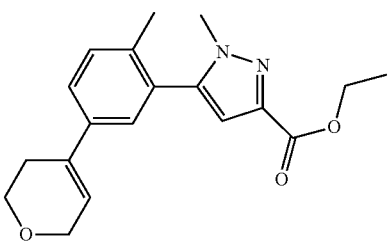 [SMILES: CCOC(=O)c1cc(-c2cc(C3=CCOCC3)ccc2C)n(C)n1]

A solution of intermediate 1c (323 mg), 2-(3,6-dihydro-2H-pyran-4-yl)-4,4,5,5-tetramethyl-1,3,2-dioxa-borolane (280 mg), sodium carbonate (212 mg) and tetrakis(triphenylphosphine)palladium (58 mg) in 1,2-dimethoxyethane (5 mL) and water (0.2 mL) was stirred at 110° C. for 3 h. The mixture was chilled, filtered and the volatiles were removed under reduced pressure. The residue was purified by chromatography (Interchim® cartridge 30SiHP/25 g, Cy/EtOAc) to yield the desired compound (27% yield).

LC-MS (Method 1): m/z [M+H]$^+$=327.3 (MW calc.=326.39); R$_t$=3.7 min.

Intermediate 21b

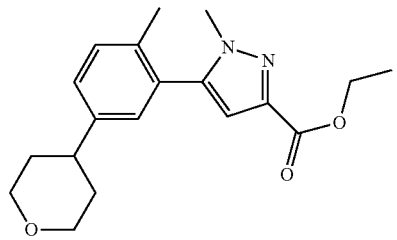 [SMILES: CCOC(=O)c1cc(-c2cc(C3CCOCC3)ccc2C)n(C)n1]

A solution of intermediate 21a (88 mg) and palladium on charcoal (5%, 29 mg) in EtOAc was stirred under a hydrogen atmosphere (3 bar) for 1 h. The mixture was filtered and the volatiles were removed under reduced pressure to yield the desired compound (83% yield).

LC-MS (Method 1): m/z [M+H]$^+$=329.3 (MW calc.=328.41); R$_t$=3.7 min.

N-(3-Fluoro-pyridin-4-yl)-1-methyl-5-(2-methyl-5-tetrahydro-pyran-4-yl-phenyl)-1H-pyrazole-3-carboxylic acid amide (Example 21)

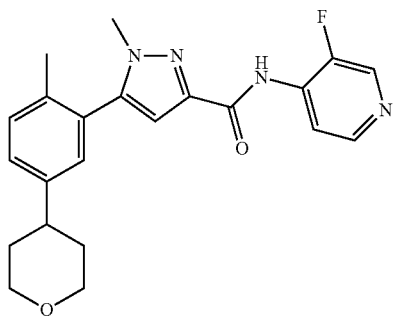 [SMILES: Cc1ccc(C2CCOCC2)cc1-c1cc(C(=O)Nc2ccncc2F)nn1C]

The title compound of example 21 was prepared in analogy to the preparation of the title compound of example 17 through the reaction of intermediate 21b (83 mg) with 3-fluoropyridin-4-amine (38 mg) (67% yield).

LC-MS (Method 2): m/z [M+H]$^+$=395.19 (MW calc.=394.44); R$_t$=0.78 min.

SYNTHESIS EXAMPLE 22

N-(2,6-Difluoro-phenyl)-1-methyl-5-(2-methyl-5-tetrahydro-pyran-4-yl-phenyl)-1H-pyrazole-3-carboxylic acid amide

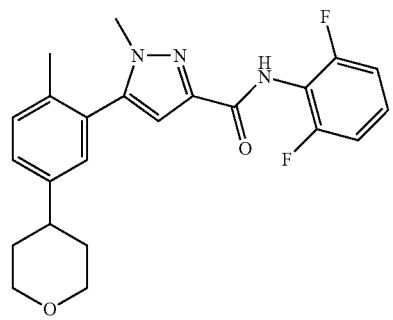 [SMILES: Cc1ccc(C2CCOCC2)cc1-c1cc(C(=O)Nc2c(F)cccc2F)nn1C]

The title compound of example 22 was prepared in analogy to the preparation of the title compound of example 17 through the reaction of intermediate 21b (100 mg) with 2,6-difluoroaniline (51 mg) (56% yield).

LC-MS (Method 2): m/z [M+H]$^+$=412.18 (MW calc.=411.44); R$_t$=0.80 min.

SYNTHESIS EXAMPLE 23

N-(2,6-Difluoro-phenyl)-1-methyl-5-[2-methyl-5-(1-methyl-1H-[1,2,4]triazol-3-yl)-phenyl]-1H-pyrazole-3-carboxylic acid amide Intermediate 23a

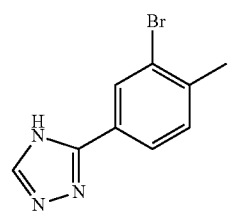

A solution of 3-bromo-4-methylbenzonitrile (1.0 g) in EtOH (20 mL) was saturated at 0° C. with gaseous HCl and the solution was stirred at rt for 2 h. The volatiles were removed under reduced pressure and the residue was dissolve in EtOH (9 mL). Formohydrazide (0.45 g) and triethylamine (2.8 mL) were added and the solution was stirred at 90° C. for 2 h. Water (50 mL) was added and the mixture was extracted with EtOAc. The combined organic layers were dried and the volatiles were removed under reduced pressure. The residue was purified by column chromatography (Interchim® cartridge 30SiHP, 40 g, Cy/EtOAc) to yield the desired product (40% yield).

LC-MS (Method 1): m/z [M+H]$^+$=238.1 (MW calc.=238.08); R$_t$=3.3 min.

Intermediate 23b

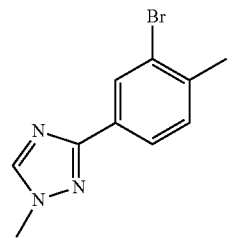

A solution of intermediate 23a (407 mg) in acetone (20 mL) was treated with potassium carbonate (701 mg) and methyl iodide (222 µL) and the resulting mixture was stirred at rt for 4 h. The suspension was filtered and the volatiles were removed under reduced pressure. The residue was purified by chromatography (SiO$_2$, Cy/EtOAc) to yield the desired compound (73% yield).

LC-MS (Method 1): m/z [M+H]$^+$=252.1 (MW calc.=252.11); R$_t$=3.6 min.

Intermediate 23c

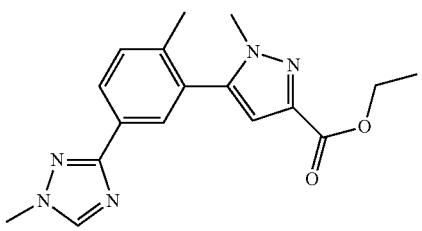 [SMILES: CCOC(=O)c1cc(-c2cc(-c3ncn(C)n3)ccc2C)n(C)n1]

Intermediate 23c was prepared in analogy to the synthesis of intermediate 19b through the reaction of intermediate 15b* (140 mg) with intermediate 23b (156 mg) (57% yield).

LC-MS (Method 1): m/z [M+H]$^+$=326.2 (MW calc.=325.37); R$_t$=3.4 min.

N-(2,6-Difluoro-phenyl)-1-methyl-5-[2-methyl-5-(1-methyl-1H-[1,2,4]triazol-3-yl)-phenyl]-1H-pyrazole-3-carboxylic acid amide: (Example 23)

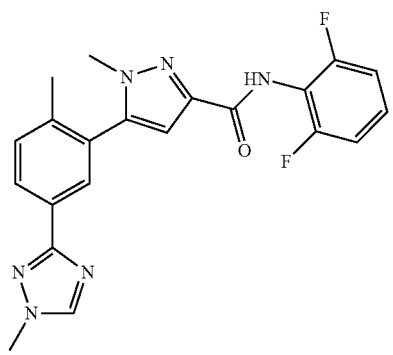 [SMILES: Cc1ccc(-c2ncn(C)n2)cc1-c1cc(C(=O)Nc2c(F)cccc2F)nn1C]

The title compound of example 23 was prepared in analogy to the preparation of the title compound of example 17 through the reaction of intermediate 23c (115 mg) with 2,6-difluoroaniline (54 mg) (43% yield).

LC-MS (Method 2): m/z [M+H]$^+$=409.16 (MW calc.=408.40); R$_t$=0.66 min.

SYNTHESIS EXAMPLE 24

N-(2,6-Difluoro-phenyl)-1-methyl-5-(2-methyl-4-thiazol-2-yl-phenyl)-1H-pyrazole-3-carboxylic acid amide Intermediate 24a

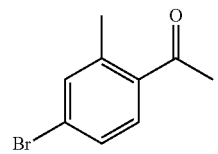

Methyl magnesium bromide (3 M in tetrahydrofuran) was added at rt drop wise to a solution of 4-bromo-2-methylbenzonitrile (4 g) in dry THF (15 mL) and was then heated to reflux for 2 h and then stirred at rt for 3 d. The mixture was chilled in an ice bath, saturated aqueous ammonium chloride solution (100 mL) was added and the mixture was extracted with EtOAc. The combined organic layers were concentrated under reduced pressure and the remaining residue was treated with 4 N HCl at 0° C. and was stirred at rt for 18 h. The mixture was extracted with EtOAc and the organic layer was washed with water, dried and the solvent was removed under reduced pressure to yield the desired product (88% yield).

Intermediate 24b

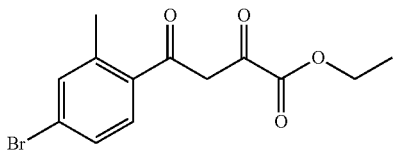

A solution of sodium (463 mg) in dry EtOH (25 mL) was treated with a solution of intermediate 24a (3.84 g) in dry Et$_2$O (10 mL) and was stirred at rt for 15 min. A solution of diethyl oxalate (2.68 mL) in dry Et$_2$O (10 mL) was added and the mixture was stirred at rt for 18 h until when 1 M HCl (50 mL) was added. The layers were separated and the aqueous phase was extracted with EtOAc. The combined organic layers were dried and the solvents were removed under reduced pressure to yield the desired product (78% yield).

Intermediate 24c

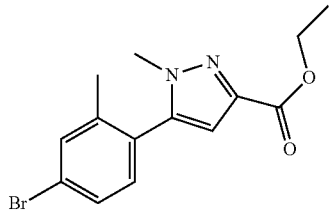 [SMILES: CCOC(=O)c1cc(-c2ccc(Br)cc2C)n(C)n1]

Methylhydrazin (1.09 g) was added to a solution of intermediate 24b (4.39 g) in EtOH (70 mL) at 0° C. and was then stirred at 80° C. for 30 min. The volatiles were removed under reduced pressure and the residue was purified by chromatography (Interchim® cartridge 50SiHP/80 g, Cy/EtOAc) to yield the desired product (48% yield).

LC-MS (Method 1): m/z [M+H]$^+$=323.1 (MW calc.=323.19); R$_t$=3.9 min.

Intermediate 24d

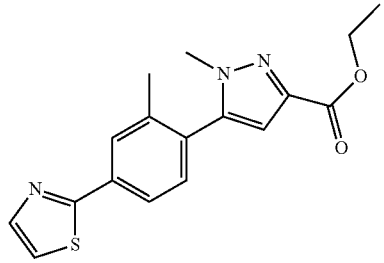 [SMILES: CCOC(=O)c1cc(-c2ccc(-c3nccs3)cc2C)n(C)n1]

2-Thiazolyl)zinc bromide (6 mL, 0.5 M in THF) was added to a solution of intermediate 24c (500 mg), sodium carbonate (165 mg) bis(triphenylphosphine)palladium (II) chloride (107 mg) in dry THF under an argon atmosphere and the mixture was heated to 120° C. for 5 h. Saturated ammonium chloride solution (8 mL) was added and the mixture was extracted with EtOAc. The combined organic layers were dried, the volatiles were removed under removed pressure and the remaining residue was purified by chromatography (Interchim® cartridge 30SiHP/25 g, DCM/MeOH) to the desired product (99% yield).

LC-MS (Method 1): m/z [M+H]$^+$=328.2 (MW calc.=327.40); R$_t$=3.7 min.

N-(2,6-Difluoro-phenyl)-1-methyl-5-(2-methyl-4-thiazol-2-yl-phenyl)-1H-pyrazole-3-carboxylic acid amide (Example 24)

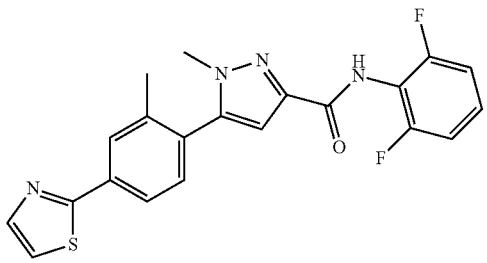 [SMILES: Cc1cc(-c2nccs2)ccc1-c1cc(C(=O)Nc2c(F)cccc2F)nn1C]

The title compound of example 24 was prepared in analogy to the preparation of the title compound of example 17 through the reaction of intermediate 24d (95 mg) with 2,6-difluoroaniline (45 mg) (44% yield).

LC-MS (Method 2): m/z [M+H]$^+$=411.12 (MW calc.=410.44); R$_t$=0.78 min.

SYNTHESIS EXAMPLE 25

N-(2,6-Difluoro-phenyl)-1,4-dimethyl-5-(2-methyl-5-thiazol-2-yl-phenyl)-1H-pyrazole-3-carboxylic acid amide Intermediate 25a

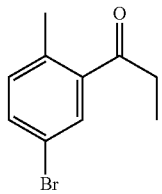

Ethyl magnesium bromide (3 M in Et$_2$O, 8 mL) was added to solution of 5-bromo-2-methylbenzonitrile (2.15 g) in Et$_2$O (8 mL) the mixture was stirred at rt for 16 h. The reaction was carefully quenched with 4 M HCl (12 mL) and was stirred at rt for 4 d. The layers were separated and the aqueous layer was extracted with Et$_2$O. The combined organic layers were washed with water, dried and the volatiles were removed under reduced pressure to yield the desired compound (8% yield).

Intermediate 25b

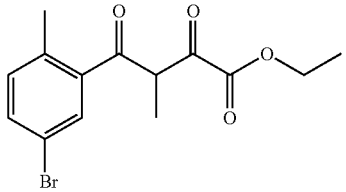 [SMILES: CCOC(=O)C(=O)C(C)C(=O)c1cc(Br)ccc1C]

Lithium bis(trimethylsilyl)amide (1 M in hexane, 9.6 mL) was added at 0° C. to a solution of intermediate 25a (1.98 g) in THF (23 mL) and the mixture was stirred at this temperature for 1 h. A solution of diethyl oxalate (1.43 g) in THF (10 mL) was added and the mixture was stirred at rt for 1 h. Then, 2 M HCl (15 mL) was added and the mixture was extracted with Et$_2$O. The combined organic layers were washed with water, dried and the volatiles were removed under reduced pressure to yield the desired product (94% yield).

LC-MS (Method 1): m/z [M+H]$^+$=327.1 (MW calc.=327.17); R$_t$=3.7 min.

Intermediate 25c

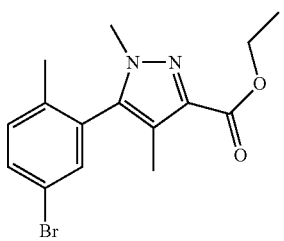 [SMILES: CCOC(=O)c1nn(C)c(-c2cc(Br)ccc2C)c1C]

To a solution of intermediate 25b (1.5 g) in EtOH (16 mL) methyl hydrazine (264 μL) was added at 0° C. and the reaction mixture stirred for 1 h at rt. The solvent was removed under reduced pressure and the residue was purified by chromatography (Interchim® cartridge 50SiHP/120 g, DCM/MeOH) to yield the desired product (44% yield).

LC-MS (Method 1): m/z [M+H]$^+$=337.1 (MW calc.=337.21); R$_t$=3.9 min.

Intermediate 25d

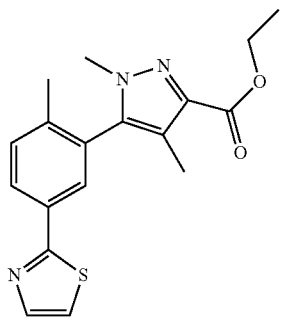 [SMILES: CCOC(=O)c1nn(C)c(-c2cc(-c3nccs3)ccc2C)c1C]

A solution of intermediate 25c (500 mg), 2-(tri-n-butyl-stannyl)thiazole (554 mg) and bis(triphenyl-phosphine)palladium (II) chloride (104 mg) in dry acetonitrile (18 mL) was stirred at 110° C. for 2 h. The solvent was removed under reduced pressure and the remaining material purified by column chromatography (Interchim® cartridge 30SiHP, 40 g, Cy/EtOAc) to yield the desired product (39% yield).

LC-MS (Method 1): m/z [M+H]$^+$=342.2 (MW calc.=341.43); R$_t$=3.8 min.

N-(2,6-Difluoro-phenyl)-1,4-dimethyl-5-(2-methyl-5-thiazol-2-yl-phenyl)-1H-pyrazole-3-carboxylic acid amide (Example 25)

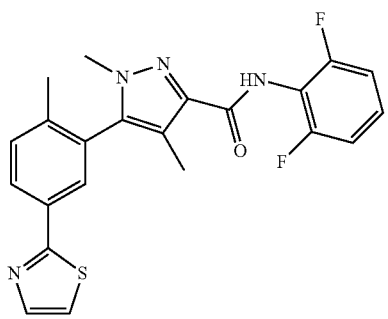 [SMILES: Cc1ccc(-c2nccs2)cc1-c1c(C)c(C(=O)Nc2c(F)cccc2F)nn1C]

The title compound of example 25 was prepared in analogy to the preparation of the title compound of example 17 through the reaction of intermediate 25d (90 mg) with 2,6-difluoroaniline (44 mg) (66%).

LC-MS (Method 2): m/z [M+H]$^+$=425.13 (MW calc.=424.47); R$_t$=0.85 min.

SYNTHESIS EXAMPLE 26

N-(3-Fluoro-pyridin-4-yl)-1,4-dimethyl-5-(2-methyl-5-thiazol-2-yl-phenyl)-1H-pyrazole-3-carboxylic acid amide

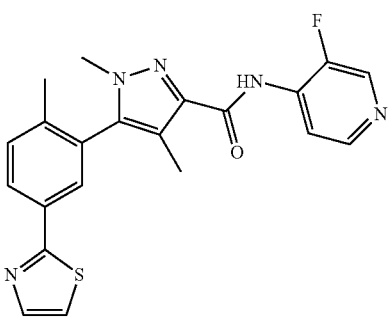 [SMILES: Cc1ccc(-c2nccs2)cc1-c1c(C)c(C(=O)Nc2ccncc2F)nn1C]

The title compound of example 26 was prepared in analogy to the preparation of the title compound of example 17 through the reaction of intermediate 25d (90 mg) with 3-fluoropyridin-4-amine (39 mg) (67%).

LC-MS (Method 2): m/z [M+H]$^+$=408.13 (MW calc.=407.46); R$_t$=0.84 min.

SYNTHESIS EXAMPLE 27

N-(2,6-Difluoro-phenyl)-1,4-dimethyl-5-(3-thiazol-2-yl-phenyl)-1H-pyrazole-3-carboxylic acid amide Intermediate 27a

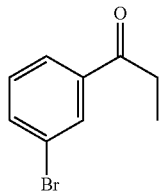

Intermediate 27a was prepared in analogy to the preparation of intermediate 25a starting from 3-brombenzonitrile (1.5 g) (88% yield).

Intermediate 27b

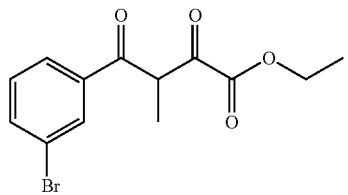 [SMILES: CCOC(=O)C(=O)C(C)C(=O)c1cccc(Br)c1]

Intermediate 27b was prepared in analogy to the preparation of intermediate 25b starting from intermediate 27a (1.45 g) (99%).

LC-MS (Method 1): m/z [M+H]$^+$=313.1 (MW calc.=313.14); R$_t$=3.6 min.

Intermediate 27c

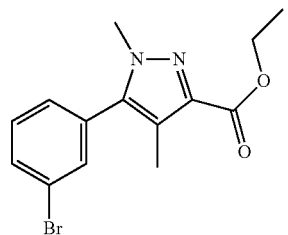 [SMILES: CCOC(=O)c1nn(C)c(-c2cccc(Br)c2)c1C]

Intermediate 27c was prepared in analogy to the preparation of intermediate 25c starting from intermediate 27b (2.11 g) (22% yield).

LC-MS (Method 1): m/z [M+H]$^+$=323.1 (MW calc.=323.19); R$_t$=3.8 min.

Intermediate 27d

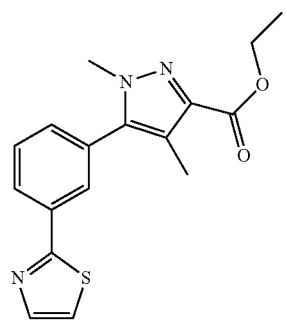 [SMILES: CCOC(=O)c1nn(C)c(-c2cccc(-c3nccs3)c2)c1C]

Intermediate 27d was prepared in analogy to the preparation of intermediate 25d starting from intermediate 27c (373 mg) (53%).

LC-MS (Method 1): m/z [M+H]$^+$=328.2 (MW calc.=327.40); R$_t$=3.7 min.

N-(2,6-Difluoro-phenyl)-1,4-dimethyl-5-(3-thiazol-2-yl-phenyl)-1H-pyrazole-3-carboxylic acid amide
(Example 27)

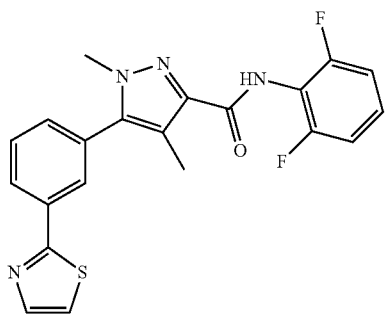

The title compound of example 27 was prepared in analogy to the preparation of the title compound of example 17 through the reaction of intermediate 27d (95 mg) with 2,6-difluoroaniline (49 mg) (66% yield).

LC-MS (Method 2): m/z [M+H]$^+$=411.11 (MW calc.=410.44); R$_t$=0.82 min.

SYNTHESIS EXAMPLE 28

N-(2,6-Difluoro-phenyl)-1-methyl-5-[2-methyl-5-(5-methyl-4H-[1,2,4]triazol-3-yl)-phenyl]-1H-pyrazole-3-carboxylic acid amide Intermediate 28a

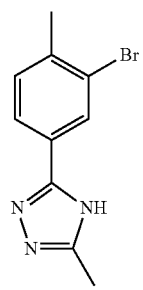

A solution of 3-bromo-4-methylbenzonitrile (1 g), acetamidine hydrochloride (714 mg), cesium carbonate (5 g) and copper (I) bromide (36 mg) in dry dimethyl sulfoxide (25 mL) was stirred at 120° C. for 3 h. The mixture was chilled, diluted with EtOAc (200 mL) and washed with water. The organic layer was dried and the volatiles were removed under reduced pressure. The residue was purified by chromatography (SiO$_2$, 150 g, DCM/MeOH) to yield the desired product (36% yield).

LC-MS (Method 1): m/z [M+H]$^+$=252.1 (MW calc.=252.11); R$_t$=3.5 min.

Intermediate 28b

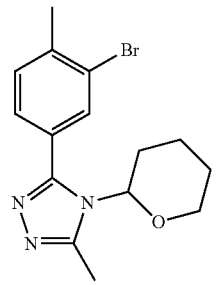 [SMILES: Cc1ccc(-c2nnc(C)n2C2CCCCO2)cc1Br]

3,4-Dihydro-2H-pyran (543 µL) and methane sulfonic acid (5.7 mL) were added to a solution of intermediate 28a (300 mg) and the mixture was stirred at 70° C. for 2 h. The solution was chilled, diluted with EtOAc (150 mL) and was washed with sodium bicarbonate solution. The organic layer was dried and the volatiles were removed under reduced pressure to yield the desired compound (99% yield).

Intermediate 28c

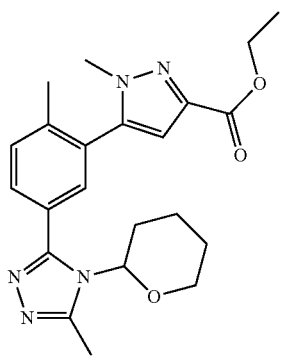 [SMILES: CCOC(=O)c1cc(-c2cc(-c3nnc(C)n3C3CCCCO3)ccc2C)n(C)n1]

Intermediate 28c was prepared in analogy to the synthesis of intermediate 19b through the reaction of intermediate 15b* (156 mg) with intermediate 28b (170 mg) (51% yield).

LC-MS (Method 1): m/z [M+H]$^+$=410.3 (MW calc.=409.48); R$_t$=3.8 min.

Intermediate 28d

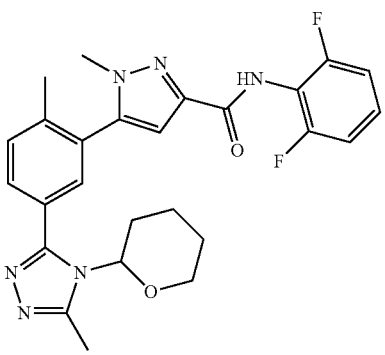 [SMILES: Cc1ccc(-c2nnc(C)n2C2CCCCO2)cc1-c1cc(C(=O)Nc2c(F)cccc2F)nn1C]

Intermediate 28d was prepared in analogy to the preparation of the title compound of example 17 through the reaction of intermediate 28c (133 mg) with 2,6-difluoroaniline (49 mg) (95% yield).

N-(2,6-Difluoro-phenyl)-1-methyl-5-[2-methyl-5-(5-methyl-4H-[1,2,4]triazol-3-yl)-phenyl]-1H-pyrazole-3-carboxylic acid amide (Example 28)

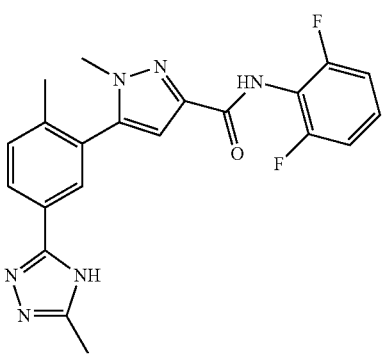 [SMILES: Cc1nnc(-c2ccc(C)c(-c3cc(C(=O)Nc4c(F)cccc4F)nn3C)c2)[nH]1]

A solution of intermediate 28d (150 mg) in EtOH (5 mL) was treated with 4 M HCl (0.25 mL) and the solution was stirred at 60° C. for 3 h. The mixture was chilled and extracted with EtOAc. The combined organic layers were dried and the volatiles were removed under reduced pressure. The residue was washed with methyl acetate and Et$_2$O to yield the desired compound (51% yield).

LC-MS (Method 2): m/z [M+H]$^+$=409.16 (MW calc.=408.40); R$_t$=0.60 min.

SYNTHESIS EXAMPLE 29

N-(3-Fluoro-pyridin-4-yl)-1,4-dimethyl-5-(3-thiazol-2-yl-phenyl)-1H-pyrazole-3-carboxylic acid amide

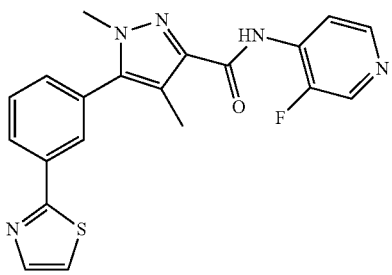 [SMILES: Cc1c(C(=O)Nc2ccncc2F)nn(C)c1-c1cccc(-c2nccs2)c1]

The title compound of example 29 was prepared in analogy to the preparation of the title compound of example 17 through the reaction of intermediate 27d (100 mg) with 4-amino-3-fluoropyridin (44 mg) (64% yield).

LC-MS (Method 2): m/z [M+H]$^+$=394.11 (MW calc.=393.44); $R_t$=0.80 min.

SYNTHESIS EXAMPLE 30

N-(2,6-Difluoro-phenyl)-1-methyl-5-[5-oxazol-2-yl-2-(trifluoromethyloxy)-phenyl]-1H-pyrazole-3-carboxylic acid amide Intermediate 30a

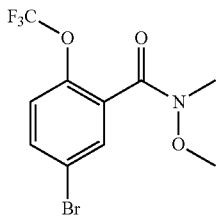 [SMILES: CON(C)C(=O)c1cc(Br)ccc1OC(F)(F)F]

A suspension of 5-bromo-2-(trifluoromethoxy)benzoic acid (1.14 g) in thionyl chloride (5 mL) was stirred at 75° C. for 1 h. The volatiles were removed under reduced pressure and the residue dissolved in DCM (10 mL). A solution of N,O-dimethylhydroxylamine hydrochloride (468 mg) and triethylamine (1.11 mL) in DCM (10 mL) was added and the mixture was stirred at rt for 3 h. The mixture was washed with saturated ammonium chloride solution and water, dried and the volatiles were removed under reduced pressure to yield the desired compound (87% yield).

Intermediate 30b

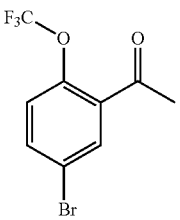

A solution of intermediate 30a (1.14 g) in dry THF (10 mL) was treated with methyl magnesium chloride (3 M in THF, 2.32 mL) at 0° C. and the resulting mixture was stirred at rt for 1 h. 2 N HCl was added and the mixture was extracted with EtOAc. The combined organic layers were dried and the volatiles were removed under reduced pressure to yield the desired compound (95% yield).

Intermediate 30c

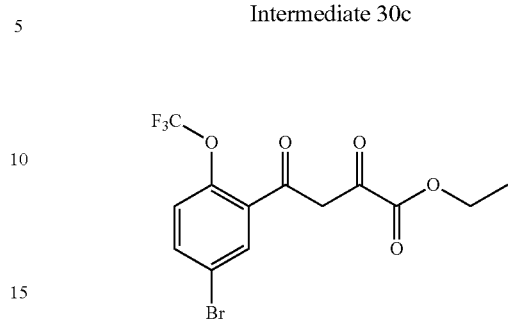

Intermediate 30c was prepared in analogy to the preparation of intermediate 1b starting from intermediate 30b (930 mg) (94% yield).

Intermediate 30d

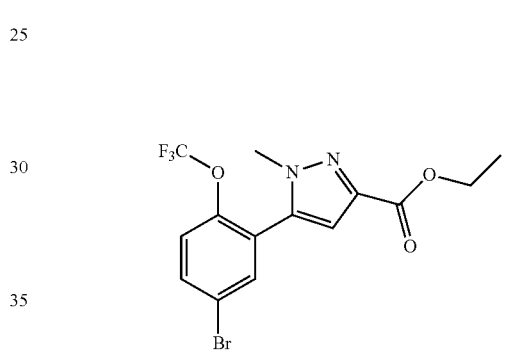

Intermediate 30d was prepared in analogy to the preparation of intermediate 14b starting from intermediate 30c (1.19 mg) (53% yield).

LC-MS (Method 1): m/z [M+H]$^+$=393.1 (MW calc.=393.16); $R_t$=3.9 min.

Intermediate 30e

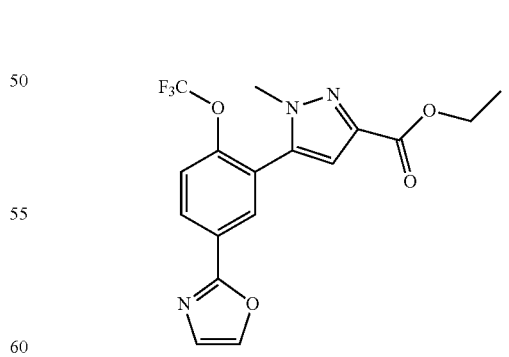

Intermediate 30e was prepared in analogy to the preparation of intermediate 25d starting from intermediate 30d (329 mg) (86% yield).

LC-MS (Method 1): m/z [M+H]$^+$=382.2 (MW calc.=381.31); $R_t$=3.8 min.

N-(2,6-Difluoro-phenyl)-1-methyl-5-[5-oxazol-2-yl-2-(trifluoromethyloxy)-phenyl]-1H-pyrazole-3-carboxylic acid amide (Example 30)

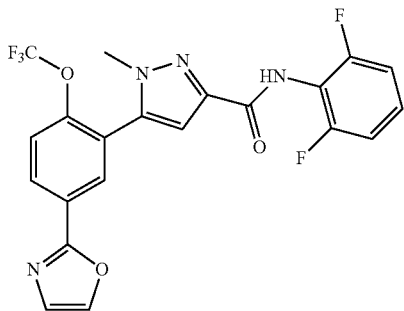 [SMILES: Cn1nc(C(=O)Nc2c(F)cccc2F)cc1-c1cc(-c2ncco2)ccc1OC(F)(F)F]

The title compound of example 30 was prepared in analogy to the preparation of the title compound of example 17 through the reaction of intermediate 30e (87 mg) with 2,6-difluoroaniline (41 mg) (72% yield).

LC-MS (Method 2): m/z [M+H]$^+$=465.10 (MW calc.=464.34); R$_t$=0.80 min.

SYNTHESIS EXAMPLE 31

N-(3-Fluoro-pyridin-4-yl)-1-methyl-5-[5-oxazol-2-yl-2-(trifluoromethyloxy)-phenyl]-1H-pyrazole-3-carboxylic acid amide

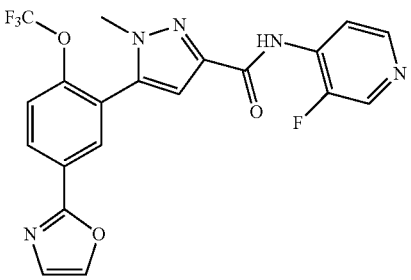 [SMILES: Cn1nc(C(=O)Nc2ccncc2F)cc1-c1cc(-c2ncco2)ccc1OC(F)(F)F]

The title compound of example 31 was prepared in analogy to the preparation of the title compound of example 17 through the reaction of intermediate 30e (80 mg) with 3-fluoropyridin-4-amine (33 mg) (77% yield).

LC-MS (Method 2): m/z [M+H]$^+$=448.10 (MW calc.=447.34); R$_t$=0.78 min.

SYNTHESIS EXAMPLE 32

N-(2,6-Difluoro-phenyl)-1-methyl-5-[2-methyl-5-(4H-[1,2,4]triazol-3-yl)-phenyl]-1H-pyrazole-3-carboxylic acid amide Intermediate 32a

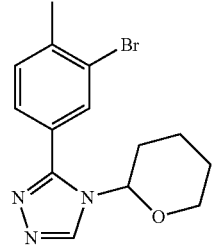 [SMILES: Cc1ccc(-c2nncn2C2CCCCO2)cc1Br]

Intermediate 32a was prepared in analogy to the preparation of intermediate 29b starting from intermediate 23a (280 mg) (74% yield).

Intermediate 32b

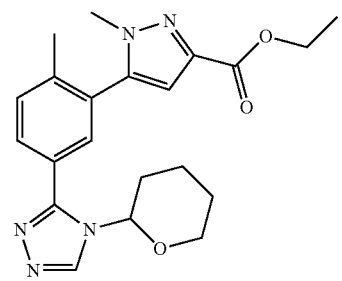 [SMILES: CCOC(=O)c1cc(-c2cc(-c3nncn3C3CCCCO3)ccc2C)n(C)n1]

Intermediate 32b was prepared in analogy to the synthesis of intermediate 19b through the reaction of intermediate 15b* (267 mg) with intermediate 32a (280 mg) (76% yield).

LC-MS (Method 1): m/z [M+H]$^+$=396.3 (MW calc.=395.45); R$_t$=3.8 min.

N-(2,6-Difluoro-phenyl)-1-methyl-5-[2-methyl-5-(4H-[1,2,4]triazol-3-yl)-phenyl]-1H-pyrazole-3-carboxylic acid amide (Example 32)

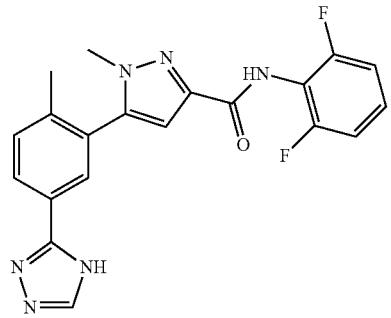 [SMILES: Cc1ccc(-c2nnc[nH]2)cc1-c1cc(C(=O)Nc2c(F)cccc2F)nn1C]

To a solution of intermediate 32b (67 mg) and 2,6-difluoroaniline (41 mg) in dry THF (3 mL) was added lithium bis(trimethylsilyl)amide (1 M in hexane, 0.37 mL) and the reaction mixture was stirred at 60° C. for 1 h. The volatiles were removed under reduced pressure, the residue dissolved in EtOH (6 mL), treated with 4 M HCl (0.3 mL) and the resulting mixture was stirred at 60° C. for 2 h. The mixture was chilled and was extracted with EtOAc. The combined organic layers were dried and the volatiles were removed under reduced pressure. The residue was purified through washing with acetone and Et$_2$O to yield the title compound of example 323 (56% yield).

LC-MS (Method 2): m/z [M+H]$^+$=395.14 (MW calc.=394.38); R$_t$=0.60 min.

SYNTHESIS EXAMPLE 33

N-(3,5-Difluoro-pyridin-4-yl)-1-methyl-5-[5-oxazol-2-yl-2-(trifluoro-methyloxy)-phenyl]-1H-pyrazole-3-carboxylic acid amide

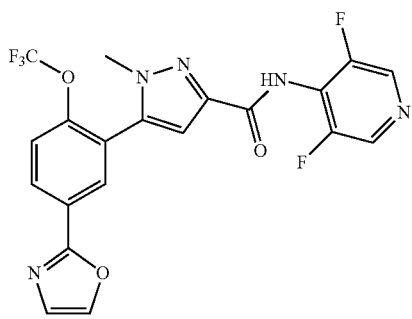 [SMILES: Cn1nc(C(=O)Nc2c(F)cncc2F)cc1-c1cc(-c2ncco2)ccc1OC(F)(F)F]

The title compound of example 33 was prepared in analogy to the preparation of the title compound of example 17 through the reaction of intermediate 30e (85 mg) with 3,5-difluoropyridin-4-amine (41 mg) (77% yield).

LC-MS (Method 2): m/z [M+H]$^+$=466.09 (MW calc.=465.33); R$_t$=0.75 min.

SYNTHESIS EXAMPLE 34

5-(5-Cyclopropyl-2-methoxy-phenyl)-N-(2,6-difluoro-phenyl)-1,4-dimethyl-1H-pyrazole-3-carboxylic acid amide Intermediate 34a

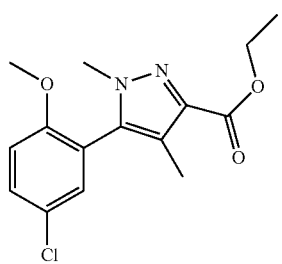 [SMILES: CCOC(=O)c1nn(C)c(-c2cc(Cl)ccc2OC)c1C]

A suspension of ethyl 1,4-dimethyl-1H-pyrazole-3-carboxylate (420 mg), 2-bromo-4-chloro-1-methoxy-benzene (888 mg), di(1-adamantyl)-n-butylphosphine (134 mg), pivalic acid (64 mg) and potassium carbonate (56 mg) in dry N,N-dimethylacetamide (7 mL) was degassed and palladium (II) acetate (56 mg) was added. The mixture was stirred at 150° C. for 5 h. The volatiles were removed under reduced pressure and the residue was treated with water and extracted with EtOAc. The combined organic layers were dried and the volatiles were removed under reduced pressure. The residue was purified by column chromatography (Interchim® cartridge 30SiHP, 40 g, Cy/EtOAc) to yield the desired product (46% yield).

LC-MS (Method 1): m/z [M+H]$^+$=309.2 (MW calc.=308.76); R$_t$=3.8 min.

Intermediate 34b

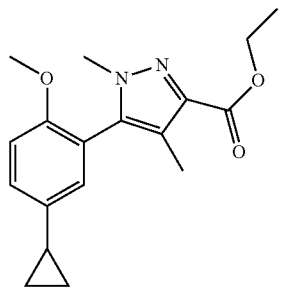 [SMILES: CCOC(=O)c1nn(C)c(-c2cc(C3CC3)ccc2OC)c1C]

Potassium cyclopropyltrifluoroborate (248 mg), palladium (II) acetate (26 mg), di(1-adamantyl)-n-butyl-phosphine (83 mg) and cesium carbonate (1.12 g) were consecutively added to a degassed solution of intermediate 34a (580 mg) in toluene (9 mL) and water (1 mL) and the mixture was stirred at 100° C. for 24 h. The mixture was chilled, the layers were separated and the organic layer was extracted with EtOAc. The combined organic layers were dried and the volatiles were removed under reduced pressure. The residue was purified by column chromatography (Interchim® cartridge 30SiHP, 40 g, Cy/EtOAc) to yield the desired product (77% yield).

LC-MS (Method 1): m/z [M+H]$^+$=315.3 (MW calc.=314.38); R$_t$=3.9 min.

5-(5-Cyclopropyl-2-methoxy-phenyl)-N-(2,6-difluoro-phenyl)-1,4-dimethyl-1H-pyrazole-3-carboxylic acid amide (Example 34)

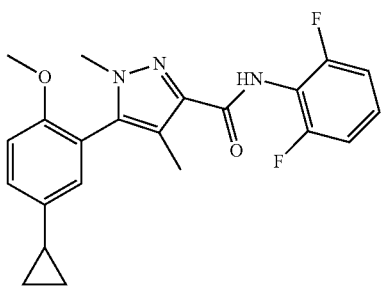 [SMILES: COc1ccc(C2CC2)cc1-c1c(C)c(C(=O)Nc2c(F)cccc2F)nn1C]

The title compound of example 34 was prepared in analogy to the preparation of the title compound of example 17 through the reaction of intermediate 34b (95 mg) with 2,6-difluoroaniline (50 mg) (58% yield).

LC-MS (Method 2): m/z [M+H]$^+$=398.17 (MW calc.=397.42); R$_t$=0.90 min.

SYNTHESIS EXAMPLE 35

5-(5-Cyclopropyl-2-methoxy-phenyl)-N-(3,5-difluoro-pyridin-4-yl)-1,4-dimethyl-1H-pyrazole-3-carboxylic acid amide

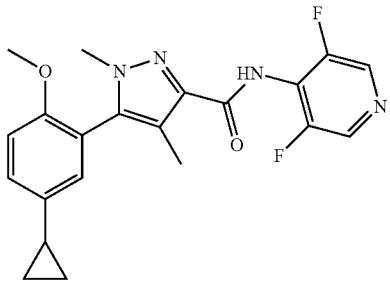 [SMILES: COc1ccc(C2CC2)cc1-c1c(C)c(C(=O)Nc2c(F)cncc2F)nn1C]

The title compound of example 35 was prepared in analogy to the preparation of the title compound of example 17 through the reaction of intermediate 34b (95 mg) with 3,5-difluoropyridin-4-amine (50 mg) (52% yield).

LC-MS (Method 2): m/z [M+H]$^+$=399.16 (MW calc.=398.41); R$_t$=0.85 min.

SYNTHESIS EXAMPLE 36

5-[5-Cyclopropyl-2-(trifluoromethyloxy)-phenyl]-N-(2,6-difluoro-phenyl)-1-methyl-1H-pyrazole-3-carboxylic acid amide Intermediate 36a

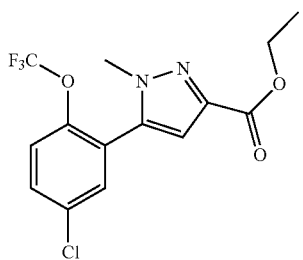 [SMILES: CCOC(=O)c1cc(-c2cc(Cl)ccc2OC(F)(F)F)n(C)n1]

Intermediate 36a was prepared in analogy to the synthesis of intermediate 19b through the reaction of intermediate 15b* (900 mg) with 2-bromo-4-chloro-1-(trifluoromethoxy)benzene (885 mg) (72% yield).

LC-MS (Method 1): m/z [M+H]$^+$=349.2 (MW calc.=348.70); R$_t$=3.9 min.

Intermediate 36b

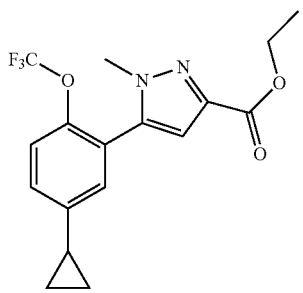 [SMILES: CCOC(=O)c1cc(-c2cc(C3CC3)ccc2OC(F)(F)F)n(C)n1]

Intermediate 36b was prepared in analogy to the preparation of Intermediate 34b starting from intermediate 36a (580 mg) (61% yield).

LC-MS (Method 1): m/z [M+H]$^+$=355.2 (MW calc.=354.32); R$_t$=4.0 min.

5-[5-Cyclopropyl-2-(trifluoromethyloxy)-phenyl]-N-(2,6-difluoro-phenyl)-1-methyl-1H-pyrazole-3-carboxylic acid amide (Example 36)

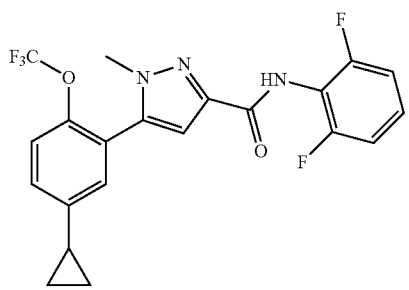 [SMILES: Cn1nc(C(=O)Nc2c(F)cccc2F)cc1-c1cc(C2CC2)ccc1OC(F)(F)F]

The title compound of example 36 was prepared in analogy to the preparation of the title compound of example 17 through the reaction of intermediate 36b (115 mg) with 2,6-difluoroaniline (54 mg) (80% yield).

LC-MS (Method 2): m/z [M+H]$^+$=438.12 (MW calc.=437.36); R$_t$=0.91 min.

SYNTHESIS EXAMPLE 37

5-[5-Cyclopropyl-2-(trifluoromethyloxy)-phenyl]-N-(3,5-difluoro-pyridin-4-yl)-1-methyl-1H-pyrazole-3-carboxylic acid amide

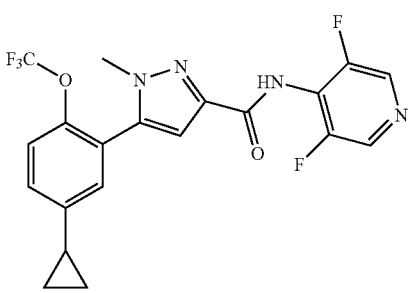 [SMILES: Cn1nc(C(=O)Nc2c(F)cncc2F)cc1-c1cc(C2CC2)ccc1OC(F)(F)F]

The title compound of example 37 was prepared in analogy to the preparation of the title compound of example 17 through the reaction of intermediate 36b (115 mg) with 3,5-difluoropyridin-4-amine (55 mg) (79% yield).

LC-MS (Method 2): m/z [M+H]$^+$=439.11 (MW calc.=438.35); R$_t$=0.86 min.

SYNTHESIS EXAMPLE 38

5-[5-Cyclopropyl-2-(trifluoromethyloxy)-phenyl]-N-(3-fluoro-pyridin-4-yl)-1-methyl-1H-pyrazole-3-carboxylic acid amide

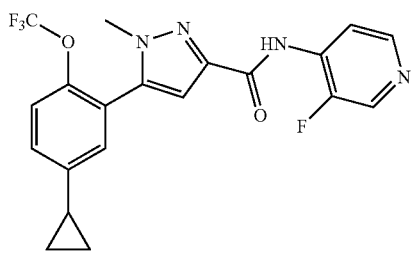 [SMILES: Cn1nc(C(=O)Nc2ccncc2F)cc1-c1cc(C2CC2)ccc1OC(F)(F)F]

The title compound of example 38 was prepared in analogy to the preparation of the title compound of example 17 through the reaction of intermediate 36b (115 mg) with 3-difluoropyridin-4-amine (55 mg) (84% yield).

LC-MS (Method 2): m/z [M+H]$^+$=421.13 (MW calc.=420.36); R$_t$=0.91 min.

SYNTHESIS EXAMPLE 39

5-[4-Cyclopropyl-2-(trifluoromethyloxy)-phenyl]-N-(2,6-difluoro-phenyl)-1-methyl-1H-pyrazole-3-carboxylic acid amide

Intermediate 39a

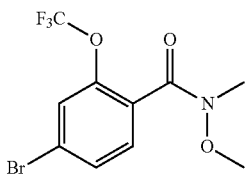 [SMILES: CON(C)C(=O)c1ccc(Br)cc1OC(F)(F)F]

Intermediate 39a was prepared in analogy to the preparation of Intermediate 30a starting from 4-bromo-2-(trifluoromethoxy)benzoic acid (2 g) (90% yield).

Intermediate 39b

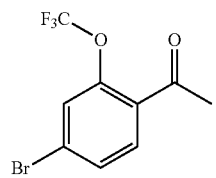

Methyl magnesium chloride (3 M in THF, 4.2 mL) was added to a solution of intermediate 39a (2.06 g) in dry THF (20 mL) and the mixture was stirred at rt for 1 h. Water (5 mL) was added and the volatiles were removed under reduced pressure. The residue was treated with 2 M HCl and was extracted with EtOAc. The combined organic layers were dried and the volatiles were removed under reduced pressure to yield desired compound (88% yield).

Intermediate 39c

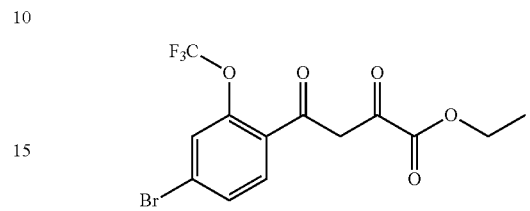

Intermediate 39c was prepared in analogy to the preparation of intermediate 1b starting from intermediate 30b (1.55 g) (96% yield).

LC-MS (Method 1): m/z [M+H]$^+$=383.2 (MW calc.=383.11); R$_t$=4.1 min.

Intermediate 39d

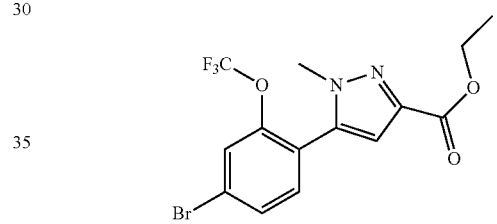

Intermediate 39d was prepared in analogy to the preparation of intermediate 14b starting from intermediate 39c (2.01 mg) (56% yield).

LC-MS (Method 1): m/z [M+H]$^+$=393.1 (MW calc.=393.16); R$_t$=3.9 min.

Intermediate 39e

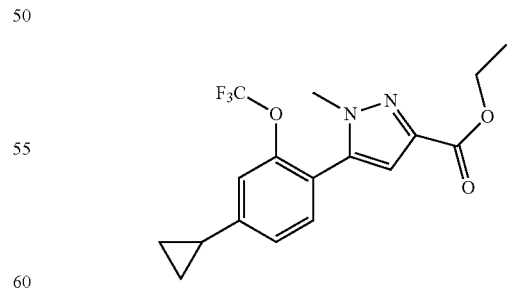

Intermediate 39e was prepared in analogy to the preparation of Intermediate 34b starting from intermediate 39c (600 mg) (91% yield).

LC-MS (Method 1): m/z [M+H]$^+$=355.2 (MW calc.=354.32); R$_t$=4.0 min.

5-[4-Cyclopropyl-2-(trifluoromethyloxy)-phenyl]-N-(2,6-difluoro-phenyl)-1-methyl-1H-pyrazole-3-carboxylic acid amide (Example 39)

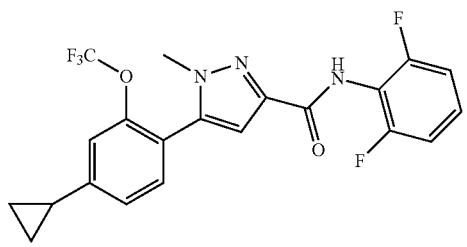 [SMILES: Cn1nc(C(=O)Nc2c(F)cccc2F)cc1-c1ccc(C2CC2)cc1OC(F)(F)F]

The title compound of example 39 was prepared in analogy to the preparation of the title compound of example 17 through the reaction of intermediate 39e (120 mg) with 2,6-difluoroaniline (57 mg) (81% yield).

LC-MS (Method 2): m/z [M+H]$^+$=438.12 (MW calc.=437.36); R$_t$=0.88 min.

SYNTHESIS EXAMPLE 40

5-[4-Cyclopropyl-2-(trifluoromethyloxy)-phenyl]-N-(3,5-difluoro-pyridin-4-yl)-1-methyl-1H-pyrazole-3-carboxylic acid amide

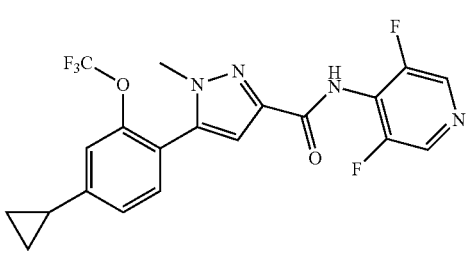 [SMILES: Cn1nc(C(=O)Nc2c(F)cncc2F)cc1-c1ccc(C2CC2)cc1OC(F)(F)F]

The title compound of example 40 was prepared in analogy to the preparation of the title compound of example 17 through the reaction of intermediate 39e (120 mg) with 3,5-difluoropyridin-4-amine (57 mg) (65% yield).

LC-MS (Method 2): m/z [M+H]$^+$=439.11 (MW calc.=438.35); R$_t$=0.84 min.

SYNTHESIS EXAMPLE 41

5-[4-Cyclopropyl-2-(trifluoromethyloxy)-phenyl]-N-(3-fluoro-pyridin-4-yl)-1-methyl-1H-pyrazole-3-carboxylic acid amide

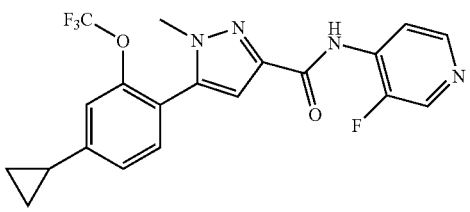 [SMILES: Cn1nc(C(=O)Nc2ccncc2F)cc1-c1ccc(C2CC2)cc1OC(F)(F)F]

The title compound of example 41 was prepared in analogy to the preparation of the title compound of example 17 through the reaction of intermediate 39e (110 mg) with 3-fluoropyridin-4-amine (46 mg) (70% yield).

LC-MS (Method 2): m/z [M+H]$^+$=421.13 (MW calc.=420.36); R$_t$=0.88 min.

SYNTHESIS EXAMPLE 43

4-Amino-N-(3,5-difluoro-pyridin-4-yl)-1-methyl-5-(2-methyl-5-oxazol-2-yl-phenyl)-1H-pyrazole-3-carboxylic acid amide Intermediate 43a

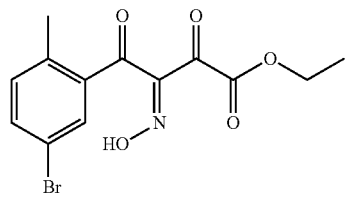 [SMILES: CCOC(=O)C(=O)/C(=N/O)C(=O)c1cc(Br)ccc1C]

A solution of intermediate 1b (5.22 g) in ethanol was charged with N$_2$O$_3$ gas (derived from sodium nitrite 50 g, H$_2$O 20 mL and conc. HCl) and the mixture stirred for 1 h at rt. Volatiles were removed under reduced pressure, the residue dissolved in EtOAc and washed with water (3×). The organic layer was dried and solvent removed under reduced pressure to yield the desired compound (57% yield).

Intermediate 43b

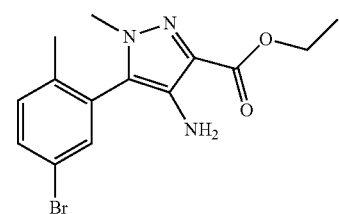 [SMILES: CCOC(=O)c1nn(C)c(-c2cc(Br)ccc2C)c1N]

To a solution of intermediate 43a (3.2 g) in ethanol (100 mL) was added conc. HCl (792 μL) and methyl hydrazine (505 μL) and the mixture was stirred for 1 h at rt. After addition of 1 M HCl (100 mL) and iron (2.65 g) the mixture was heated to reflux for 4 h before volatiles were removed under reduced pressure, the remaining solution neutralized with NaHCO$_3$ and subsequently extracted with DCM. The combined organic layer was dried, solvent removed under reduced pressure and the residue purified by chromatography (SiO$_2$, 65 g, Cy/EtOAc) to yield the desired compound as the more polar isomer (18% yield).

LC-MS (Method 1): m/z [M+H]$^+$=338.1 (MW calc.=337.04); R$_t$=3.5 min.

Intermediate 43c

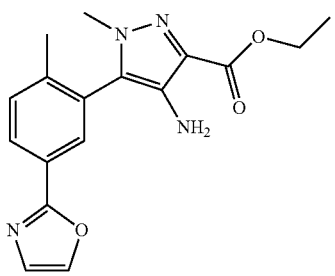 [SMILES: CCOC(=O)c1nn(C)c(-c2cc(-c3ncco3)ccc2C)c1N]

A solution of intermediate 43b (564 mg), 2-(tri-n-butyl-stannyl)oxazole (721 mg) and tetrakis(triphenyl-phosphine) palladium in dry acetonitrile (15 mL) was stirred under an argon atmosphere at 90° C. for 2 h. The volatiles were removed under reduced pressure and the residue was purified by column chromatography (SiO$_2$, potassium carbonate, EtOAc) to yield the desired product (81% yield).

LC-MS (Method 1): m/z [M+H]$^+$=327.2 (MW calc.=326.14); R$_t$=3.2 min.

Intermediate 43d

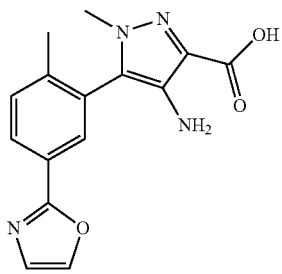 [SMILES: Cc1ccc(-c2ncco2)cc1-c1c(N)c(C(=O)O)nn1C]

A solution of intermediate 43c (182 mg) in ethanol (10 mL) was treated with 1M sodium hydroxide solution (10 mL) and was stirred at reflux for 1 h. The reaction mixture was neutralized with saturated potassium dihydrogenphosphate solution and extracted with $^i$PrOH/CH$_2$Cl$_2$. The combined organic layers were dried and the solvents were removed under reduced pressure to yield the desired product (98% yield).

LC-MS (Method 1): m/z [M+H]$^+$=299.2 (MW calc.=298.11); R$_t$=2.9 min.

4-Amino-N-(3,5-difluoro-pyridin-4-yl)-1-methyl-5-(2-methyl-5-oxazol-2-yl-phenyl)-1H-pyrazole-3-carboxylic acid amide (Example 43)

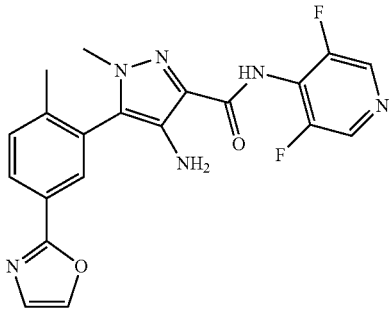 [SMILES: Cc1ccc(-c2ncco2)cc1-c1c(N)c(C(=O)Nc2c(F)cncc2F)nn1C]

A solution of intermediate 43d (164 mg) in thionyl chloride (5 mL) was stirred at 75° C. for 30 min. The volatiles were removed under reduced pressure and the residue was dissolved in dry THF (20 mL). A solution of 4-amino-3,5-difluorpyridine (143 mg) and lithiumhexamethyldisilazane (1M in hexane, 1.1 mL in THF) that was pre-stirred for 30 min was added and the mixture was stirred for 1 h at rt. Water was added followed by extraction with DCM. The combined organic layer was dried and the volatiles were removed under reduced pressure. The residue was purified by chromatography (SiO$_2$, 65 g, Cy/EtOAc) to yield the title compound of example 43 (24% yield).

LC-MS (Method 2): m/z [M+H]$^+$=411.2 (MW calc.=410.38); R$_t$=0.67 min.

SYNTHESIS EXAMPLE 44

4-Amino-N-(2,6-difluoro-phenyl)-5-(2-methoxy-5-thiazol-2-yl-phenyl)-1-methyl-1H-pyrazole-3-carboxylic acid amide

Intermediate 44a

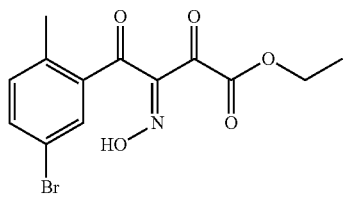 [SMILES: CCOC(=O)C(=O)/C(=N/O)C(=O)c1cc(Br)ccc1C]

Intermediate 44a was prepared in analogy to intermediate 43a by reaction of intermediate 7b (4.0 g) with N$_2$O$_3$ (95% yield).

Intermediate 44b

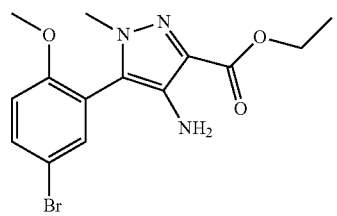 [SMILES: CCOC(=O)c1nn(C)c(-c2cc(Br)ccc2OC)c1N]

Intermediate 44b was prepared in analogy to intermediate 43b by reaction of intermediate 44a (4.1 g) to yield the desired compound as the polar isomer (26% yield).

LC-MS (Method 1): m/z [M+H]$^+$=354.1 (MW calc.=326.14); R$_t$=3.7 min.

Intermediate 44c

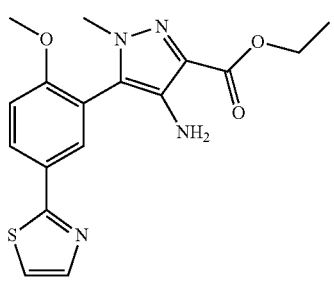 [SMILES: CCOC(=O)c1nn(C)c(-c2cc(-c3nccs3)ccc2OC)c1N]

A solution of intermediate 44b (475 mg), 2-(tri-n-butyl-stannyl)thiazole (551 mg) and tetrakis(triphenylphosphine) palladium (77 mg) in dry acetonitrile (15 mL) was stirred under an argon atmosphere at 90° for 2 h. The volatiles were removed under reduced pressure and the residue was purified by column chromatography (SiO$_2$, potassium carbonate, EtOAc) to yield the desired product (66% yield).
LC-MS (Method 1): m/z [M+H]$^+$=359.2 (MW calc.=358.41); R$_t$=3.2 min.

4-Amino-N-(2,6-difluoro-phenyl)-5-(2-methoxy-5-thiazol-2-yl-phenyl)-1-methyl-1H-pyrazole-3-carboxylic acid amide (Example 44)

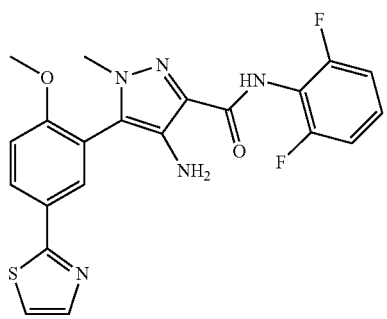 [SMILES: COc1ccc(-c2nccs2)cc1-c1c(N)c(C(=O)Nc2c(F)cccc2F)nn1C]

The title compound of example 44 was prepared in analogy to the preparation of the title compound of example 17 through the reaction of intermediate 44c (100 mg) with 2,6-difluoroaniline (72 mg) (28% yield).
LC-MS (Method 1): m/z [M+H]$^+$=442.2 (MW calc.=441.45); R$_t$=3.5 min.

SYNTHESIS EXAMPLE 45

4-amino-N-(3,5-difluoropyridin-4-yl)-5-(2-methoxy-5-(oxazol-2-yl)phenyl)-1-methyl-1H-pyrazole-3-carboxamide

Intermediate 45a

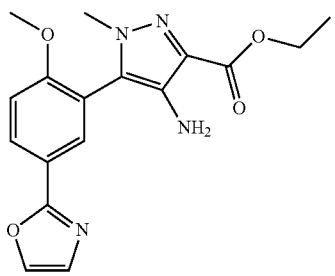 [SMILES: CCOC(=O)c1nn(C)c(-c2cc(-c3ncco3)ccc2OC)c1N]

Intermediate 45a was prepared in analogy to the preparation of intermediate 43c through the reaction of intermediate 44b (1.00 g) with 2-(tri-n-butylstannyl)oxazole (1.11 g) (71% yield).
LC-MS (Method 1): m/z [M+H]$^+$=343.2 (MW calc.=342.35); R$_t$=3.3 min.

Intermediate 45b

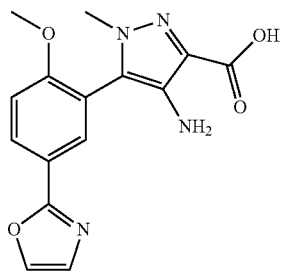 [SMILES: COc1ccc(-c2ncco2)cc1-c1c(N)c(C(=O)O)nn1C]

Intermediate 45a was prepared in analogy to the preparation of intermediate 43d starting from intermediate 45a (435 mg) (88% yield).
LC-MS (Method 1): m/z [M+H]$^+$=315.2 (MW calc.=314.30); R$_t$=2.7 min.

4-amino-N-(3,5-difluoropyridin-4-yl)-5-(2-methoxy-5-(oxazol-2-yl)phenyl)-1-methyl-1H-pyrazole-3-carboxamide (Example 45)

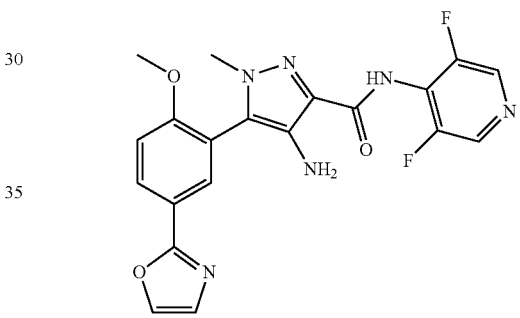

The title compound of example 45 was prepared in analogy to the preparation of the title compound of example 43 through the reaction of intermediate 45b (346 mg) with 4-amino-3,5-difluorpyridine (286 mg mg) (21% yield).
LC-MS (Method 1): m/z [M+H]$^+$=427.2 (MW calc.=426.38); R$_t$=3.2 min.

SYNTHESIS EXAMPLE 46

4-amino-N-(2,6-difluorophenyl)-5-(2-methoxy-5-(oxazol-2-yl)phenyl)-1-methyl-1H-pyrazole-3-carboxamide

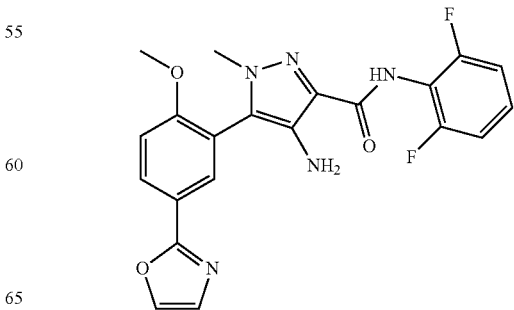

The title compound of example 46 was prepared in analogy to the preparation of the title compound of example 17 through the reaction of intermediate 45a (250 mg) with 2,6-difluoroaniline (282 mg) (38% yield).

LC-MS (Method 1): m/z [M+H]$^+$=426.3 (MW calc.=425.39); R$_t$=3.4 min.

SYNTHESIS EXAMPLE 47

4-amino-N-(3,5-difluoropyridin-4-yl)-5-(2-methoxy-5-(thiazol-2-yl)phenyl)-1-methyl-1H-pyrazole-3-carboxamide Intermediate 47a

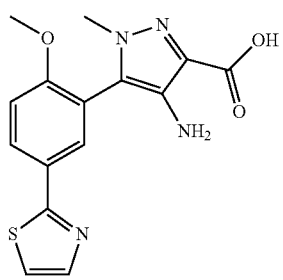 [SMILES: COc1ccc(-c2nccs2)cc1-c1c(N)c(C(=O)O)nn1C]

Intermediate 47a was prepared in analogy to the preparation of intermediate 43d starting from intermediate 44c (270 mg) (93% yield).

LC-MS (Method 1): m/z [M+H]$^+$=331.2 (MW calc.=330.36); R$_t$=2.9 min.

4-amino-N-(3,5-difluoropyridin-4-yl)-5-(2-methoxy-5-(thiazol-2-yl)phenyl)-1-methyl-1H-pyrazole-3-carboxamide (Example 47)

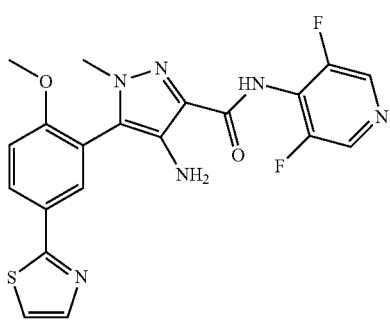 [SMILES: COc1ccc(-c2nccs2)cc1-c1c(N)c(C(=O)Nc2c(F)cncc2F)nn1C]

The title compound of example 47 was prepared in analogy to the preparation of the title compound of example 43 through the reaction of intermediate 47a (230 mg) with 4-amino-3,5-difluorpyridine (181 mg mg) (25% yield).

LC-MS (Method 1): m/z [M+H]$^+$=443.2 (MW calc.=442.44); R$_t$=3.3 min.

SYNTHESIS EXAMPLE 48

4-amino-N-(2,6-difluorophenyl)-5-(5-(5,5-dimethyl-4-oxo-4,5-dihydroisoxazol-3-yl)-2-methoxyphenyl)-1-methyl-1H-pyrazole-3-carboxamide Intermediate 48a

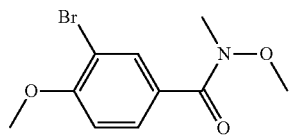

To a suspension of 3-bromo-4-methoxybenzoic acid (5.22 g) in dry CH$_2$Cl$_2$ (80 mL) were consecutively added N,O-dimethylhydroxylamine hydrochloride (2.25 g), EDCI (4.9 g), HOBt (3.81 g) and NEt$_3$ (7 mL) and the mixture was stirred at rt for 3 h. Water was added and the mixture was extracted with EtOAc, the combined organic layers were dried and the volatiles were removed under removed under reduced pressure to yield the desired compound (>99% yield).

LC-MS (Method 1): m/z [M+H]$^+$=274.1 (MW calc.=274.11); R$_t$=3.2 min.

Intermediate 48b

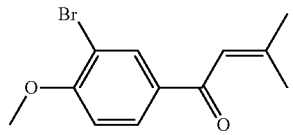

To a solution of intermediate 48a (6.2 g) in dry THF (60 mL) under an argon atmosphere was added 2-methyl-1-propenylmagnesiumbromide (0.5 M in THF, 55 mL) at −30° C. and the mixture was stirred at rt for 2 h. The reaction mixture was treated with aqueous HCl (0.5 M, 28 mL) and was extracted with EtOAc.

The combined organic layers were dried and the volatiles were removed under reduced pressure. The residue was purified by (SiO$_2$, 300 g, Cy/EtOAc) to yield the desired compound (51% yield).

LC-MS (Method 1): m/z [M+H]$^+$=271.1 (MW calc.=269.31); R$_t$=3.8 min.

Intermediate 48c

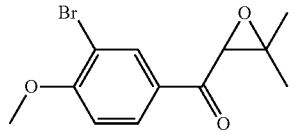

To a solution of intermediate 48b (2.0 g) in MeOH (35 mL) were consecutively added H$_2$O$_2$ (30%, 2.3 mL) and aqueous NaOH (2M, 1.9 mL) and the mixture was stirred at rt for 2 h. The mixture was diluted with water and was extracted with Et$_2$O. The combined organic layers were dried and the volatiles were removed under reduced pressure to yield the desired compound (98% yield).

Intermediate 48d

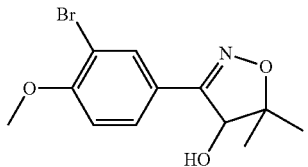

To a solution of intermediate 48c (2.06 g) in MeOH (26 mL) and pyridine (15 mL) was added hydroxylamine hydrochloride (2.19 g) and the mixture was heated to 80° C. for 18 h. The volatiles were removed under reduced pressure and the residue was dissolved in EtOAc and was washed with NaHCO$_3$ (50 mL). The organic layer was dried and the volatiles were removed under reduced pressure to yield the desired compound (71% yield).

LC-MS (Method 1): m/z [M+H]$^+$=301.1 (MW calc.=300.15); R$_t$=3.3 min.

Intermediate 48e

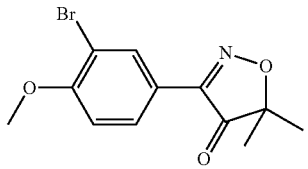

A solution of intermediate 48d (1.47 g) in acetic acid (60 mL) was treated with CrO$_3$ (500 mg), water (3 mL) and concentrated sulfuric acid (0.7 mL) and the mixture was heated to 100° C. for 1 h. Subsequently the mixture was treated with brine and was extracted with EtOAc. The combined organic layers were dried and the volatiles were removed under reduced pressure to yield a solid residue which was washed with EtOH and Et$_2$O to yield the desired compound (48% yield).

LC-MS (Method 1): m/z [M+H]$^+$=298.1 (MW calc.=298.13); R$_t$=3.9 min.

Intermediate 48f

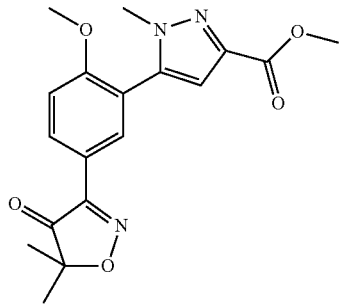 [SMILES: COC(=O)c1cc(-c2cc(C3=NOC(C)(C)C3=O)ccc2OC)n(C)n1]

Intermediate 36a was prepared in analogy to the synthesis of intermediate 19b through the reaction of intermediate 15b (295 mg) and intermediate 48e (300 mg) (70% yield).

LC-MS (Method 1): m/z [M+H]$^+$=358.2 (MW calc.=357.36); R$_t$=3.6 min.

4-amino-N-(2,6-difluorophenyl)-5-(5-(5,5-dimethyl-4-oxo-4,5-dihydroisoxazol-3-yl)-2-methoxyphenyl)-1-methyl-1H-pyrazole-3-carboxamide (Example 48)

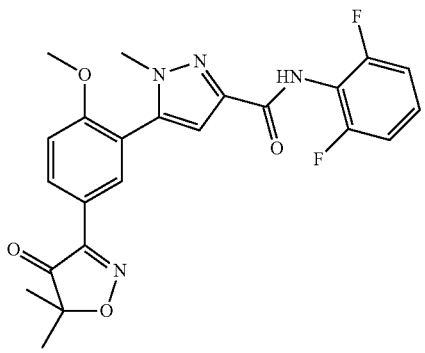 [SMILES: COc1ccc(C2=NOC(C)(C)C2=O)cc1-c1cc(C(=O)Nc2c(F)cccc2F)nn1C]

The title compound of example 48 was prepared in analogy to the preparation of the title compound of example 14 through the reaction of intermediate 48f (100 mg) with 2,6-difluoroaniline (42 mg) (63% yield).

LC-MS (Method 1): m/z [M+H]$^+$=455.2 (MW calc.=454.43); R$_t$=3.7 min.

SYNTHESIS EXAMPLE 49

4-amino-N-(2,6-difluorophenyl)-1-methyl-5-(5-(oxazol-2-yl)-2-(trifluoromethoxy)phenyl)-1H-pyrazole-3-carboxamide Intermediate 49a

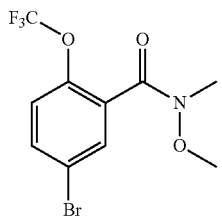 [SMILES: CON(C)C(=O)c1cc(Br)ccc1OC(F)(F)F]

A suspension of 5-bromo-2-(trifluoromethoxy)benzoic acid (1.14 g) in thionyl chloride (5 mL) was heated to 75° C. for 1 h. The volatiles were removed under reduced pressure and the residue was dissolved in CH$_2$Cl$_2$ and N,O-dimethylhydroxylamine hydrochloride (468 mg) and NEt$_3$ (1.11 mL) were added. The mixture was stirred at rt for 3 h and NH$_4$Cl was added. The layers were seperated, the organic layer was washed water, was dried and the volatiles were removed under reduced pressure to yield the desired compound (87%).

Intermediate 49b

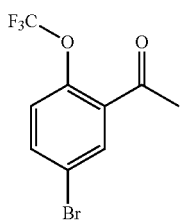

Intermediate 49b was prepared in analogy to the preparation of intermediate 39b starting from intermediate 49a (95% yield).

Intermediate 49c

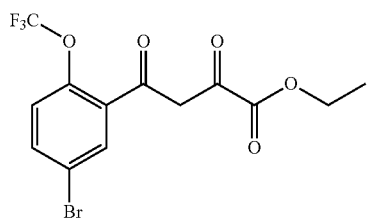

Intermediate 49c was prepared in analogy to the preparation of intermediate 1b starting from intermediate 49b (930 mg) (94% yield).

Intermediate 49d

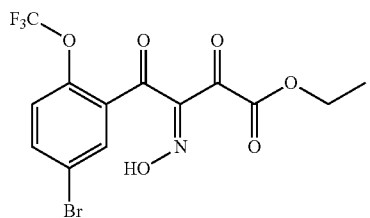 [SMILES: CCOC(=O)C(=O)/C(=N/O)C(=O)c1cc(Br)ccc1OC(F)(F)F]

Intermediate 49d was prepared in analogy to the preparation of intermediate 43a starting from intermediate 49c (3.02 g) (99% yield).

Intermediate 49e

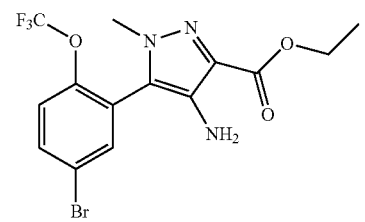 [SMILES: CCOC(=O)c1nn(C)c(-c2cc(Br)ccc2OC(F)(F)F)c1N]

Intermediate 49e was prepared in analogy to intermediate 43b by reaction of intermediate 49d (3.20 g) to yield the desired compound as the polar isomer (18% yield). LC-MS (Method 1): m/z [M+H]$^+$=408.1 (MW calc.=408.17); $R_t$=3.6 min.

Intermediate 49f

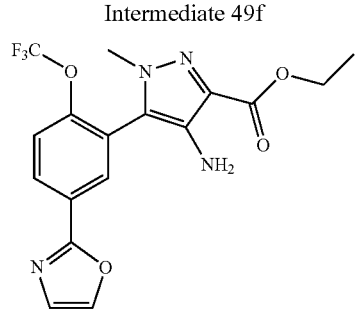

Intermediate 49f was prepared in analogy to the preparation of intermediate 43c through the reaction of intermediate 49e (575 mg) with 2-(tri-n-butylstannyl)oxazole (554 mg) (32% yield).

LC-MS (Method 1): m/z [M+H]$^+$=397.2 (MW calc.=396.32); $R_t$=3.4 min.

4-amino-N-(2,6-difluorophenyl)-1-methyl-5-(5-(oxazol-2-yl)-2-(trifluoromethoxy)phenyl)-1H-pyrazole-3-carboxamide (Example 49)

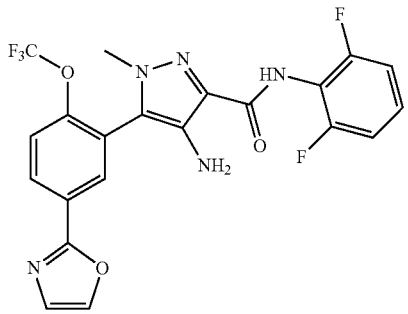 [SMILES: Cn1nc(C(=O)Nc2c(F)cccc2F)c(N)c1-c1cc(-c2ncco2)ccc1OC(F)(F)F]

The title compound of example 49 was prepared in analogy to the preparation of the title compound of example 14 through the reaction of intermediate 49f (166 mg) with 2,6-difluoroaniline (163 mg) (43% yield).

LC-MS (Method 1): m/z [M+H]$^+$=480.2 (MW calc.=479.36); $R_t$=3.6 min.

SYNTHESIS EXAMPLE 50

4-amino-N-(3,5-difluoropyridin-4-yl)-1-methyl-5-(5-(oxazol-2-yl)-2-(trifluoro-methoxy)phenyl)-1H-pyrazole-3-carboxamide

Intermediate 50a

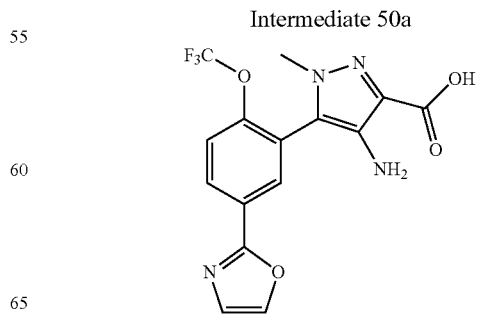

Intermediate 50a was prepared in analogy to the preparation of intermediate 43d starting from intermediate 49f (258 mg) (94% yield).

LC-MS (Method 1): m/z [M+H]$^+$=369.2 (MW calc.=368.27); R$_t$=3.1 min.

4-amino-N-(3,5-difluoropyridin-4-yl)-1-methyl-5-(5-(oxazol-2-yl)-2-(trifluoromethoxy)phenyl)-1H-pyrazole-3-carboxamide (Example 50)

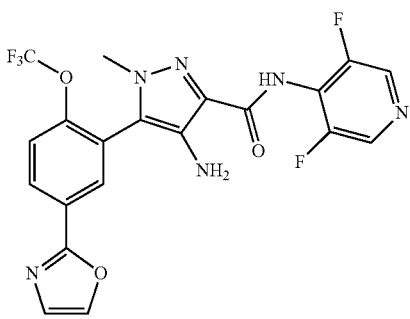 [SMILES: Cn1nc(C(=O)Nc2c(F)cncc2F)c(N)c1-c1cc(-c2ncco2)ccc1OC(F)(F)F]

The title compound of example 50 was prepared in analogy to the preparation of the title compound of example 43 through the reaction of intermediate 50a (221 mg) with 4-amino-3,5-difluorpyridine (156 mg mg) (24% yield).

LC-MS (Method 1): m/z [M+H]$^+$=481.2 (MW calc.=480.35); R$_t$=3.5 min.

Pharmacological Methods

Compounds of the invention have been tested for their effects on CRAC channels according to the following or similar procedures.

HEK Calcium Influx Assay

The effect of compounds of the invention on intracellular [Ca$^{2+}$] was tested in the HEK293 cell line (ECACC).

HEK293 cells were cultured in DMEM/F12/Glutamax (Gibco) containing 10% FCS (Gibco), and maintained at 37° C., 5% CO$_2$. Cell were split twice a week [3·10$^6$ (Mon-Thu) and 1·10$^6$ (Thu-Mon) cells/50 ml medium in T-175 ZK culture flasks, respectively]. 24 hours pre-experiment, cells were seeded on 96 well plates (Poly-D-Lysine 96well Black/Clear Plate, BD Biocoat REF 356640) at a density of 40,000 cells/well in DMEM/F12 (Gibco) containing 10% FCS (Gibco), and maintained at 37° C., 5% CO$_2$.

Prior to store-depletion, cell culture medium was removed and cells were loaded with the a Ca$^{2+}$-sensitive fluorescent dye comprised within the Calcium-4-assay kit (Molecular Devices) in nominally Ca$^{2+}$-free HBS buffer (140 mM NaCl, 4 mM KCl, 0.2 mM MgCl$_2$, 11 mM D-glucose, and 10 mM HEPES, pH 7.4) according to manufacturer's instruction for 60 min at 37° C., 5% CO$_2$.

Passive depletion of intracellular Ca$^{2+}$-stores was then triggered by employing the SERCA inhibitor thapsigargin (2 μM final) for 10 min in the dark (rt). To prevent immediate Ca$^{2+}$-entry via the activated Store-operated channels (SOCs), cells were maintained in Ca$^{2+}$-free HBS buffer comprising 100 μM EGTA during store-depletion.

Intracellular changes in [Ca$^{2+}$] were subsequently monitored with the FLIPR device (Molecular Devices). In brief, baseline imaging post-store depletion was allowed for 1 min before adjusting the extracellular buffer to 3 mM CaCl$_2$. Increases in intracellular [Ca$^{2+}$] due to pre-activated SOC channels were monitored for 15 min until intracellular Ca$^{2+}$ levels had declined into a steady-state. Finally, compounds were administered and Ca$^{2+}$ signals were recorded for additional 10 min.

Inhibition of endogenous SOC in HEK293 cells was quantified employing the average Ca$^{2+}$ signal measured from 9.5-10 min post-administration. Zero percent inhibition (MAX) was defined as the Ca$^{2+}$ signal recorded from wells to which DMSO-only had been added instead of compound. Hundred percent inhibition (MIN) was defined as the signal obtained from wells in which cells haven't been treated with TG prior to Ca$^{2+}$ addition and to which DMSO-only had been added instead of compound. For routine IC$_{50}$ determinations of compounds, 8 concentrations of a serial dilution (1:3.16) were tested, starting off from 10 μM. Reliable IC$_{50}$'s could consequently be determined only, if they were at least sub 2.5-3 μM.

Jurkat IL-2 Production Assay

The effect of compounds of the invention on Interleukin-2 (IL-2) production/release was tested in the Jurkat T cell line (ECACC) clone E6-1.

Jurkat T cells were cultured in DMEM/F12/Glutamax (Gibco) containing 10% FCS (Gibco), and maintained at 37° C., 5% CO$_2$. Cells were split twice a week [5·10$^6$ (Mon-Thu) and 1·10$^7$ (Thu-Mon) cells/50 ml medium in T-175 ZK culture flasks, respectively].

Prior to experiment, cells were seeded on 96 well plates (Cellstar 96 Well; Cat No. 655180, Greiner bio-one) at a density of 5·10$^5$ cells/well in DMEM/F12/Glutamax (Gibco) containing 10% FCS (Gibco), and incubated for 60 min at 37° C., 5% CO$_2$. Subsequently, compounds were added and cells were allowed to incubate for 30 min at 37° C., 5% CO$_2$. Cells were then stimulated with 15 μg/ml Phyto-hemagglutinin (PHA; Sigma) for 22 hours at 37° C., 5% CO$_2$.

Before sampling of the supernatants, cells were spun down (200*g/5 min/RT). The amount of IL-2 released into the supernatant was quantified with the human IL-2 AlphaLisa kit (Perkin Elmer) according to manufacturer's instructions. Luminescence proximity measurements were carried out in the Synergy H4 reader (BioTek) employing the fluorescence setting of the reader (ex: 680/30 nm; em: 620/40 nm).

Inhibition of IL-Production/Release in/from Jurkat T Cells Cells was Quantified as Follows:

Zero percent inhibition (MAX) was defined as the [IL-2] determined in supernatants derived from cells to which PHA & DMSO-only had been added instead of compound. Hundred percent inhibition (MIN) was defined as the [IL-2] determined in supernatants derived from cells that had been pre-treated with 1 μM CyclosporineA (Sigma) before the addition of 15 μg/ml PHA.

For routine IC50 determinations of compounds, 8 concentrations of a serial dilution (1:3.16) were tested, starting off from 10 μM.

TABLE 2

Exemplary compounds of the invention exhibit inhibition of the CRAC channel (Calcium influx assay/FLPR) and inhibition of the IL-2 prodction in these assays within the following ranges: % inhibition @ 10 μM: >70% (A); 50%-70% (B); <50% (C); IC$_{50}$ values: <0.5 μM (A); 0.5-1.0 μM (B); >1.0-5.0 μM (C) and IC$_{50}$ not determined (n.d.).

| Example No. | % inhib. [@ 10 μM] FLIPR | IC$_{50}$ [μM] IL-2 |
|---|---|---|
| 1 | A | C |
| 2 | B | n.d. |
| 3 | C | A |
| 4 | B | C |
| 5 | B | C |

TABLE 2-continued

Exemplary compounds of the invention exhibit inhibition of the CRAC channel (Calcium influx assay/FLPR) and inhibition of the IL-2 prodction in these assays within the following ranges: % inhibition @ 10 µM: >70% (A); 50%-70% (B); <50% (C); IC$_{50}$ values: <0.5 µM (A); 0.5-1.0 µM (B); >1.0-5.0 µM (C) and IC$_{50}$ not determined (n.d.).

| Example No. | % inhib. [@ 10 µM] FLIPR | IC$_{50}$ [µM] IL-2 |
|---|---|---|
| 6 | B | C |
| 7 | C | B |
| 8 | A | B |
| 9 | B | C |
| 10 | C | A |
| 11 | A | C |
| 12 | A | A |
| 13 | C | A |
| 14 | A | A |
| 15 | A | C |
| 16 | A | A |
| 17 | B | n.d. |
| 18 | C | B |
| 19 | C | C |
| 20 | B | B |
| 21 | B | n.d. |
| 22 | A | C |
| 23 | C | C |
| 24 | A | C |
| 25 | C | C |
| 26 | C | C |
| 27 | A | B |
| 28 | C | C |
| 29 | A | n.d. |
| 30 | A | B |
| 31 | B | C |
| 32 | C | C |
| 33 | B | B |
| 34 | A | B |
| 35 | A | B |
| 36 | A | A |
| 37 | A | A |
| 38 | A | C |
| 39 | A | A |
| 40 | A | A |
| 41 | A | C |
| 43 | C | C |
| 44 | C | C |
| 45 | C | C |
| 46 | C | C |
| 47 | C | C |
| 48 | C | B |
| 49 | B | B |
| 50 | C | C |

The invention claim is:
1. A compound of general formula (I),

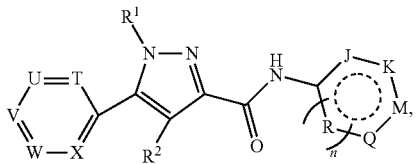

wherein
R$^1$ denotes H; C$_{1-4}$-aliphatic residue, unsubstituted or mono- or polysubstituted; or
C$_{3-6}$-cycloaliphatic residue or a 3 to 7 membered heterocycloaliphatic residue, in each case unsubstituted or mono- or polysubstituted and in each case optionally connected via a C$_{1-4}$ aliphatic group, which in turn may be unsubstituted or mono- or polysubstituted;

with the proviso that if R$^1$ represents a 3 to 7 membered heterocycloaliphatic residue, said 3 to 7 membered heterocycloaliphatic residue is connected to the remaining part of the structure according to general formula (I) via a carbon atom of the 3 to 7 membered heterocycloaliphatic residue;

R$^2$ denotes H; F; Cl; Br; I; NO$_2$; CN; CF$_3$; CF$_2$H; CFH$_2$; R$^{13}$; OH; O—R$^{13}$; NH$_2$; N(H)R$^{13}$; or N(R$^{13}$)$_2$;

T represents C—R$^3$ or N or N$^+$—O$^-$, U represents C—R$^4$ or N or N$^+$—O$^-$, V represents C—R$^5$, W represents C—R$^6$ or N or N$^+$—O$^-$, and X represents C—R$^7$ or N or N$^+$—O$^-$, with the proviso that 0, 1, 2 or 3 of variables T, U, W and X independently of one another represent(s) either N or N$^+$—O$^-$, whereof 0 or 1 of variables T, U, W and X independently of one another represent(s) N$^+$—O$^-$ and wherein at least one of R$^4$, R$^5$ and R$^6$ is selected from the group consisting of
an unsubstituted or mono- or polysubstituted C$_{3-6}$-cycloaliphatic residue;
an unsubstituted or mono- or polysubstituted 3 to 7 membered heterocycloaliphatic residue;
an unsubstituted or mono- or polysubstituted aryl;
and an unsubstituted or mono- or polysubstituted heteroaryl, and the remaining substituents of R$^3$, R$^4$, R$^5$, R$^6$ and R$^7$ are independently of one another selected from the group consisting of H; F; Cl; Br; I; NO$_2$; CN; CF$_3$; CF$_2$H; CFH$_2$; CF$_2$Cl; CFCl$_2$; R$^{13}$; R$^{14}$; C(=O)OH; C(=O)—R$^{13}$; C(=O)R$^{14}$; C(=O)—OR$^{13}$; C(=O)—OR$^{14}$; C(=O)—N(H)(OH); C(=N—OH)—H; C(=N—OH)—R$^{13}$; C(=N—OH)—R$^{14}$; C(=N—O—R$^{13}$)—H; C(=N—O—R$^{13}$)—R$^{13}$; C(=N—O—R$^{13}$)—R$^{14}$; C(=O)NH$_2$; C(=O)—N(H)R$^{13}$; C(=O)—N(R$^{13}$)$_2$; C(=O)—N(H)R$^{14}$; C(=O)—N(R$^{14}$)$_2$; C(=O)—N(R$^{13}$)(R$^{14}$); C(=O)—N(R$^a$)(R$^b$); OH; OR$^{13}$; OCF$_3$; OCF$_2$H; OCFH$_2$; OCF$_2$Cl; OCFCl$_2$; OR—; O—C(=O)R$^{13}$; O—C(=O)R$^{14}$; O—C(=O)—N(H)R$^{13}$; O—C(=O)—N(H)R$^{14}$; O—C(=O)—N(R$^{13}$)$_2$; O—C(=O)—N(R$^{14}$)$_2$; O—C(=O)—N(R$^{13}$)(R$^{14}$); O—C(=O)—N(R$^a$)(R$^b$); NH$_2$; N(H)R$^{13}$; N(R$^{13}$)$_2$; N(H)R$^{14}$; N(R$^{14}$)$_2$; N(R$^{13}$)(R$^{14}$); N(R$^a$)(R$^b$); NH—C(=O)—R$^{14}$; NH—C(=O)—R$^{13}$; N(R$^{13}$)—C(=O)—R$^{13}$; N(R$^{13}$)—C(=O)—R$^{14}$; NH—S(=O)$_2$—R$^{13}$; N(R$^{13}$)—S(=O)$_2$—R$^{13}$; NH—S(=O)$_2$—R$^{14}$; N(R$^{13}$)—S(=O)$_2$—R$^{14}$; N(H)—C(=O)—OR$^{13}$; N(H)—C(=O)—OR$^{14}$; N(R$^{13}$)—C(=O)—OR$^{13}$; N(R$^{13}$)—C(=O)—OR$^{14}$; N(H)—C(=O)—NH$_2$; N(H)—C(=O)—N(H)R$^{13}$; N(H)—C(=O)—N(H)R$^{14}$; N(H)—C(=O)—N(R$^{13}$)$_2$; N(H)—C(=O)—N(R$^{14}$)$_2$; N(H)—C(=O)—N(R$^{13}$)(R$^{14}$); N(H)—C(=O)—N(R$^a$)(R$^b$); N(R$^{13}$)—C(=O)—NH$_2$; N(R$^{13}$)—C(=O)—N(H)R$^{13}$; N(R$^{13}$)—C(=O)—N(H)R$^{14}$; N(R$^{13}$)—C(=O)—N(R$^{13}$)$_2$; N(R$^{13}$)—C(=O)—N(R$^{14}$)$_2$; N(R$^{13}$)—C(=O)—N(R$^{13}$)(R$^{14}$); N(R$^{13}$)—C(=O)—N(R$^a$)(R$^b$); SH; S—R$^{13}$; SCF$_3$; S—R$^{14}$; S(=O)$_2$OH; S(=O)$_2$—R$^{13}$; S(=O)$_2$—R$^{14}$; S(=O)—R$^{13}$; S(=O)—R$^{14}$; S(=O)$_2$—OR$^{13}$; S(=O)$_2$—OR$^{14}$; S(=O)$_2$—N(H)(R$^{13}$); S(=O)$_2$—N(R$^{13}$)$_2$; S(=O)$_2$—N(H)(R$^{14}$); S(=O)$_2$—N(R$^{13}$)(R$^{14}$); and S(=O)$_2$—N(R$^a$)(R$^b$);

n represents 0 or 1,
wherein, if n represents 1, then
J represents C—R$^8$ or N or N$^+$—O$^-$,
K represents C—R$^9$ or N or N$^+$—O$^-$,
M represents C—R$^{10}$ or N or N$^+$—O$^-$,
Q represents C—R$^{11}$ or N or N$^+$—O$^-$, and
R represents C—R$^{12}$ or N or N$^+$—O$^-$, with the proviso that 0, 1, 2 or 3 of variables J, K, M, Q and R independently of one another represent(s) either N or $N^+$—$O^-$, whereof 0 or 1 of variables J, K, M, Q and R independently represents $N^+$—$O^-$, wherein, if n represents 0, then J represents C—$R^8$ or N or N—$O^-$ or O or S or NH or N($C_{1-4}$-aliphatic residue), K represents C—$R^9$ or N or $N^+$—$O^-$ or O or S or NH or N($C_{1-4}$-aliphatic residue), M represents C—$R^{10}$ or N or $N^+$—$O^-$ or O or S or NH or N($C_{1-4}$-aliphatic residue) and Q represents C—$R^{11}$ or N or $N^+$—$O^-$ or O or S or NH or N($C_{1-4}$-aliphatic residue), with the proviso that one of J, K, M and Q represents O or S or NH or N($C_{1-4}$-aliphatic residue) and the remaining of J, K, M and Q independently represent C—$R^8$, respectively C—$R^9$, respectively C—$R^{10}$, respectively C—$R^{11}$ or N or $N^+$—$O^-$ and with the proviso that 0, 1, 2 or 3 of J, K, M and Q independently of one another represent either N or $N^+$—$O^-$, whereof 0 or 1 of variables J, K, M and Q represents $N^+$—$O^-$, wherein $R^8$, $R^9$, $R^{10}$, $R^{11}$ and $R^{12}$ are independently of one another selected from the group consisting of H; F; Cl; Br; I; $NO_2$; CN; $CF_3$; $CF_2H$; $CFH_2$; $CF_2Cl$; $CFCl_2$; $R^{13}$; $R^{14}$; C(=O)OH; C(=O)—$R^{13}$; C(=O)$R^{14}$; C(=O)—$OR^{13}$; C(=O)—$OR^{14}$; C(=O)—N(H)(OH); C(=N—OH)—H; C(=N—OH)—$R^{13}$; C(=N—OH)—$R^{14}$; C(=N—O—$R^{13}$)—H; C(=N—O—$R^{13}$)—$R^{13}$; C(=N—O—$R^{13}$)—$R^{14}$; C(=O)$NH_2$; C(=O)—N(H)$R^{13}$; C(=O)—N($R^{13}$)$_2$; C(=O)—N(H)$R^{14}$; C(=O)—N($R^{14}$)$_2$; C(=O)—N($R^{13}$)($R^{14}$); C(=O)—N($R^a$)($R^b$); OH; $OR^{13}$; $OCF_3$; $OCF_2H$; $OCFH_2$; $OCF_2Cl$; $OCFCl_2$; $OR^{14}$; O—C(=O)$R^{13}$; O—C(=O)$R^{14}$; O—C(=O)—N(H)$R^{13}$; O—C(=O)—N(H)$R^{14}$; O—C(=O)—N($R^1$)$_2$; O—C(=O)—N($R^{14}$)$_2$; O—C(=O)—N($R^{13}$)($R^{14}$); O—C(=O)—N($R^a$)($R^b$); $NH_2$; N(H)$R^{13}$; N($R^{13}$)$_2$; N(H)$R^{14}$; N($R^{14}$)$_2$; N($R^{13}$)($R^{14}$); N($R^a$)($R^b$); NH—C(=O)—$R^{14}$; NH—C(=O)—$R^{13}$; N($R^{13}$)—C(=O)—$R^{13}$; N($R^{13}$)—C(=O)—$R^{14}$; NH—S(=O)$_2$—$R^{13}$; N($R^{13}$)—S(=O)$_2$—$R^{13}$; NH—S(=O)$_2$—$R^{14}$; N($R^{13}$)—S(=O)$_2$—$R^{14}$; N(H)—C(=O)—$OR^{13}$; N(H)—C(=O)—$OR^{14}$; N($R^{13}$)—C(=O)—$OR^{13}$; N($R^{13}$)—C(=O)—$OR^{14}$; N(H)—C(=O)—$NH_2$; N(H)—C(=O)—N(H)$R^{13}$; N(H)—C(=O)—N(H)$R^{14}$; N(H)—C(=O)—N($R^{13}$)$_2$; N(H)—C(=O)—N($R^{14}$)$_2$; N(H)—C(=O)—N($R^{13}$)($R^{14}$); N(H)—C(=O)—N($R^a$)($R^b$); N($R^{13}$)—C(=O)—$NH_2$; N($R^{13}$)—C(=O)—N(H)$R^{13}$; N($R^{13}$)—C(=O)—N(H)$R^{14}$; N($R^{13}$)—C(=O)—N($R^{13}$)$_2$; N($R^{13}$)—C(=O)—N($R^{14}$)$_2$; N($R^{13}$)—C(=O)—N($R^{13}$)($R^{14}$); N($R^{13}$)—C(=O)—N($R^a$)($R^b$); SH; S—$R^{13}$; $SCF_3$; S—$R^{14}$; S(=O)$_2$OH; S(=O)$_2$—$R^{13}$; S(=O)$_2$—$R^{14}$; S(=O)—$R^{13}$; S(=O)—$R^{14}$; S(=O)$_2$—$OR^{13}$; S(=O)$_2$—$OR^{14}$; S(=O)$_2$—N(H)($R^{13}$); S(=O)$_2$—N($R^{13}$)$_2$; S(=O)$_2$—N(H)($R^{14}$); S(=O)$_2$—N($R^{13}$)($R^{14}$); and S(=O)$_2$—N($R^a$)($R^b$);

and additionally $R^{10}$ may represent N(H)—S(=O)$_2$—$NH_2$;

with the proviso that at least one of $R^8$, $R^9$, $R^{10}$, $R^{11}$ and $R^{12}$ does not denote H;

each $R^{13}$ independently of each other denotes $C_{1-8}$-aliphatic residue, unsubstituted or mono- or polysubstituted;

or $C_{3-6}$-cycloaliphatic residue or 3 to 7 membered heterocycloaliphatic residue, in each case unsubstituted or mono- or polysubstituted;

or $C_{3-6}$-cycloaliphatic residue or 3 to 7 membered heterocycloaliphatic residue, in each case unsubstituted or mono- or polysubstituted, and in each case connected via a $C_{1-4}$-aliphatic residue, unsubstituted or mono- or polysubstituted;

each $R^{14}$ independently of each other denotes aryl and heteroaryl residue, in each case independently of one another unsubstituted or mono- or polysubstituted, or aryl and heteroaryl residue, in each case independently of one another unsubstituted or mono- or polysubstituted and in each case connected via a $C_{1-4}$-aliphatic group, unsubstituted or mono- or polysubstituted;

$R^a$ and $R^b$ together with the N-atom connecting them form a 3 to 7 membered heterocyclic residue, unsubstituted or mono- or polysubstituted;

optionally in the form of a single stereoisomer or a mixture of stereoisomers, in the form of the free compound and/or a physiologically acceptable salt thereof and/or a physiologically acceptable solvate thereof.

2. A compound according to claim 1, wherein $R^2$ is selected from the group consisting of H; F; Cl; Br; CN; $CF_3$; $CF_2H$; $CFH_2$; $R^{13}$; OH; O—$R^{13}$; $NH_2$; N(H)$R^{13}$; and N($R^{13}$)$_2$, wherein $R^{13}$ independently of each other denotes $C_{1-4}$ aliphatic residue, unsubstituted or mono- or polysubstituted.

3. A compound according to claim 1 wherein $R^1$ is selected from the group consisting of unsubstituted $C_{1-4}$-aliphatic residue and unsubstituted cyclopropyl.

4. A compound according to claim 1 wherein, n represents 1, and J represents C—$R^8$, K represents C—$R^9$, M represents C—$R^{10}$ or N or or $N^+$—$O^-$, Q represents C—$R^{11}$ and R represents C—$R^{12}$.

5. A compound according to claim 1 wherein n represents 1, J represents C—$R^8$ and/or R represents C—$R^{12}$, wherein $R^8$ and $R^{12}$ are independently of one another selected from the group consisting of H; $CH_3$; $CF_3$; $CF_2H$; $CFH_2$; $CF_2Cl$; $CFCl_2$; $CH_2CH_3$; CN; OH; $OCH_3$; $OCHF_2$; $OCH_2F$; $OCHF_2$; $OCF_3$; $NH_2$; $NHCH_3$; N($CH_3$)$_2$; NH(C=O)$CH_3$; F; Cl and Br, with the proviso that at least one of $R^8$ and $R^{12}$ does not denote H.

6. A compound according to claim 1 wherein n represents 1, M represents N or $N^+$—$O^-$ or C—$R^{10}$, wherein $R^{10}$ is selected from the group consisting of H; F; Cl; CN; $CF_3$; $CF_2H$; $CFH_2$; $CF_2Cl$; $CFCl_2$; a $C_{1-8}$-aliphatic residue; C(=O)OH; C(=O)—$NH_2$; C(=O)—$C_{1-8}$-aliphatic residue; C(=O)O—$C_{1-8}$-aliphatic residue; C(=O)NH—$C_{1-8}$-aliphatic residue; C(=O)N($C_{1-8}$-aliphatic residue)$_2$; OH; O—$C_{1-8}$-aliphatic residue; $OCF_3$; $OCF_2H$; $OCFH_2$; O—C(=O)—$C_{1-8}$-aliphatic residue; $NH_2$; N($C_{1-8}$-aliphatic residue)$_2$; N(H)—C(=O)—$C_{1-8}$-aliphatic residue; N($C_{1-8}$-aliphatic residue)-S(=O)$_2$—$C_{1-8}$-aliphatic residue; and N(H)—S(=O)$_2$—$NH_2$.

7. A compound according to claim 1 wherein T represents C—$R^3$, U represents C—$R^4$, V represents C—$R^5$, W represents C—$R^6$, and X represents C—$R^7$.

8. A compound according to claim 1 wherein one of $R^4$, $R^5$ and $R^6$ is selected from the group consisting of an unsubstituted or mono- or polysubstituted $C_{3-6}$-cycloaliphatic residue, an unsubstituted or mono- or polysubstituted 3 to 7 membered heterocycloaliphatic residue, and
an unsubstituted or mono- or polysubstituted heteroaryl.

9. A compound according to claim 8 wherein one of $R^4$, $R^5$ and $R^6$ is selected from the group consisting of
cyclopropyl,
a 3 to 7 membered heterocycloaliphatic residue selected from the group consisting of pyrrolidinyl, pyrrolinyl, pyrazolinyl, isoxazolinyl, oxazolinyl, isoxazolinyl, oxadiazolinyl, tetrahydropyranyl, dihydropyrazinyl, pyrazinyl and morpholinyl, wherein the 3 to 7 membered heterocycloaliphatic residue is unsubstituted or mono- or di-substituted with at least one substituent selected from the group consisting of =O, $CH_3$, and $CH_2CH_3$, and
heteroaryl selected from the group consisting of thiazolyl, thiadiazolyl, oxazolyl, isoxazolyl, thienyl, pyrrolyl, pyrazolyl, oxadiazolyl, tetrazolyl, triazolyl, pyridyl and pyrimidinyl, wherein the heteroaryl is unsubstituted or mono- or di-substituted with at least one substituent selected from the group consisting of OH, $NH_2$, $CH_3$, and $CH_2CH_3$,
and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted O—$C_{1-4}$-aliphatic residue,
with the proviso that at least one of the remaining substituents of $R^3$, $R^4$, $R^5$, $R^6$ and $R^7$ does not denote H.

10. A compound according to claim 1 wherein
$R^1$ denotes an unsubstituted $C_{1-4}$-aliphatic residue;
$R^2$ denotes H; F; Cl, OH, $NH_2$, $N(CH_3)_2$, $CH_2NH_2$, $CH_2$—$N(CH_3)_2$, $CH_2OH$; or an unsubstituted $C_{1-4}$ aliphatic residue;
T represents C—$R^3$ or N, U represents C—$R^4$ or N, V represents C—$R^5$, W represents C—$R^6$ or N, and X represents C—$R^7$ or N,
with the proviso that 0, 1, 2 or 3 of variables T, U, W and X independently of one another represent(s) N,
wherein one of $R^4$, $R^5$ and $R^6$ is selected from the group consisting of
a $C_{3-6}$-cycloaliphatic residue,
a 3 to 7 membered heterocycloaliphatic residue, wherein the 3 to 7 membered heterocycloaliphatic residue is unsubstituted or mono- or di-substituted with at least one substituent, selected from the group consisting of =O, $CH_3$, and $CH_2CH_3$, and
a heteroaryl,
and the remaining substituents of $R^3$, $R^4$, $R^5$, $R^6$ and $R^7$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; cyclopropyl; OH; and an unsubstituted O—$C_{1-4}$-aliphatic residue,
with the proviso that at least one of the remaining substituents of $R^3$, $R^4$, $R^5$, $R^6$ and $R^7$ does not denote H;
n represents 1,
J represents C—$R^8$ and/or R represents C—$R^{12}$,
wherein $R^8$ and $R^{12}$ are independently of one another selected from the group consisting of H; $CH_3$; $CF_3$; $CF_2H$; $CFH_2$; $CF_2Cl$; $CFCl_2$; $CH_2CH_3$; CN; OH, $OCH_3$, $OCHF_2$, $OCH_2F$; $OCHF_2$; $OCF_3$; $NH_2$; $NHCH_3$; $N(CH_3)_2$; NH(C=O)$CH_3$; F; Cl and Br,
with the proviso that at least one of $R^8$ and $R^{12}$ does not denote H;
K represents C—$R^9$ and Q represents C—$R^{11}$,
wherein $R^9$ and $R^{11}$ are independently of one another selected from the group consisting of H; F; Cl; Br; I; CN; $CF_3$; $CF_2H$; $CFH_2$; $OCF_3$; $OCF_2H$; $OCFH_2$; an unsubstituted $C_{1-4}$-aliphatic residue; OH; and an unsubstituted O—$C_{1-4}$-aliphatic residue;
and
M represents N or $N^+$—$O^-$ or C—$R^{10}$,
wherein $R^{10}$ is selected from the group consisting of H; F; Cl; $OCH_3$; CN; $CH_3$; $CF_3$; $CF_2H$ and $CFH_2$,
optionally in the form of a single stereoisomer or a mixture of stereoisomers, in the form of the free compound and/or a physiologically acceptable salt and/or a physiologically acceptable solvate thereof.

11. A compound selected from the group consisting of
1  N-(3-Fluoro-pyridin-4-yl)-1-methyl-5-(2-methyl-5-thiazol-2-yl-phenyl)-1H-pyrazole-3-carboxylic acid amide
2  N-(3-Fluoro-pyridin-4-yl)-1-methyl-5-(2-methyl-5-oxazol-2-yl-phenyl)-1H-pyrazole-3-carboxylic acid amide
3  N-(2,6-Difluoro-phenyl)-1-methyl-5-(2-methyl-5-thiazol-2-yl-phenyl)-1H-pyrazole-3-carboxylic acid amide
4  N-(4-Methoxyphenyl)-1-methyl-5-(2-methyl-5-thiazol-2-yl-phenyl)-1H-pyrazole-3-carboxylic acid amide
5  N-(4-Fluorophenyl)-1-methyl-5-(2-methyl-5-thiazol-2-yl-phenyl)-1H-pyrazole-3-carboxylic acid amide
6  1-Methyl-N-(3-methyl-pyridin-4-yl)-5-(2-methyl-5-thiazol-2-yl-phenyl)-1H-pyrazole-3-carboxylic acid amide
7  N-(3-Fluoro-pyridin-4-yl)-5-(2-methoxy-5-thiazol-2-yl-phenyl)-1-methyl-1H-pyrazole-3-carboxylic acid amide
8  N-(2,6-Difluoro-phenyl)-5-(2-methoxy-5-thiazol-2-yl-phenyl)-1-methyl-1H-pyrazole-3-carboxylic acid amide
9  5-(2-Chloro-5-thiazol-2-yl-phenyl)-N-(3-fluoro-pyridin-4-yl)-1-methyl-1H-pyrazole-3-carboxylic acid amide
10  5-(2-Chloro-5-thiazol-2-yl-phenyl)-N-(2,6-difluoro-phenyl)-1-methyl-1H-pyrazole-3-carboxylic acid amide
11  N-(3-Fluoro-pyridin-4-yl)-1-methyl-5-(2-methyl-5-pyridin-4-yl-phenyl)-1H-pyrazole-3-carboxylic acid amide
12  N-(2,6-Difluoro-phenyl)-1-methyl-5-(2-methyl-5-pyridin-4-yl-phenyl)-1H-pyrazole-3-carboxylic acid amide
13  N-(2,6-Difluoro-phenyl)-1-methyl-5-(2-methyl-5-pyrimidin-5-yl-phenyl)-1H-pyrazole-3-carboxylic acid amide
14  N-(2,6-Difluoro-phenyl)-1-methyl-5-(3-thiazol-2-yl-phenyl)-1H-pyrazole-3-carboxylic acid amide
15  5-(5-Cyclopropyl-2-methoxy-phenyl)-N-(3-fluoro-pyridin-4-yl)-1-methyl-1H-pyrazole-3-carboxylic acid amide
16  5-(5-Cyclopropyl-2-methoxy-phenyl)-N-(2,6-difluoro-phenyl)-1-methyl-1H-pyrazole-3-carboxylic acid amide
17  5-(2-Cyclopropyl-5-methyl-pyrimidin-4-yl)-N-(2,6-difluoro-phenyl)-1-methyl-1H-pyrazole-3-carboxylic acid amide
18  N-(2,6-Difluoro-phenyl)-1-methyl-5-(2-methyl-5-oxazol-2-yl-phenyl)-1H-pyrazole-3-carboxylic acid amide
19  N-(2,6-Difluoro-phenyl)-1-methyl-5-[2-methyl-5-(3-methyl-[1,2,4]oxadiazol-5-yl)-phenyl]-1H-pyrazole-3-carboxylic acid amide 20  5-[5-(2-Amino-pyridin-4-yl)-2-methyl-phenyl]-N-(2,6-difluoro-phenyl)-1-methyl-1H-pyrazole-3-carboxylic acid amide
21  N-(3-Fluoro-pyridin-4-yl)-1-methyl-5-(2-methyl-5-tetrahydro-pyran-4-yl-phenyl)-1H-pyrazole-3-carboxylic acid amide
22  N-(2,6-Difluoro-phenyl)-1-methyl-5-(2-methyl-5-tetrahydro-pyran-4-yl-phenyl)-1H-pyrazole-3-carboxylic acid amide
23  N-(2,6-Difluoro-phenyl)-1-methyl-5-[2-methyl-5-(1-methyl-1H-[1,2,4]triazol-3-yl)-phenyl]-1H-pyrazole-3-carboxylic acid amide
24  N-(2,6-Difluoro-phenyl)-1-methyl-5-(2-methyl-4-thiazol-2-yl-phenyl)-1H-pyrazole-3-carboxylic acid amide
25  N-(2,6-Difluoro-phenyl)-1,4-dimethyl-5-(2-methyl-5-thiazol-2-yl-phenyl)-1H-pyrazole-3-carboxylic acid amide
26  N-(3-Fluoro-pyridin-4-yl)-1,4-dimethyl-5-(2-methyl-5-thiazol-2-yl-phenyl)-1H-pyrazole-3-carboxylic acid amide
27  N-(2,6-Difluoro-phenyl)-1,4-dimethyl-5-(3-thiazol-2-yl-phenyl)-1H-pyrazole-3-carboxylic acid amide
28  N-(2,6-Difluoro-phenyl)-1-methyl-5-[2-methyl-5-(5-methyl-4H-[1,2,4]triazol-3-yl)-phenyl]-1H-pyrazole-3-carboxylic acid amide
29  N-(3-Fluoro-pyridin-4-yl)-1,4-dimethyl-5-(3-thiazol-2-yl-phenyl)-1H-pyrazole-3-carboxylic acid amide
30  N-(2,6-Difluoro-phenyl)-1-methyl-5-[5-oxazol-2-yl-2-(trifluoromethyloxy)-phenyl]-1H-pyrazole-3-carboxylic acid amide
31  N-(3-Fluoro-pyridin-4-yl)-1-methyl-5-[5-oxazol-2-yl-2-(trifluoromethyloxy)-phenyl]-1H-pyrazole-3-carboxylic acid amide
32  N-(2,6-Difluoro-phenyl)-1-methyl-5-[2-methyl-5-(4H-[1,2,4]triazol-3-yl)-phenyl]-1H-pyrazole-3-carboxylic acid amide
33  N-(3,5-Difluoro-pyridin-4-yl)-1-methyl-5-[5-oxazol-2-yl-2-(trifluoromethyloxy)-phenyl]-1H-pyrazole-3-carboxylic acid amide
34  5-(5-Cyclopropyl-2-methoxy-phenyl)-N-(2,6-difluoro-phenyl)-1,4-dimethyl-1H-pyrazole-3-carboxylic acid amide
35  5-(5-Cyclopropyl-2-methoxy-phenyl)-N-(3,5-difluoro-pyridin-4-yl)-1,4-dimethyl-1H-pyrazole-3-carboxylic acid amide
36  5-[5-Cyclopropyl-2-(trifluoromethyloxy)-phenyl]-N-(2,6-difluoro-phenyl)-1-methyl-1H-pyrazole-3-carboxylic acid amide
37  5-[5-Cyclopropyl-2-(trifluoromethyloxy)-phenyl]-N-(3,5-difluoro-pyridin-4-yl)-1-methyl-1H-pyrazole-3-carboxylic acid amide
38  5-[5-Cyclopropyl-2-(trifluoromethyloxy)-phenyl]-N-(3-fluoro-pyridin-4-yl)-1-methyl-1H-pyrazole-3-carboxylic acid amide
39  5-[4-Cyclopropyl-2-(trifluoromethyloxy)-phenyl]-N-(2,6-difluoro-phenyl)-1-methyl-1H-pyrazole-3-carboxylic acid amide
40  5-[4-Cyclopropyl-2-(trifluoromethyloxy)-phenyl]-N-(3,5-difluoro-pyridin-4-yl)-1-methyl-1H-pyrazole-3-carboxylic acid amide
41  5-[4-Cyclopropyl-2-(trifluoromethyloxy)-phenyl]-N-(3-fluoro-pyridin-4-yl)-1-methyl-1H-pyrazole-3-carboxylic acid amide
42  2,6-Difluoro-N-[1-methyl-5-(3-thiazol-2-yl-phenyl)-1H-pyrazol-3-yl]-benzamide,
43  4-Amino-N-(3,5-difluoro-pyridin-4-yl)-1-methyl-5-(2-methyl-5-oxazol-2-yl-phenyl)-1H-pyrazole-3-carboxylic acid amide
44  4-Amino-N-(2,6-difluoro-phenyl)-5-(2-methoxy-5-thiazol-2-yl-phenyl)-1-methyl-1H-pyrazole-3-carboxylic acid amide
45  4-amino-N-(3,5-difluoropyridin-4-yl)-5-(2-methoxy-5-(oxazol-2-yl)phenyl)-1-methyl-1H-pyrazole-3-carboxamide
46  4-amino-N-(2,6-difluorophenyl)-5-(2-methoxy-5-(oxazol-2-yl)phenyl)-1-methyl-1H-pyrazole-3-carboxamide
47  4-amino-N-(3,5-difluoropyridin-4-yl)-5-(2-methoxy-5-(thiazol-2-yl)phenyl)-1-methyl-1H-pyrazole-3-carboxamide
48  4-amino-N-(2,6-difluorophenyl)-5-(5-(5,5-dimethyl-4-oxo-4,5-dihydroisoxazol-3-yl)-2-methoxyphenyl)-1-methyl-1H-pyrazole-3-carboxamide
49  4-amino-N-(2,6-difluorophenyl)-1-methyl-5-(5-(oxazol-2-yl)-2-(trifluoromethoxy)phenyl)-1H-pyrazole-3-carboxamide
50  4-amino-N-(3,5-difluoropyridin-4-yl)-1-methyl-5-(5-(oxazol-2-yl)-2-(trifluoromethoxy)phenyl)-1H-pyrazole-3-carboxamide optionally in the form of a single stereoisomer or a mixture of stereoisomers, in the form of the free compound and/or a physiologically acceptable salt or solvate thereof.

12. A pharmaceutical composition comprising at least one compound according to claim 1 and optionally one or more suitable, pharmaceutically compatible auxiliaries and/or one or more further pharmacologically active compounds.

13. A method for the treatment of one or more disorders selected from the group consisting of inflammatory disorders and/or autoimmune diseases and/or allergic disorders comprising administering a compound according to claim 1 to a patient in need thereof, wherein the autoimmune diseases are one or more autoimmune diseases selected from the group consisting of alopecia areata, psoriasis, dermatitis herpetiformis, pemphigus vulgaris, bullous pemphigoid, vitiligo, coeliac disease, Crohn's disease, ulcerative colitis, primary biliary cirrhosis, autoimmune hepatitis, Sjogren's syndrome, rheumatoid arthritis, systemic lupus erythematosus, scleroderma, polymyositis, dermatomyositis, ankylosing spondylitis and psoriatic arthritis.

14. A method for the treatment of psoriasis and/or psoriatic arthritis and/or rheumatoid arthritis and/or inflammatory bowel disease and/or asthma and/or allergic rhinitis comprising administering a compound according to claim 1 to a patient in need thereof.

15. A compound according to claim 2 wherein $R^2$ is selected from the group consisting of H, Cl, $CH_3$, and $CH_2CH_3$.

16. A compound according to claim 3 wherein $R^1$ denotes $CH_3$ or $CH_2CH_3$.

17. A compound according to claim 6 wherein $R^{10}$ is selected from the group consisting of H; F; Cl; CN; $CF_3$; $CF_2H$; and $CFH_2$.

\* \* \* \* \*